US012257022B2

(12) United States Patent
Al-Ali et al.

(10) Patent No.: US 12,257,022 B2
(45) Date of Patent: Mar. 25, 2025

(54) SYSTEM FOR TRANSMISSION OF SENSOR DATA USING DUAL COMMUNICATION PROTOCOL

(71) Applicant: MASIMO CORPORATION, Irvine, CA (US)

(72) Inventors: Ammar Al-Ali, San Juan Capistrano, CA (US); Stephen Scruggs, Newport Beach, CA (US); Richard Priddell, Irvine, CA (US); Chad A. DeJong, Los Angeles, CA (US); Eric Karl Kinast, Santa Ana, CA (US); Jung Soo Hwang, Irvine, CA (US); Steven Hang, Santa Ana, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 17/665,389

(22) Filed: Feb. 4, 2022

(65) Prior Publication Data

US 2022/0225878 A1 Jul. 21, 2022

Related U.S. Application Data

(63) Continuation of application No. 16/599,017, filed on Oct. 10, 2019, now Pat. No. 11,272,839.

(Continued)

(51) Int. Cl.
*A61B 5/00* (2006.01)

(52) U.S. Cl.
CPC ............ *A61B 5/002* (2013.01); *A61B 5/0024* (2013.01); *A61B 2560/045* (2013.01); *A61B 2560/0456* (2013.01)

(58) Field of Classification Search
CPC . A61B 5/002; A61B 5/0024; A61B 2560/045; A61B 2560/0456; H04Q 9/00;
(Continued)

(56) References Cited

U.S. PATENT DOCUMENTS 3,646,606 A 2/1972 Buxton et al.
3,690,313 A 9/1972 Weber et al.
(Continued)

FOREIGN PATENT DOCUMENTS

CN 301342850 9/2010
CN 302423595 5/2013
(Continued)

OTHER PUBLICATIONS

US 2022/0192529 A1, 06/2022, Al-Ali et al. (withdrawn)
(Continued)

*Primary Examiner* — Franklin D Balseca
(74) *Attorney, Agent, or Firm* — Knobbe, Martens, Olson & Bear, LLP

(57) ABSTRACT

Medical patient monitoring sensor devices including a disposable sensor assembly and a reusable pairing device are disclosed. The disposable sensor assembly can collect patient physiological data and provide power for the reusable pairing device. The reusable pairing device can establish wireless communication with a monitoring device. Once the reusable pairing device receives patient physiological data from the disposable sensor assembly, the reusable pairing device can wirelessly transmit the data to the computing device via the wireless communication.

18 Claims, 34 Drawing Sheets

Related U.S. Application Data

(60) Provisional application No. 62/744,988, filed on Oct. 12, 2018.

(58) Field of Classification Search
CPC .......... H04Q 2209/00; H04Q 2209/10; H04Q 2209/40; H04Q 2209/43; H04Q 2209/50; H04Q 2209/70; H04Q 2209/80; H04Q 2209/82; H04Q 2209/826; H04Q 2209/84; H04Q 2209/88
See application file for complete search history.

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,108,166 A | 8/1978 | Schmid |
| 4,129,125 A | 12/1978 | Lester et al. |
| 4,226,006 A | 10/1980 | Toyama |
| 4,231,354 A | 11/1980 | Kurtz et al. |
| D265,508 S | 7/1982 | Rusteberg |
| D268,300 S | 3/1983 | Richards |
| 4,589,415 A | 5/1986 | Haaga |
| 4,662,378 A | 5/1987 | Thomis |
| 4,815,172 A | 3/1989 | Ward et al. |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 4,966,154 A | 10/1990 | Cooper et al. |
| 5,041,187 A | 8/1991 | Hink et al. |
| 5,069,213 A | 12/1991 | Hink et al. |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Schimizu |
| 5,375,604 A | 12/1994 | Kelly |
| 5,377,676 A | 1/1995 | Vari et al. |
| D356,441 S | 3/1995 | Scheller |
| 5,400,794 A | 3/1995 | Gorman |
| D357,982 S | 5/1995 | Dahl et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,566,678 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang |
| 5,724,580 A | 3/1998 | Levin et al. |
| 5,724,983 A | 3/1998 | Selker et al. |
| 5,725,308 A | 3/1998 | Smith et al. |
| 5,726,440 A | 3/1998 | Kalkhoran et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| D406,001 S | 2/1999 | Nemeth |
| 5,876,351 A | 3/1999 | Rohde |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |
| 5,934,925 A | 8/1999 | Tobler et al. |
| 5,940,182 A | 8/1999 | Lepper, Jr. et al. |
| 5,941,836 A | 8/1999 | Friedman |
| 5,942,986 A | 8/1999 | Shabot et al. |
| D415,892 S | 11/1999 | Angus et al. |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |

(56) References Cited

U.S. PATENT DOCUMENTS

| | | | |
|---|---|---|---|
| 6,011,986 A | 1/2000 | Diab et al. |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang |
| 6,036,642 A | 3/2000 | Diab et al. |
| 6,036,718 A | 3/2000 | Ledford et al. |
| 6,040,578 A | 3/2000 | Malin et al. |
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,129,686 A | 10/2000 | Friedman |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,175,752 B1 | 1/2001 | Say et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| D449,304 S | 10/2001 | Herath |
| D449,617 S | 10/2001 | Herath |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,319,205 B1 | 11/2001 | Goor et al. |
| 6,321,100 B1 | 11/2001 | Parker |
| 6,322,502 B1 | 11/2001 | Schoenberg et al. |
| 6,322,515 B1 | 11/2001 | Goor et al. |
| D452,495 S | 12/2001 | Murnaghan et al. |
| D452,496 S | 12/2001 | Murnaghan et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,363,269 B1 | 3/2002 | Hanna et al. |
| D456,074 S | 4/2002 | McCurry |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,461,305 B1 | 10/2002 | Schnall |
| 6,463,311 B1 | 10/2002 | Diab |
| 6,470,199 B1 | 10/2002 | Kopotic et al. |
| 6,470,893 B1 | 10/2002 | Boesen |
| 6,487,429 B2 | 11/2002 | Hockersmith et al. |
| 6,488,633 B1 | 12/2002 | Schnall |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,967 B1 * | 2/2003 | Shrim .............. H01M 12/065 |
| | | 429/159 |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| D471,354 S | 3/2003 | Daniels |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,578,428 B1 | 6/2003 | Dromms et al. |
| 6,580,086 B1 | 6/2003 | Schulz et al. |
| 6,582,393 B2 | 6/2003 | Sage, Jr. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| D481,537 S | 11/2003 | Vaughn |
| 6,641,533 B2 | 11/2003 | Causey et al. |
| 6,643,530 B2 | 11/2003 | Diab et al. |
| 6,646,556 B1 | 11/2003 | Smith et al. |
| 6,650,917 B2 | 11/2003 | Diab et al. |
| 6,650,939 B2 | 11/2003 | Taepke, II et al. |
| 6,654,624 B2 | 11/2003 | Diab et al. |
| D483,872 S | 12/2003 | Cruz et al. |
| D483,939 S | 12/2003 | Kountz et al. |
| 6,658,276 B2 | 12/2003 | Kiani et al. |
| 6,661,161 B1 | 12/2003 | Lanzo et al. |
| 6,663,570 B2 | 12/2003 | Mott et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |

(56) References Cited

U.S. PATENT DOCUMENTS

| | | |
|---|---|---|
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia |
| 6,750,463 B1 | 6/2004 | Riley |
| 6,751,492 B2 | 6/2004 | Ben-Haim |
| 6,760,607 B2 | 7/2004 | Al-Ali |
| 6,766,188 B2 | 7/2004 | Soller |
| 6,770,028 B1 | 8/2004 | Ali et al. |
| 6,771,994 B2 | 8/2004 | Kiani et al. |
| 6,783,492 B2 | 8/2004 | Dominguez |
| 6,788,965 B2 | 9/2004 | Ruchti et al. |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,840,904 B2 | 1/2005 | Goldberg |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,876,931 B2 | 4/2005 | Lorenz et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-Haim |
| 6,916,289 B2 | 7/2005 | Schnall |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,304 B2 | 9/2005 | Schnall et al. |
| 6,939,305 B2 | 9/2005 | Flaherty et al. |
| 6,943,348 B1 | 9/2005 | Coffin IV |
| 6,950,687 B2 | 9/2005 | Al-Ali |
| D510,186 S | 10/2005 | Bell |
| 6,952,340 B2 | 10/2005 | Son |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-Haim |
| 6,985,764 B2 | 1/2006 | Mason et al. |
| 6,988,989 B2 | 1/2006 | Weiner et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,004,907 B2 | 2/2006 | Banet et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,044,930 B2 | 5/2006 | Stromberg |
| 7,048,687 B1 | 5/2006 | Reuss et al. |
| 7,063,666 B2 | 6/2006 | Weng et al. |
| 7,067,893 B2 | 6/2006 | Mills et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,029 S | 9/2006 | Sekine |
| D529,283 S | 10/2006 | Vivar et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,179,228 B2 | 2/2007 | Banet |
| 7,186,966 B2 | 3/2007 | Ai-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,229,415 B2 | 6/2007 | Schwartz |
| 7,238,159 B2 | 7/2007 | Banet et al. |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,256,708 B2 | 8/2007 | Rosenfeld |
| 7,261,697 B2 | 8/2007 | Berstein |
| 7,264,616 B2 | 9/2007 | Shehada et al. |
| 7,267,671 B2 | 9/2007 | Shehada et al. |
| 7,268,859 B2 | 9/2007 | Sage, Jr. et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,298,938 B2 | 11/2007 | Johnston |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,328,053 B1 | 2/2008 | Diab et al. |
| 7,332,784 B2 | 2/2008 | Mills et al. |
| 7,336,187 B2 | 2/2008 | Hubbard, Jr. et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |

(56) References Cited

U.S. PATENT DOCUMENTS

| | | |
|---|---|---|
| 7,355,512 B1 | 4/2008 | Al-Ali |
| 7,356,178 B2 | 4/2008 | Ziel et al. |
| 7,356,365 B2 | 4/2008 | Schurman |
| 7,361,155 B2 | 4/2008 | Sage, Jr. et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,378,975 B1 | 5/2008 | Smith et al. |
| 7,382,247 B2 | 6/2008 | Welch et al. |
| 7,383,070 B2 | 6/2008 | Diab et al. |
| 7,390,299 B2 | 6/2008 | Weiner et al. |
| 7,395,158 B2 | 7/2008 | Monfre et al. |
| 7,395,216 B2 | 7/2008 | Rosenfeld |
| 7,396,330 B2 | 7/2008 | Banet et al. |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| D582,043 S | 12/2008 | Koike et al. |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,481,772 B2 | 1/2009 | Banet |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| D596,635 S | 7/2009 | Owens et al. |
| D597,093 S | 7/2009 | Neu et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,588,558 B2 | 9/2009 | Sage, Jr. et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,658,716 B2 | 2/2010 | Banet et al. |
| 7,661,976 B2 | 2/2010 | Ma |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,803,120 B2 | 9/2010 | Banet et al. |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| D628,795 S | 12/2010 | Sanders |
| D628,797 S | 12/2010 | Kalbach |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,942,691 B1 | 5/2011 | McSweyn |
| 7,951,086 B2 | 5/2011 | Flaherty et al. |
| 7,957,780 B2 | 6/2011 | Lamego et al. |
| 7,962,188 B2 | 6/2011 | Kiani et al. |

(56) References Cited

U.S. PATENT DOCUMENTS

| | | |
|---|---|---|
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Ali et al. |
| 7,991,463 B2 | 8/2011 | Kelleher et al. |
| 7,991,625 B2 | 8/2011 | Rosenfeld |
| 7,993,275 B2 | 8/2011 | Banet et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| D652,379 S | 1/2012 | Vandiver |
| 8,094,013 B1 | 1/2012 | Lee et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,180,440 B2 | 5/2012 | McCombie et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,200,308 B2 | 6/2012 | Zhang et al. |
| 8,200,321 B2 | 6/2012 | McCombie et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,010 B2 | 8/2012 | Banet et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| D669,375 S | 10/2012 | Kao et al. |
| 8,280,473 B2 | 10/2012 | Al-Ali |
| 8,294,588 B2 | 10/2012 | Fisher et al. |
| 8,294,716 B2 | 10/2012 | Lord et al. |
| 8,295,521 B2 * | 10/2012 | Chan .................. H04R 25/602 381/322 |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,004 B2 | 11/2012 | Moon et al. |
| 8,321,150 B2 | 11/2012 | Taylor |
| RE43,860 E | 12/2012 | Parker |
| 8,326,649 B2 | 12/2012 | Rosenfeld |
| 8,328,793 B2 | 12/2012 | Birkenbach |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,364,250 B2 | 1/2013 | Moon et al. |
| 8,374,665 B2 | 2/2013 | Lamego |
| 8,385,995 B2 | 2/2013 | Al-Ali et al. |
| 8,385,996 B2 | 2/2013 | Smith et al. |
| D677,792 S | 3/2013 | Vandiver |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,419,649 B2 | 4/2013 | Banet et al. |
| 8,423,106 B2 | 4/2013 | Lamego et al. |
| 8,428,967 B2 | 4/2013 | Olsen et al. |
| 8,430,817 B1 | 4/2013 | Al-Ali et al. |
| D682,835 S | 5/2013 | Daniel |
| 8,437,824 B2 | 5/2013 | Moon et al. |
| 8,437,825 B2 | 5/2013 | Dalvi et al. |
| 8,442,607 B2 | 5/2013 | Banet et al. |
| 8,449,469 B2 | 5/2013 | Banet et al. |
| D683,960 S | 6/2013 | Robbins et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| D685,189 S | 7/2013 | Adelman et al. |
| 8,475,370 B2 | 7/2013 | McCombie et al. |
| 8,483,787 B2 | 7/2013 | Al-Ali et al. |
| 8,485,448 B2 | 7/2013 | Maizlin et al. |
| 8,489,167 B2 | 7/2013 | Buxton |
| 8,489,364 B2 | 7/2013 | Weber et al. |
| 8,498,684 B2 | 7/2013 | Weber et al. |
| 8,504,128 B2 | 8/2013 | Blank et al. |
| 8,506,480 B2 | 8/2013 | Banet et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,527,038 B2 | 9/2013 | Moon et al. |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,545,417 B2 | 10/2013 | Banet et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |

(56) References Cited

U.S. PATENT DOCUMENTS

| | | |
|---|---|---|
| 8,554,297 B2 | 10/2013 | Moon et al. |
| 8,560,032 B2 | 10/2013 | Al-Ali et al. |
| 8,560,034 B1 | 10/2013 | Diab et al. |
| 8,565,847 B2 | 10/2013 | Buxton et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,574,161 B2 | 11/2013 | Banet et al. |
| 8,577,431 B2 | 11/2013 | Lamego et al. |
| 8,578,082 B2 | 11/2013 | Medina et al. |
| 8,579,813 B2 | 11/2013 | Causey |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,591,411 B2 | 11/2013 | Banet et al. |
| 8,594,776 B2 | 11/2013 | McCombie et al. |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,602,997 B2 | 12/2013 | Banet et al. |
| 8,606,342 B2 | 12/2013 | Diab |
| 8,620,678 B2 | 12/2013 | Gotlib |
| D697,626 S | 1/2014 | Laplante et al. |
| 8,622,922 B2 | 1/2014 | Banet et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Ai-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,672,854 B2 | 3/2014 | McCombie et al. |
| 8,676,286 B2 | 3/2014 | Weber et al. |
| 8,682,407 B2 | 3/2014 | Ai-Ali |
| RE44,823 E | 4/2014 | Parker |
| RE44,875 E | 4/2014 | Kiani et al. |
| D703,671 S | 4/2014 | Hackett et al. |
| 8,688,183 B2 | 4/2014 | Bruinsma et al. |
| 8,690,771 B2 | 4/2014 | Wekell et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | Macneish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,727,977 B2 | 5/2014 | Banet et al. |
| 8,738,118 B2 | 5/2014 | Moon et al. |
| D706,752 S | 6/2014 | Myung et al. |
| 8,740,792 B1 | 6/2014 | Kiani et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,758,045 B2 | 6/2014 | McSweyn |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,808,188 B2 | 8/2014 | Banet et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| D715,667 S | 10/2014 | Shigeno et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| D717,309 S | 11/2014 | Govindarajan |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,700 B2 | 11/2014 | Banet et al. |
| 8,888,708 B2 | 11/2014 | Diab et al. |
| 8,892,180 B2 | 11/2014 | Weber et al. |
| 8,897,847 B2 | 11/2014 | Al-Ali |
| D719,668 S | 12/2014 | Cien et al. |
| D719,860 S | 12/2014 | Just et al. |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Ai-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell et al. |
| 8,956,293 B2 | 2/2015 | McCombie et al. |
| 8,956,294 B2 | 2/2015 | McCombie et al. |
| 8,965,471 B2 | 2/2015 | Lamego |
| 8,979,765 B2 | 3/2015 | Banet et al. |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| D728,230 S | 5/2015 | Oas |
| 9,028,429 B2 | 5/2015 | Telfort et al. |
| 9,037,207 B2 | 5/2015 | Al-Ali et al. |
| 9,055,928 B2 | 6/2015 | McCombie et al. |
| 9,057,689 B2 | 6/2015 | Soller |
| 9,060,721 B2 | 6/2015 | Reichgott et al. |
| 9,066,666 B2 | 6/2015 | Kiani |
| 9,066,680 B1 | 6/2015 | Al-Ali et al. |
| D733,598 S | 7/2015 | Just et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,104,789 B2 | 8/2015 | Gross et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |

(56) References Cited

U.S. PATENT DOCUMENTS

| | | |
|---|---|---|
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| D741,865 S | 10/2015 | Sundermeyer et al. |
| 9,149,192 B2 | 10/2015 | Banet et al. |
| 9,149,228 B2 | 10/2015 | Kinast |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,700 B2 | 10/2015 | Banet et al. |
| 9,161,713 B2 | 10/2015 | Al-Ali et al. |
| 9,167,995 B2 | 10/2015 | Lamego et al. |
| D744,109 S | 11/2015 | Yoneta et al. |
| 9,173,593 B2 | 11/2015 | Banet et al. |
| 9,173,594 B2 | 11/2015 | Banet et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,215,986 B2 | 12/2015 | Banet et al. |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,248,299 B2 | 2/2016 | Toy et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,915 B2 | 4/2016 | McCombie et al. |
| 9,307,928 B1 | 4/2016 | Al-Ali et al. |
| 9,318,840 B2 | 4/2016 | Siev et al. |
| 9,323,894 B2 | 4/2016 | Kiani |
| D755,183 S | 5/2016 | Patel et al. |
| D755,392 S | 5/2016 | Hwang et al. |
| 9,326,712 B1 | 5/2016 | Kiani |
| 9,333,316 B2 | 5/2016 | Kiani |
| 9,339,209 B2 * | 5/2016 | Banet .................. A61B 5/0002 |
| 9,339,211 B2 | 5/2016 | Banet et al. |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,158 B2 | 6/2016 | Banet et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,380,952 B2 | 7/2016 | Banet et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| D765,083 S | 8/2016 | Breitweiser et al. |
| 9,408,542 B1 | 8/2016 | Kinast et al. |
| 9,408,573 B2 | 8/2016 | Welch et al. |
| 9,436,645 B2 | 9/2016 | Al-Ali et al. |
| 9,439,574 B2 | 9/2016 | McCombie et al. |
| 9,443,059 B2 | 9/2016 | Grubis |
| 9,445,759 B1 | 9/2016 | Lamego et al. |
| D769,973 S | 10/2016 | Benoni |
| 9,466,919 B2 | 10/2016 | Kiani et al. |
| 9,474,474 B2 | 10/2016 | Lamego et al. |
| D771,057 S | 11/2016 | Wurts et al. |
| 9,480,422 B2 | 11/2016 | Al-Ali |
| 9,480,435 B2 | 11/2016 | Olsen |
| 9,480,846 B2 | 11/2016 | Strother et al. |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,529,762 B2 | 12/2016 | Gisler et al. |
| D776,664 S | 1/2017 | Hendrick |
| D776,916 S | 1/2017 | Yeruva et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| D782,483 S | 3/2017 | Patel et al. |
| 9,591,975 B2 | 3/2017 | Dalvi et al. |
| D783,170 S | 4/2017 | Carreon et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,706,964 B2 | 7/2017 | Ferber et al. |
| D794,807 S | 8/2017 | Kranz et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Ai-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| D803,841 S | 11/2017 | Kim et al. |
| D803,842 S | 11/2017 | Daniel |
| 9,808,188 B1 | 11/2017 | Perea et al. |
| 9,814,418 B2 | 11/2017 | Weber et al. |
| 9,820,691 B2 | 11/2017 | Kiani |
| D804,413 S | 12/2017 | McSweyn et al. |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |

(56) References Cited

U.S. PATENT DOCUMENTS

| | | |
|---|---|---|
| 9,848,807 B2 | 12/2017 | Lamego |
| D808,641 S | 1/2018 | Clover et al. |
| D809,147 S | 1/2018 | Coonahan et al. |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,866,255 B1 | 1/2018 | Ketter-Muldrow |
| 9,867,578 B2 | 1/2018 | Al-Ali et al. |
| 9,872,481 B2 | 1/2018 | Goldfain |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,883,800 B2 | 2/2018 | Pekander |
| 9,891,079 B2 | 2/2018 | Dalvi |
| 9,895,107 B2 | 2/2018 | Al-Ali et al. |
| D812,229 S | 3/2018 | Al-Siddiq |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,973,534 B2 | 5/2018 | Mahaffey et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| D829,574 S | 10/2018 | Mane et al. |
| D831,462 S | 10/2018 | McSweyn et al. |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| 10,130,306 B2 | 11/2018 | Katra et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,215 B2 * | 3/2019 | Cohrs .................. A61B 5/6831 |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| D850,628 S | 6/2019 | De Hoog et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,335,033 B2 | 7/2019 | Ai-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,374,350 B2 | 8/2019 | Nakazono et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| D874,657 S | 2/2020 | Bailey et al. |
| 10,555,678 B2 | 2/2020 | Dalvi et al. |
| 10,560,532 B2 | 2/2020 | Yang et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| D881,889 S | 4/2020 | Wang et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| 10,638,982 B2 | 5/2020 | Ferber et al. |

(56) References Cited

U.S. PATENT DOCUMENTS

| | | |
|---|---|---|
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,736,552 B2 | 8/2020 | Ferber et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,842,395 B2 | 11/2020 | Schnall et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| D910,623 S | 2/2021 | Cueto et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D916,705 S | 4/2021 | Liao |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,690 B2 * | 5/2021 | Giedwoyn ............. G16H 40/63 |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| D933,951 S | 10/2021 | Cardentey |
| 11,145,408 B2 | 10/2021 | Sampath et al. |
| 11,147,518 B1 | 10/2021 | Al-Ali et al. |
| 11,179,107 B2 * | 11/2021 | Chae ................. A61B 5/68335 |
| 11,185,262 B2 | 11/2021 | Al-Ali et al. |
| 11,191,484 B2 | 12/2021 | Kiani et al. |
| 11,201,500 B2 | 12/2021 | Partovi et al. |
| D944,520 S | 3/2022 | Akana et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,259,753 B2 | 3/2022 | Ferber et al. |
| 11,260,238 B2 | 3/2022 | Finch et al. |
| 11,272,839 B2 * | 3/2022 | Al-Ali .................. A61B 5/0015 |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| 11,331,463 B2 * | 5/2022 | Damiano ............. A61M 5/162 |
| D957,648 S | 7/2022 | Ai-Ai |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| D967,625 S | 10/2022 | Akana et al. |
| 11,457,703 B2 | 10/2022 | Calder |
| 11,457,733 B2 | 10/2022 | Gallup et al. |
| 11,464,410 B2 | 10/2022 | Muhsin |
| D968,410 S | 11/2022 | Zhang et al. |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,327 S | 6/2023 | Al-Ali et al. |
| 11,679,579 B2 | 6/2023 | Al-Ali |
| 11,684,296 B2 | 6/2023 | Vo et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,755,879 B2 | 9/2023 | Pascanu et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| D1,041,511 S | 9/2024 | Indorf et al. |
| 12,076,159 B2 | 9/2024 | Belur Nagaraj et al. |
| D1,044,828 S | 10/2024 | Chandran et al. |
| 12,114,974 B2 | 10/2024 | Al-Ali et al. |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039483 A1 | 11/2001 | Brand et al. |
| 2001/0046366 A1 | 11/2001 | Susskind |
| 2002/0010401 A1 | 1/2002 | Bushmakin et al. |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0063690 A1 | 5/2002 | Chung et al. |
| 2002/0072681 A1 | 6/2002 | Schnall |
| 2002/0099277 A1 | 7/2002 | Harry et al. |
| 2002/0133080 A1 | 9/2002 | Apruzzese et al. |
| 2002/0169439 A1 | 11/2002 | Flaherty |
| 2002/0177758 A1 | 11/2002 | Schoenberg |
| 2002/0198445 A1 | 12/2002 | Dominguez et al. |
| 2003/0004423 A1 | 1/2003 | Levie et al. |
| 2003/0013975 A1 | 1/2003 | Kiani |
| 2003/0018243 A1 | 1/2003 | Gerhardt et al. |

(56) References Cited

U.S. PATENT DOCUMENTS

| | | |
|---|---|---|
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0156288 A1 | 8/2003 | Barnum et al. |
| 2003/0158466 A1 | 8/2003 | Lynn et al. |
| 2003/0195401 A1 | 10/2003 | Tian et al. |
| 2003/0212312 A1 | 11/2003 | Coffin, IV et al. |
| 2003/0216670 A1 | 11/2003 | Beggs |
| 2004/0013647 A1 | 1/2004 | Solomon et al. |
| 2004/0073095 A1 | 4/2004 | Causey et al. |
| 2004/0090742 A1 | 5/2004 | Son et al. |
| 2004/0106163 A1 | 6/2004 | Workman, Jr. et al. |
| 2004/0116787 A1 | 6/2004 | Schnall |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0152957 A1 | 8/2004 | Stivoric et al. |
| 2004/0179332 A1 | 9/2004 | Smith et al. |
| 2004/0186357 A1 | 9/2004 | Soderberg et al. |
| 2004/0215085 A1 | 10/2004 | Schnall |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0005710 A1 | 1/2005 | Sage, Jr. |
| 2005/0009926 A1 | 1/2005 | Kreye et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055276 A1 | 3/2005 | Kiani et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack et al. |
| 2005/0125256 A1 | 6/2005 | Schoenberg |
| 2005/0148882 A1 | 7/2005 | Banet et al. |
| 2005/0164933 A1 | 7/2005 | Tymianski et al. |
| 2005/0191294 A1 | 9/2005 | Arap et al. |
| 2005/0208648 A1 | 9/2005 | Sage, Jr. et al. |
| 2005/0209518 A1 | 9/2005 | Sage, Jr. et al. |
| 2005/0228244 A1 | 10/2005 | Banet |
| 2005/0228299 A1 | 10/2005 | Banet |
| 2005/0234317 A1 | 10/2005 | Kiani |
| 2005/0242946 A1 | 11/2005 | Hubbard, Jr. et al. |
| 2005/0245831 A1 | 11/2005 | Banet |
| 2005/0245839 A1 | 11/2005 | Stivoric et al. |
| 2005/0261594 A1 | 11/2005 | Banet |
| 2005/0261598 A1 | 11/2005 | Banet et al. |
| 2005/0268401 A1 | 12/2005 | Dixon et al. |
| 2005/0277872 A1 | 12/2005 | Colby et al. |
| 2006/0009697 A1 | 1/2006 | Banet et al. |
| 2006/0009698 A1 | 1/2006 | Banet et al. |
| 2006/0049936 A1 | 3/2006 | Collins, Jr. et al. |
| 2006/0058647 A1 | 3/2006 | Strommer et al. |
| 2006/0073719 A1 | 4/2006 | Kiani |
| 2006/0084878 A1 | 4/2006 | Banet et al. |
| 2006/0085952 A1 | 4/2006 | Kaneko et al. |
| 2006/0089543 A1 | 4/2006 | Kim et al. |
| 2006/0094936 A1 | 5/2006 | Russ |
| 2006/0104824 A1 | 5/2006 | Schnall |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0189871 A1 | 8/2006 | Al-Ali et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0038050 A1 | 2/2007 | Sarussi |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0142715 A1 | 6/2007 | Banet et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0185393 A1 | 8/2007 | Zhou et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0250286 A1 | 10/2007 | Duncan et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2007/0276261 A1 | 11/2007 | Banet et al. |
| 2007/0276262 A1 | 11/2007 | Banet et al. |
| 2007/0276632 A1 | 11/2007 | Banet et al. |
| 2007/0282478 A1 | 12/2007 | Al-Ali et al. |
| 2007/0287898 A1 | 12/2007 | Lee et al. |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0051670 A1 | 2/2008 | Banet et al. |
| 2008/0053438 A1 | 3/2008 | DeVries et al. |
| 2008/0058614 A1 | 3/2008 | Banet et al. |
| 2008/0058657 A1 | 3/2008 | Schwartz et al. |
| 2008/0064965 A1 | 3/2008 | Jay et al. |
| 2008/0077024 A1 | 3/2008 | Schnall |
| 2008/0077026 A1 | 3/2008 | Banet et al. |
| 2008/0082004 A1 | 4/2008 | Banet et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0103375 A1 | 5/2008 | Kiani |
| 2008/0114220 A1 | 5/2008 | Banet et al. |
| 2008/0119412 A1 | 5/2008 | Tymianski et al. |
| 2008/0138278 A1 | 6/2008 | Scherz et al. |
| 2008/0139354 A1 | 6/2008 | Bell et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0208912 A1 | 8/2008 | Garibaldi |
| 2008/0221396 A1 | 9/2008 | Garces et al. |
| 2008/0221399 A1 | 9/2008 | Zhou et al. |
| 2008/0221418 A1 | 9/2008 | Al-Ali et al. |
| 2008/0221461 A1 | 9/2008 | Zhou et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0312518 A1 | 12/2008 | Jina et al. |
| 2008/0312542 A1 | 12/2008 | Banet et al. |

(56) References Cited

U.S. PATENT DOCUMENTS

| | | |
|---|---|---|
| 2008/0319275 A1 | 12/2008 | Chiu et al. |
| 2008/0319327 A1 | 12/2008 | Banet et al. |
| 2008/0319354 A1 | 12/2008 | Bell et al. |
| 2009/0005651 A1 | 1/2009 | Ward et al. |
| 2009/0018409 A1 | 1/2009 | Banet et al. |
| 2009/0018422 A1 | 1/2009 | Banet et al. |
| 2009/0018453 A1 | 1/2009 | Banet et al. |
| 2009/0018808 A1 | 1/2009 | Bronstein et al. |
| 2009/0024008 A1 | 1/2009 | Brunner et al. |
| 2009/0036759 A1 | 2/2009 | Ault et al. |
| 2009/0043172 A1 | 2/2009 | Zagorchev et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0069868 A1 | 3/2009 | Bengtsson et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0112072 A1 | 4/2009 | Banet et al. |
| 2009/0118628 A1 | 5/2009 | Zhou et al. |
| 2009/0119843 A1 | 5/2009 | Rodgers et al. |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0247924 A1 | 10/2009 | Lamego et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0309755 A1 | 12/2009 | Williamson |
| 2009/0322540 A1 | 12/2009 | Richardson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0056886 A1 | 3/2010 | Hurtubise et al. |
| 2010/0099964 A1 | 4/2010 | O'Reilly et al. |
| 2010/0125217 A1 | 5/2010 | Kuo et al. |
| 2010/0130875 A1 | 5/2010 | Banet et al. |
| 2010/0144627 A1 | 6/2010 | Vitek et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168536 A1 | 7/2010 | Banet et al. |
| 2010/0168589 A1 | 7/2010 | Banet et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0234718 A1 | 9/2010 | Sampath et al. |
| 2010/0261982 A1 | 10/2010 | Noury et al. |
| 2010/0270257 A1 | 10/2010 | Wachman et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | Mccombie et al. |
| 2010/0298660 A1 | 11/2010 | McCombie et al. |
| 2010/0298661 A1 | 11/2010 | Mccombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317951 A1 | 12/2010 | Rutkowski et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2011/0004079 A1 | 1/2011 | Al-Ali et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046495 A1 | 2/2011 | Osypka |
| 2011/0066051 A1 | 3/2011 | Moon et al. |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0092831 A1 | 4/2011 | Herscovivi-Cohen et al. |
| 2011/0092857 A1 | 4/2011 | Herscovivi-Cohen et al. |
| 2011/0098583 A1 | 4/2011 | Pandia et al. |
| 2011/0105956 A1 | 5/2011 | Hirth |
| 2011/0118561 A1 | 5/2011 | Tari et al. |
| 2011/0118573 A1 | 5/2011 | Mckenna |
| 2011/0125060 A1 | 5/2011 | Telfort et al. |
| 2011/0137297 A1 | 6/2011 | Kiani et al. |
| 2011/0152629 A1 | 6/2011 | Eaton et al. |
| 2011/0172498 A1 | 7/2011 | Olsen et al. |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208073 A1 | 8/2011 | Matsukawa et al. |
| 2011/0212090 A1 | 9/2011 | Pedersen et al. |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon et al. |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0230733 A1 | 9/2011 | Al-Ali |
| 2011/0257489 A1 | 10/2011 | Banet et al. |
| 2011/0257544 A1 | 10/2011 | Kaasinen et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0263950 A1 | 10/2011 | Larson et al. |
| 2011/0288421 A1 | 11/2011 | Banet et al. |
| 2011/0295094 A1 | 12/2011 | Doyle et al. |
| 2012/0004579 A1 | 1/2012 | Luo et al. |
| 2012/0029300 A1 | 2/2012 | Paquet |
| 2012/0029304 A1 | 2/2012 | Medina et al. |
| 2012/0029879 A1 | 2/2012 | Sing et al. |
| 2012/0059230 A1 | 3/2012 | Teller et al. |
| 2012/0071771 A1 | 3/2012 | Behar |
| 2012/0075464 A1 | 3/2012 | Derenne et al. |
| 2012/0095778 A1 | 4/2012 | Gross et al. |
| 2012/0101353 A1 | 4/2012 | Reggiardo et al. |
| 2012/0108983 A1 | 5/2012 | Banet et al. |
| 2012/0123231 A1 | 5/2012 | O'Reilly |
| 2012/0123799 A1 | 5/2012 | Nolen et al. |
| 2012/0132717 A1 | 5/2012 | Maizlin et al. |
| 2012/0136221 A1 | 5/2012 | Killen et al. |
| 2012/0157806 A1 | 6/2012 | Stelger |
| 2012/0165629 A1 | 6/2012 | Merritt et al. |
| 2012/0165630 A1 | 6/2012 | Knight et al. |

(56) References Cited

U.S. PATENT DOCUMENTS

| | | |
|---|---|---|
| 2012/0179011 A1 | 7/2012 | Moon et al. |
| 2012/0184120 A1 | 7/2012 | Basta et al. |
| 2012/0190949 A1 | 7/2012 | McCombie et al. |
| 2012/0197619 A1 | 8/2012 | Namer Yelin et al. |
| 2012/0203078 A1 | 8/2012 | Sze et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0226160 A1 | 9/2012 | Kudoh |
| 2012/0239434 A1 | 9/2012 | Breslow et al. |
| 2012/0242501 A1 | 9/2012 | Tran et al. |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0294801 A1 | 11/2012 | Scherz et al. |
| 2012/0296174 A1 | 11/2012 | McCombie |
| 2012/0303476 A1 | 11/2012 | Krzyzanowski et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0046197 A1 | 2/2013 | Dlugos et al. |
| 2013/0060147 A1 | 3/2013 | Welch et al. |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109937 A1 | 5/2013 | Banet et al. |
| 2013/0116515 A1 | 5/2013 | Banet et al. |
| 2013/0123616 A1 | 5/2013 | Merritt et al. |
| 2013/0197364 A1 | 8/2013 | Han |
| 2013/0243021 A1 | 9/2013 | Siskavich |
| 2013/0253334 A1 | 9/2013 | Al-Ali et al. |
| 2013/0261494 A1 | 10/2013 | Bloom et al. |
| 2013/0279109 A1 | 10/2013 | Lindblad et al. |
| 2013/0296672 A1 | 11/2013 | O'Neil et al. |
| 2013/0296713 A1 | 11/2013 | Al-Ali et al. |
| 2013/0297330 A1 | 11/2013 | Kamen et al. |
| 2013/0317393 A1 | 11/2013 | Weiss et al. |
| 2013/0324804 A1 | 12/2013 | McKeown et al. |
| 2013/0324808 A1 | 12/2013 | Al-Ali et al. |
| 2013/0331036 A1 | 12/2013 | Baker et al. |
| 2013/0331660 A1 | 12/2013 | Al-Ali et al. |
| 2013/0340176 A1 | 12/2013 | Stevens et al. |
| 2013/0345921 A1 | 12/2013 | Al-Ali et al. |
| 2014/0005502 A1 | 1/2014 | Klap et al. |
| 2014/0012100 A1 | 1/2014 | Al-Ali et al. |
| 2014/0022081 A1 | 1/2014 | Ribble et al. |
| 2014/0025010 A1 | 1/2014 | Stroup et al. |
| 2014/0046674 A1 | 2/2014 | Rosenfeld |
| 2014/0051953 A1 | 2/2014 | Lamego et al. |
| 2014/0081099 A1 | 3/2014 | Banet et al. |
| 2014/0088385 A1 | 3/2014 | Moon et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0142445 A1 | 5/2014 | Banet et al. |
| 2014/0152673 A1 | 6/2014 | Lynn et al. |
| 2014/0163344 A1 | 6/2014 | Al-Ali |
| 2014/0163393 A1 | 6/2014 | McCombie et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0200415 A1 | 7/2014 | McCombie et al. |
| 2014/0200420 A1* | 7/2014 | Al-Ali .................. A61B 5/6826 600/479 |
| 2014/0213864 A1 | 7/2014 | Abdul-Hafiz et al. |
| 2014/0235964 A1 | 8/2014 | Banet et al. |
| 2014/0249431 A1 | 9/2014 | Banet et al. |
| 2014/0249432 A1 | 9/2014 | Banet et al. |
| 2014/0249433 A1 | 9/2014 | Banet et al. |
| 2014/0249434 A1 | 9/2014 | Banet et al. |
| 2014/0249435 A1 | 9/2014 | Banet et al. |
| 2014/0249440 A1 | 9/2014 | Banet et al. |
| 2014/0249441 A1 | 9/2014 | Banet et al. |
| 2014/0249442 A1 | 9/2014 | Banet et al. |
| 2014/0257056 A1 | 9/2014 | Moon et al. |
| 2014/0257057 A1 | 9/2014 | Reis Cunha et al. |
| 2014/0266787 A1 | 9/2014 | Tran |
| 2014/0275816 A1 | 9/2014 | Sandmore |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276145 A1 | 9/2014 | Banet et al. |
| 2014/0276175 A1 | 9/2014 | Banet et al. |
| 2014/0288400 A1 | 9/2014 | Diab et al. |
| 2014/0301893 A1 | 10/2014 | Stroup et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0336517 A1 | 11/2014 | Schnall |
| 2014/0343889 A1 | 11/2014 | Ben Shalom et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell et al. |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0164437 A1 | 6/2015 | McCombie et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0282708 A1 | 10/2015 | Schlottau et al. |
| 2015/0282717 A1 | 10/2015 | McCombie et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0022224 A1 | 1/2016 | Banet et al. |
| 2016/0029932 A1 | 2/2016 | Al-Ali |
| 2016/0045163 A1 | 2/2016 | Weisner et al. |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0106366 A1 | 4/2016 | Banet et al. |
| 2016/0143546 A1 | 5/2016 | McCombie et al. |
| 2016/0166183 A1 | 6/2016 | Al-Ali et al. |
| 2016/0166183 A1 | 6/2016 | Poeze et al. |
| 2016/0183836 A1* | 6/2016 | Muuranto .............. G16H 40/67 600/300 |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |

(56) References Cited

U.S. PATENT DOCUMENTS

| | | |
|---|---|---|
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0321420 A1 | 11/2016 | Klee et al. |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Ai-Ali |
| 2017/0055905 A1 | 3/2017 | Cohrs et al. |
| 2017/0079594 A1 | 3/2017 | Telfort et al. |
| 2017/0086723 A1 | 3/2017 | Al-Ali et al. |
| 2017/0119252 A1* | 5/2017 | Kim .................... A61B 5/0024 |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0332980 A1 | 11/2017 | Fifield et al. |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0097373 A1 | 4/2018 | McSweyn et al. |
| 2018/0103874 A1 | 4/2018 | Lee et al. |
| 2018/0103905 A1 | 4/2018 | Kiani |
| 2018/0110478 A1 | 4/2018 | Ai-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Ai-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216370 A1 | 7/2019 | Schurman et al. |

(56) References Cited

U.S. PATENT DOCUMENTS

| | | |
|---|---|---|
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0320906 A1 | 10/2019 | Olsen |
| 2019/0320988 A1 | 10/2019 | Ahmed et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0085321 A1 | 3/2020 | Hatch |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0251501 A1 | 8/2021 | Moon et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0125377 A1 | 4/2022 | Mendes-Roter et al. |
| 2022/0148724 A1 | 5/2022 | Pasternak et al. |
| 2022/0151521 A1 | 5/2022 | Krishnamani et al. |
| 2022/0211323 A1 | 7/2022 | Schnall |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0331065 A1 | 10/2022 | Shah et al. |
| 2022/0346724 A1 | 11/2022 | Ferber et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Ai-Ai |
| 2023/0038389 A1 | 2/2023 | Vo |
| 2023/0045647 A1 | 2/2023 | Vo |
| 2023/0058052 A1 | 2/2023 | Ai-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |

FOREIGN PATENT DOCUMENTS

| | | |
|---|---|---|
| CN | 108370502 | 8/2018 |
| EM | 001198584-0059 | 6/2010 |
| EP | 0 735 499 | 10/1996 |
| EP | 0 880 936 | 12/1998 |
| EP | 2 335 569 | 6/2011 |
| EP | 2 766 834 | 8/2014 |
| EP | 2 811 894 | 12/2014 |
| EP | 2 901 921 | 8/2015 |
| JP | H08-080288 | 3/1996 |
| JP | H10-336064 | 12/1998 |
| JP | 2002-513602 | 5/2002 |
| JP | 2002-165764 | 6/2002 |
| JP | 2002-172096 | 6/2002 |
| JP | 2002-542493 | 12/2002 |
| JP | 2004-337605 | 12/2004 |
| JP | 2005-218036 | 8/2005 |
| JP | 2005-295375 | 10/2005 |
| JP | 2005-532863 | 11/2005 |
| JP | 2007-021213 | 2/2007 |
| JP | 2007-095365 | 4/2007 |
| JP | 2007-174051 | 7/2007 |
| JP | 2008-126017 | 6/2008 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-524510 | 7/2010 |
| JP | 2011-519607 | 7/2011 |
| JP | 2011-152261 | 8/2011 |
| JP | 2014-533997 | 12/2014 |

(56) References Cited

FOREIGN PATENT DOCUMENTS

| | | |
|---|---|---|
| JP | 2015-511840 | 4/2015 |
| JP | 2016-538015 | 12/2016 |
| JP | 2017-506121 | 3/2017 |
| JP | D1605226 | 5/2018 |
| JP | 2018-527996 | 9/2018 |
| JP | D1614787 | 10/2018 |
| JP | D1665851 | 4/2019 |
| TW | D169966 | 8/2015 |
| TW | D182804 | 5/2017 |
| TW | D126452 | 12/2018 |
| TW | D207721 | 10/2020 |
| WO | WO 98/004182 | 2/1998 |
| WO | WO 98/029790 | 7/1998 |
| WO | WO 99/013766 | 3/1999 |
| WO | WO 99/056613 | 11/1999 |
| WO | WO 00/063713 | 10/2000 |
| WO | WO 00/074551 | 12/2000 |
| WO | WO 01/064101 | 9/2001 |
| WO | WO 2004/056266 | 7/2004 |
| WO | WO 2004/059551 | 7/2004 |
| WO | WO 2006/051461 | 5/2006 |
| WO | WO 2011/001302 | 1/2011 |
| WO | WO 2011/002904 | 1/2011 |
| WO | WO 2011/025549 | 3/2011 |
| WO | WO 2012/112891 | 8/2012 |
| WO | WO 2013/056160 | 4/2013 |
| WO | WO 2013/119982 | 8/2013 |
| WO | WO 2013/184283 | 12/2013 |
| WO | WO 2015/054665 | 4/2015 |
| WO | WO 2017/040700 | 3/2017 |
| WO | WO 2018/102142 | 6/2018 |
| WO | WO 2020/077149 | 4/2020 |

OTHER PUBLICATIONS

US 2024/0016391 A1, 01/2024, Lapotko et al. (withdrawn)
International Preliminary Report on Patentability and Written Opinion received in PCT Application No. PCT/US2019/055722, dated Apr. 22, 2021.
International Search Report and Written Opinion received in PCT Application No. PCT/US2021/031625 (MAS.1192PWO), dated Aug. 25, 2021.
International Preliminary Report on Patentability and Written Opinion received in PCT Application No. PCT/US2021/031625, dated Nov. 24, 2022.
International Search Report and Written Opinion received in PCT Application No. PCT/US2019/055722, dated Mar. 23, 2020.
PCT Invitation to Pay Additional Search Fees issued in application No. PCT/US2019/055722 on Jan. 30, 2020.
Adinstruments: "Human NIBP Controller Owner's Guide Human NIBP Owner's Guide", Jan. 1, 2014, XP055673095, Retrieved from the Internet: http://cdn.adinstruments.com/adi-web/manuals/human-nibp-OG.pdf [retrieved on Maar. 3, 2020), p. 16; figures 2-4, pp. 90.
U.S. Appl. No. 12/973,392, filed Dec. 20, 2010, Kiani et al.
U.S. Appl. No. 29/537,221, filed Aug. 24, 2015, Al-Ali et al.
Aminian et al., "Spatio-Temporal Parameters of Gait Measured by an Ambulatory System Using Miniature Gyroscopes", Journal of Biomechanics, 2002, vol. 35, pp. 689-699.
Anliker et al., "AMON: A Wearable Multiparameter Medical Monitoring and Alert System", IEEE Transactions on Information Technology in Biomedicine, vol. 8, No. 4, Dec. 2004, pp. 415-427.
Asada et al., "Mobile Monitoring with Wearable Photoplethysmographic Biosensors", IEEE Engineering in Medicine and Biology Magazine, May/Jun. 2003, pp. 28-40.
Ayello et al., "How and Why to Do Pressure Ulcer Risk Assessment", Advances in Skin & Wound Care, May/Jun. 2002, vol. 15, No. 3., pp. 125-133.
Bergstrom et al., "A Prospective Study of Pressure Sore Risk Among Institutionalized Elderly", Journal of the American Geriatrics Society, Aug. 1992, vol. 40, No. 8, pp. 747-758.
Bourke et al., "Evaluation of a Threshold-Based Tri-Axial Accelerometer Fall Detection Algoithm", Gait & Posture, vol. 26, 2007, pp. 194-199.
Campo et al., "Wireless Fall Sensor with GPS Location for Monitoring the Elderly", 30th Annual International IEEE EMBS Conference Vancouver, British Columbia, Canada, Aug. 20-24, 2008, pp. 498-501.
Caporusso et al., "A Pervasive Solution for Risk Awareness in the Context of Fall Prevention", Pervasive Health, 2009, pp. 8.
Capuano et at. "Remote Telemetry—New Twists for Old Technology." Nursing Management. vol. 26, No. 7. Jul. 1995.
Chen et al., "In-Bed Fibre Optic Breathing and Movement Sensor for Non-Intrusive Monitoring", Proceedings of SPIE vol. 7173, 2009, pp. 6.
Chen et al., "Wearable Sensors for Reliable Fall Detection", Proceedings of the 2005 IEEE Engineering in Medicine and Biology 27th Annual Conference, Shanghai, China, Sep. 1-4, 2005, pp. 3551-3554.
Degen et al., "Speedy: A Fall Detector in a Wrist Watch", Proceedings of the Seventh IEEE International Symposium on Wearable Computers (ISWC'03), 2003, pp. 184-187.
Dhillon et al., "Towards the Prevention of Pressure Ulcers with a Wearable Patient Posture Monitor Based on Adaptive Accelerometer Alignment", 34th Annual International Conference of the IEEE EMBS, San Diego, CA, Aug. 28-Sep. 1, 2012, pp. 4513-4516.
Di Rienzo et al., "MagIC System: a New Textile-BasedWearable Device for Biological Signal Monitoring. Applicability in Daily Life and Clinical Setting", Proceedings of the 2005 IEEE Engineering in Medicine and Biology 27th Annual Conference Shanghai, China, Sep. 1-4, 2005, pp. 7167-7169.
Dinh et al., "A Fall and Near-Fall Assessment and Evaluation System", The Open Biomedical Engineering Journal, 2009, vol. 3, pp. 1-7.
Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.
Giansanti et al., "Assessment of Fall-Risk by Means of a Neural Network Based on Parameters Assessed by a Wearable Device During Posturography", Medical Engineering & Physics, vol. 30, 2008, pp. 367-372.
Giansanti, Daniele, "Investigation of Fall-Risk Using a Wearable Device with Accelerometers and Rate Gyroscopes", Institute of Physics Publishing, Physiological Measurement, vol. 27, 2006, pp. 1081-1090.
Grundy et al. "Telemedicine in Critical Care: An Experiment in Health Care Delivery." Oct. 1977.
Grundy et al. "Telemedicine in Critical Care: Problems in design, implementation and assessment." vol. 10, No. 7. Jul. 1982.
Gunningberg et al., "Improved Quality and Comprehensiveness in Nursing Documentation of Pressure Ulcers after Implementing an Electronic Health Record in Hospital Care", Journal of Clinical Nursing, 2009, vol. 18, pp. 1557-1564.
Harada et al., "Portable Orientation Estimation Device Based on Accelerometers, Magnetometers and Gyroscope Sensors for Sensor Network", IEEE Conference on Multisensor Fusion and Integration for Intelligent Systems 2003, 2003, pp. 191-196.
Hwang et al., "Development of Novel Algorithm and Real-time Monitoring Ambulatory System Using Bluetooth Module for Fall Detection in the Elderly", Proceedings of the 26th Annual International Conference of the IEEE EMBS, Sep. 1-5, 2004, pp. 2204-2207.
Kärki et al., "Pressure Mapping System for Physiological Measurements", XVIII IMEKO World Congress, Metrology for a Sustainable Development, Sep. 17-22, 2006, Rio de Janeiro, Brazil, pp. 5.
Li et al., "Accurate, Fast Fall Detection Using Gyroscopes and Accelerometer-Derived Posture Information", Conference Paper, Sixth International Workshop on Wearable and Implantable Body Sensor Networks, BSN 2009, Berkeley, CA, USA, Jun. 3-5, 2009, pp. 6.
Lindemann et al., "Evaluation of a Fall Detector Based on Accelerometers: A Pilot Study", Medical & Biological Engineering & Computing, vol. 43, 2005, pp. 548-551.

(56) References Cited

OTHER PUBLICATIONS

Linder-Ganz et al., "Real-Time Continuous Monitoring of Sub-Dermal Tissue Stresses Under the Ischial Tuberosities in Individuals with Spinal Cord Injury", Proceedings of the ASME 2008 Summer Bioengineering Conference (SBC2008), Jun. 25-29, 2008, Marriott Resort, Marco Island, Florida, pp. 2.
Luo et al., "A Dynamic Motion Pattern Analysis Approach to Fall Detection", 2004 IEEE International Workshop on Biomedical Circuits & Systems, Dec. 1-3, 2004, pp. S2. 1-5-S2.1-8.
Masimo Sleep™, posted at masimopersonalhealth.com, no posting date, retrieved Nov. 17, 2021, online, https://www.masimopersonalhealth.com/pages/masimo-sleep (Year: 2021).
Masimo, "Radius-7—The Power of Masimo's Breakthrough Measurements in a Patient-worn Monitor," 2015, in 2 pages.
Mathie et al., "A System for Monitoring Posture and Physical Activity Using Accelerometers",Engineering in Medicine and Biology Society, 2001. Proceedings of the 23rd Annual International Conference of the IEEE, Oct. 25-28, 2001, pp. 3654-3657.
McInerney, Joan A., "Reducing Hospital-Acquired Pressure Ulcer Prevalence Through a Focused Prevention Program", Advances in Skin & Wound Care, vol. 21, No. 2, Feb. 2008, pp. 75-78.
Merbitz et al., "Wheelchair Push-ups: Measuring Pressure Relief Frequency", Archives of Physical Medicine and Rehabilitation, vol. 66, No. 7, Juy 1985, pp. 433-438.
Narayanan et al., "Falls Management: Detection and Prevention, Using a Waist-Mounted Triaxial Accelerometer", Proceedings of the 29th Annual International Conference of the IEEE EMBS Cité Internationale, Lyon, France, Aug. 23-26, 2007, pp. 4037-4040.
Notice of Allowance received in Taiwan Patent Office Application No. 108302030, dated Aug. 14, 2020 in 6 pages.
Notice of Allowance received in Taiwan Patent Office Application No. 108302035, dated Mar. 13, 2020 in 6 pages.
Notice of Allowance received in Taiwan Patent Office Application No. 108302046, dated Mar. 18, 2020 in 6 pages.
Notice of Allowance received in Taiwan Patent Office Application No. 109301079, dated Jul. 8, 2020 in 6 pages.
Notice of Allowance received in Taiwan Patent Office Application No. 109301080, dated Jul. 7, 2020 in 6 pages.
Notice of Allowance received in Taiwan Patent Office Application No. 109301129, dated Jul. 8, 2020 in 6 pages.
Notice of Allowance received in Taiwan Patent Office Application No. 109301130, dated Jul. 8, 2020 in 6 pages.
Notice of Allowance received in Taiwan Patent Office Application No. 109303055, dated Jan. 21, 2021 in 6 pages.
Notice of Allowance received in Taiwan Patent Office Application No. 109303056, dated Jan. 21, 2021 in 6 pages.
Notice of Allowance received in Taiwan Patent Office Application No. 109303057, dated Jan. 21, 2021 in 6 pages.
Noury, Norbert, "A Smart Sensor for the Remote Follow Up of Activity and Fall Detection of the Elderly", 2nd Annual International IEEE-EMBS Special Topic Conference on Microtechnologies in Medicine & Biology, May 2-4, 2002, pp. 314-317.
Nyan et al., "A Wearable System for Pre-Impact Fall Detection", Journal of Biomechanics, vol. 41, 2008, pp. 3475-3481.
Nyan et al., "Garment-Based Detection of Falls and Activities of Daily Living Using 3-Axis MEMS Accelerometer", Institute of Physics Publishing, International MEMS Conference 2006, Journal of Physics: Conference Series 34, 2006, pp. 1059-1067.
O'Donovan et al., "A Context Aware Wireless Body Area Network", Pervasive Health, 2009, pp. 8.
Pérolle et al., "Automatic Fall Detection and Activity Monitoring for Elderly", Jan. 2007, pp. 6.
Philips, "Small, lightweight, and cableless—Philips Mobile CL cuffs, sensors, and accessories" brochure, 2013, in 2 pages.
Po et al., "Overview of MEMSWear II—Incorporating MEMS Technology Into Smart Shirt for Geriatric Care", Institute of Physics Publishing, International MEMS Conference 2006, Journal of Physics: Conference Series 34, 2006, pp. 1079-1085.
Prado et al., "Distributed Intelligent Architecture for Falling Detection and Physical Activity Analysis in the Elderly", Proceedings of the Second Joint EMBS/BMES Conference, Oct. 23-26, 2002, pp. 1910-1911.
"Radius PPG™ Tetherless Pulse Oximetry", masimo.com, site visited Mar. 18, 2022: https://www.masimo.com/products/sensors/radius-ppg/, pp. 2.
Rithalia et al., "Quantification of Pressure Relief Using Interface Pressure and Tissue Perfusion in Alternating Pressure Air Mattresses", Archives of Physical Medicine and Rehabilitation, vol. 81, Oct. 2000, pp. 1364-1369.
Rysavy, "Making the Call with Two-Way Paging", Network Computing, Published Jan. 15, 1997, www.rysavy.com/Articles/twoway.htm.
Sakai et al., "Continuous Monitoring of Interface Pressure Distribution in Intensive Care Patients for Pressure Ulcer Prevention", Journal of Advanced Nursing, vol. 65, No. 4, 2009, pp. 809-817.
Spillman Jr., et al., "A 'Smart' Bed for Non-Intrusive Monitoring of Patient Physiological Factors", Measurement Science and Technology, Aug. 2004, vol. 15, No. 8, pp. 1614-1620.
Wachter, S. Blake; Journal of the American Medical Informatics Association; The Employment of an Iterative Design Process to Develop a Pulmonary Graphical Display; vol. 10, No. 4, Jul./Aug. 2003; pp. 363-372.
Wayback Machine search for "Masimo Sleep™", first found Sep. 24, 2020, retrieved Nov. 17, 2021, online, https://web.archive.org/web/20200924015943/https://www.masimopersonalhealth.com/pages/masimo-sleep (Year: 2020), pp. 8.
Webster, John G., "A Pressure Mat for Preventing Pressure Sores", IEEE Engineering in Medicine & Bioloogy Society 11th Annual International Conference, 1989, pp. 2.
Williams et al., "A Remote Electronic Monitoring System for the Prevention of Pressure Sores", Proceedings of the 19th International Conference, IEEE/EMBS Oct. 30-Nov. 2, 1997, Chicago, IL, pp. 1076-1079.
Wu et al., "Portable Preimpact Fall Detector With Inertial Sensors", IEEE Transactions on Neural Systems and Rehabilitation Engineering, vol. 16, No. 2, Apr. 2008, pp. 178-183.
Patil et al., "Telemonitoring Physiological Parameters of a Patient from a Distance by Near Field Communication Mobile", 2014 Fourth International Conference on Advanced Computing & Communication Technologies, pp. 345-348.
Yongwu, Shi, "Research progress of wearable medical devices", Medical Equipment, Mar. 2018, vol. 31, No. 5, pp. 3.

* cited by examiner

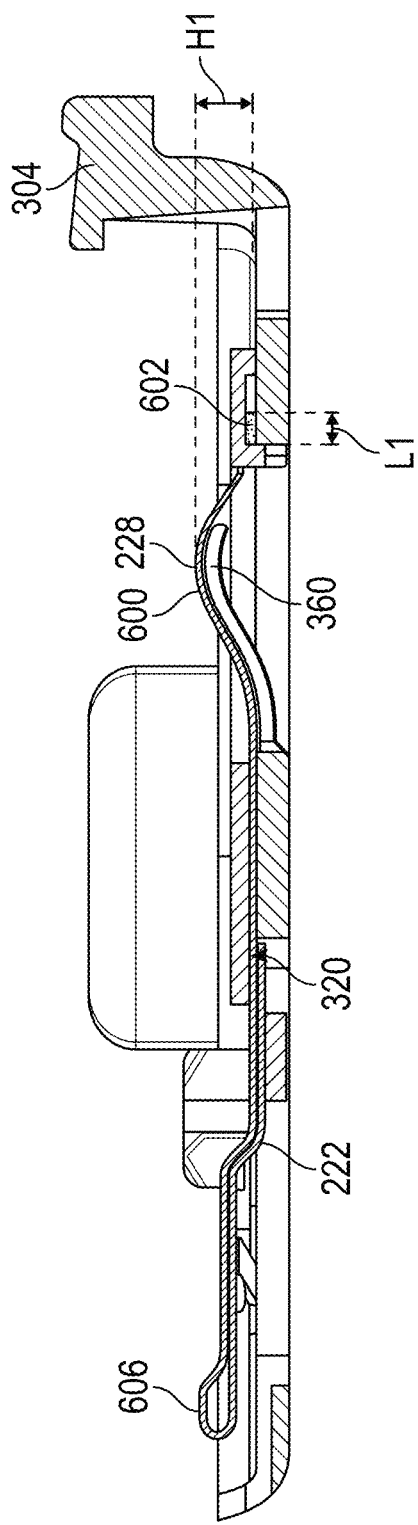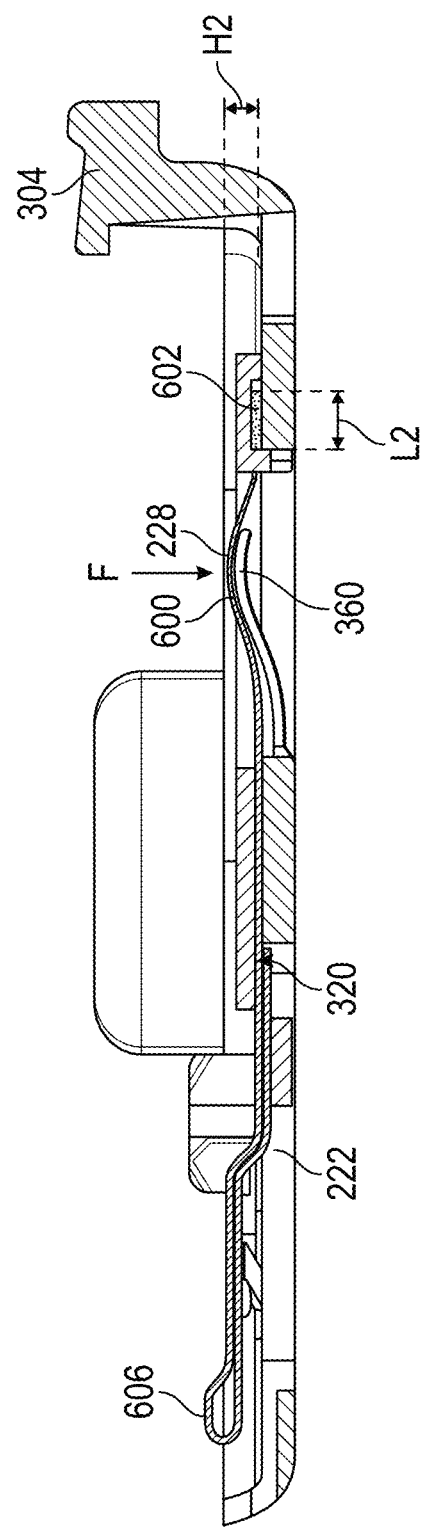
FIG. 6C
FIG. 6D

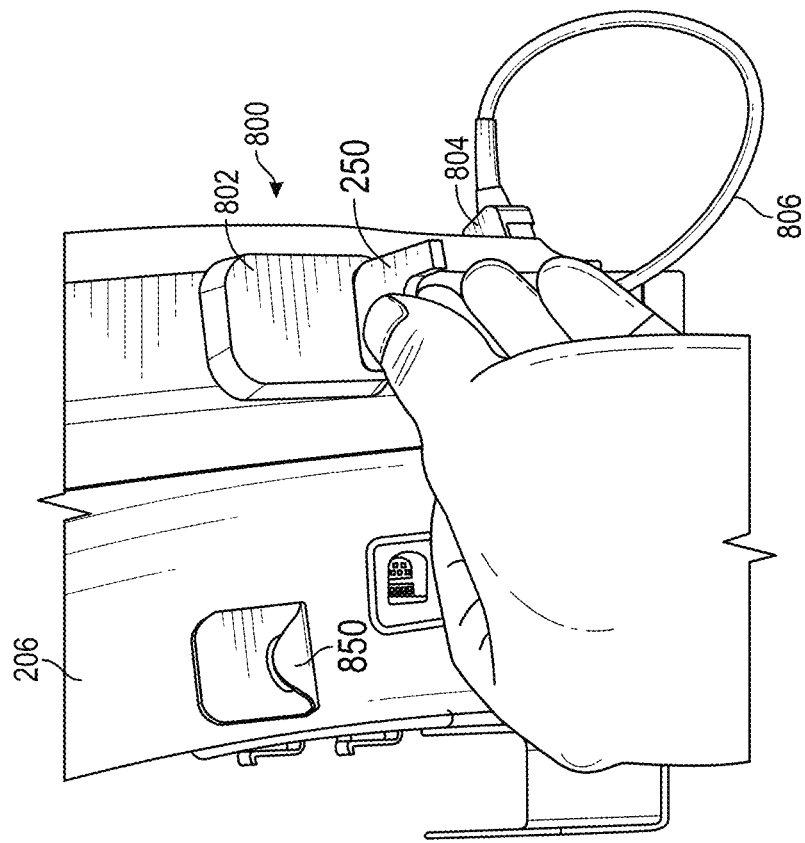
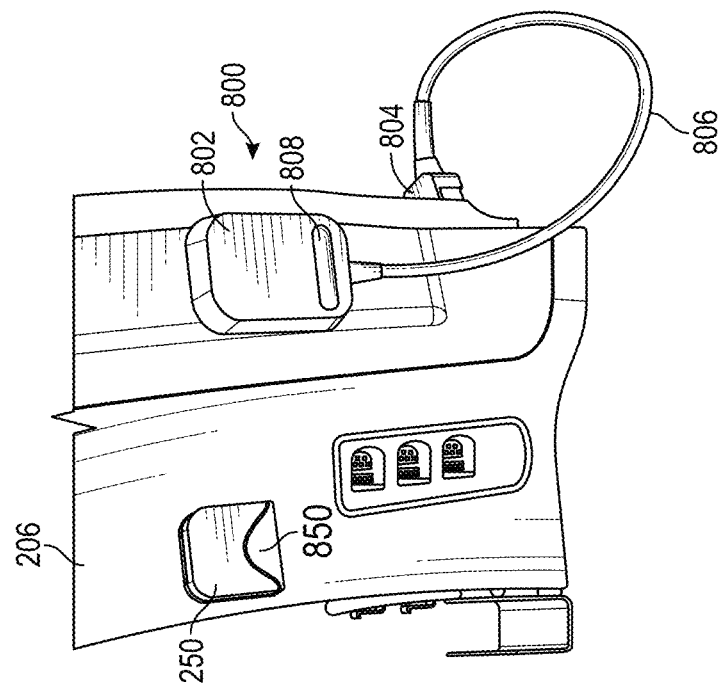
FIG. 9B
FIG. 9A

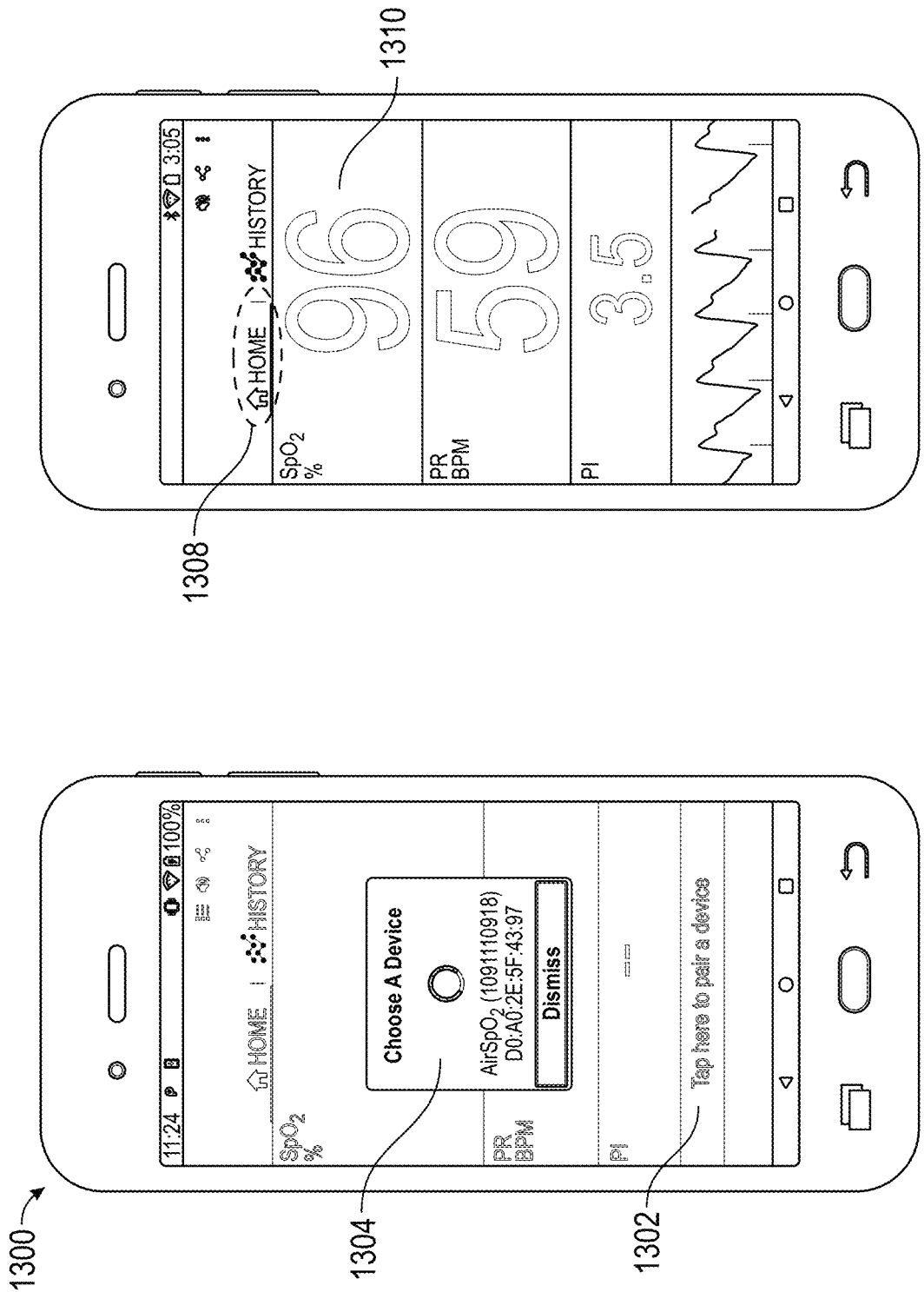

SYSTEM FOR TRANSMISSION OF SENSOR DATA USING DUAL COMMUNICATION PROTOCOL

RELATED APPLICATIONS

The present application is a continuation of U.S. patent application Ser. No. 16/599,017, filed Oct. 10, 2019, which claims priority from U.S. Provisional Patent Application No. 62/744,988, filed Oct. 12, 2018, entitled SYSTEM FOR TRANSMISSION OF SENSOR DATA USING DUAL COMMUNICATION PROTOCOL; all of which are incorporated by reference herein in their entirety.

FIELD OF THE DISCLOSURE

The present disclosure relates to physiological sensors and wireless pairing devices. More specifically, the present disclosure relates to collection of physiological data using physiological sensors and transmitting the data to nearby computing systems using a wireless pairing device.

BACKGROUND

Conventional physiological measurement systems are limited by the patient cable connection between sensor and monitor. A patient must be located in the immediate vicinity of the monitor. Also, patient relocation requires either disconnection of monitoring equipment and a corresponding loss of measurements or an awkward simultaneous movement of patient equipment and cables. Various devices have been proposed or implemented to provide wireless communication links between sensors and monitors, freeing patients from the patient cable tether.

SUMMARY

This disclosure describes, among other things, embodiments of systems, devices, and methods for collecting patient physiological data and transmitting the data to nearby computing systems via wireless transmission.

A sensor system is discloses that can include a disposable sensor usable to monitor a tissue of a patient and a reusable transmitter usable to wirelessly communicate with a patient monitor. The disposable sensor can include a sensor element and a battery to provide power for both the disposable sensor and the reusable transmitter. The sensor element can include one or more emitters and detectors. The reusable transmitter can include an antenna and one or more hardware processors.

A method of pairing a sensor with a computing device is disclosed. The method can include communicating pairing data between a transmitter and a computing device using a first communication protocol. The method can include receiving power from a battery included in a sensor package responsive to mating of the transmitter with the sensor package. The method can include connecting with the computing device based on the received airing data using a second communication protocol. The second communication protocol can be different than the first communication protocol. The method can further include transmitting sensor data to the computing device based on the second protocol connection.

A circuit for a disposable sensor for a system for pairing a noninvasive patient sensor with a computing device is disclosed. The circuit can include a body that can include one or more first electrical contacts. The circuit can include elongate members that include one or more second electrical contacts. The elongate members can extend from the body along a length of the body. The elongate members can be arcuate. The first electrical contacts and the second electrical contacts can be connected such that electrical signals can be transmitted between the first and the second electrical contacts. The first electrical contacts can be operatively connected to a sensor element and a battery of the disposable sensor.

A physiological sensor for a system for pairing a noninvasive patient sensor with a computing device is disclosed. The physiological sensor can include a sensor element. The physiological sensor can include a docking member. The docking member can include a docking surface and a retainer. The retainer can be hingedly coupled to the docking member. The physiological sensor can include a cable operatively coupled to the sensor element and the docking member. The cable can allow signals to be transmitted between the sensor element and the docking member. The retainer can engage a reusable transmitter to hold the reusable transmitter against the docking surface.

In some embodiments, a system for pairing a disposable noninvasive sensor assembly with a monitoring device using a reusable transmitter assembly is disclosed. The disposable noninvasive sensor assembly can collect physiological data of a patient. The system can include a disposable noninvasive sensor assembly and a reusable transmitter assembly. The disposable noninvasive sensor assembly can collect physiological data from a patient. The physiological data can be indicative of physiological condition of the patient. The disposable noninvasive sensor assembly can include a sensor element and a battery. The sensor element can be attached to the patient. The reusable transmitter assembly can receive the physiological data of the patient from the disposable noninvasive sensor assembly. The reusable transmitter assembly can include a processor and a wireless communication module can establish a wireless communication with a patient monitor.

The system of the preceding paragraph can include one or more of following features: The reusable transmitter assembly does not include a power source for providing power for the processor and the wireless communication module. The wireless communication module can include a first antenna. The wireless communication module can also include a second antenna. The reusable transmitter assembly can receive power from the battery of the disposable noninvasive sensor assembly. The reusable transmitter assembly can receive raw physiological data from the disposable noninvasive sensor assembly, and wherein the raw physiological data can be collected by the sensor element. The processor can process the raw physiological data transmitted to the reusable transmitter assembly and generate physiological parameters. The reusable transmitter assembly can transmit the physiological parameters to the patient monitor. The sensor element can include a detector and an emitter. The detector and the emitter can be optical based. The emitters can be light-emitting diodes (LEDs). The disposable noninvasive sensor assembly can be coupled to a patient. The reusable transmitter assembly can be removably coupled to the disposable noninvasive sensor assembly. The reusable transmitter assembly or the disposable noninvasive sensor assembly may be waterproof or shockproof. The wireless communication module can receive electronic data from or transmit electronic data to the patient monitor. The wireless communication module can use at least a first wireless communication protocol to associate the reusable transmitter assembly with the patient monitor, and wherein the wireless communication module can use at least a second wireless communication protocol to transmit data between the wireless communication module and the patient monitor. The first wireless communication protocol can be near-field communication (NFC). The second wireless communication protocol can be different from the first wireless communication protocol. The second wireless communication protocol can be Bluetooth®. The wireless communication between the reusable transmitter assembly and the patient monitor can be based at least on a pairing signal transmitted from the patient monitor to the reusable transmitter assembly and an identification information transmitted from the reusable transmitter assembly to the patient monitor. The patient monitor can transmit the pairing signal to the reusable transmitter assembly when the reusable transmitter assembly is brought within a predetermined distance from the patient monitor. The pairing signal and the identification information can be transmitted via the first wireless communication protocol. The identification information can be unique to the reusable transmitter assembly. The identification information can be an RFID tag associated with the reusable transmitter assembly. The identification information can be transmitted from the reusable transmitter assembly to the patient monitor in response of the transmission of the pairing signal from the patient monitor to the reusable transmitter assembly. The transmission of the identification information may occur automatically. The transmission of the identification information may not occur automatically. The disposable noninvasive sensor assembly can include a dock configured to mate with the reusable transmitter assembly. The dock can include arcuate supports and a flexible circuit comprising elongate members. The elongate members can be supported by the arcuate supports that push the elongate members of the flexible circuit against the reusable transmitter assembly when the reusable transmitter assembly is coupled to the dock of the disposable noninvasive sensor assembly. The flexible circuit can facilitate transmission electronic signals between the disposable noninvasive sensor assembly and the reusable transmitter assembly. The elongate members can include electrical contacts that come in contact with electrical contacts of the reusable transmitter assembly when the reusable transmitter assembly is coupled with the disposable noninvasive sensor assembly. The flexible circuit can be in contact with the battery such that the flexible circuit transmits power from the battery to the reusable transmitter assembly when the reusable transmitter assembly is coupled with the disposable noninvasive sensor assembly. The battery can generate power by reacting with oxygen in the air. The disposable noninvasive sensor assembly can include a housing storing the battery. The housing can include channels and openings, and wherein the channels can facilitate the air to enter into the housing via the openings. The openings may be formed on inner surfaces of the channels such that the openings are exposed to the air when the channels are covered. The channels can be defined on a top surface of the housing. The channels may extend to side edges of the housing. The disposable noninvasive sensor assembly can be removably attached to a patient. The disposable noninvasive sensor assembly can include elongate members that can wrap around a patient. The patient monitor can be a mobile device. The reusable transmitter assembly can be brought proximate to a specific location on the patient monitor to establish the wireless communication between the reusable transmitter assembly and the patient monitor. The patient monitor is a mobile device. The patient monitor can be a bedside patient monitor.

In some embodiments, a method of pairing a noninvasive sensor assembly with a patient monitor using a transmitter is disclosed. The noninvasive sensor assembly can collect physiological data from a patient and transmit the physiological data to the transmitter. The patient monitor can display parameters associated with the physiological data and indicative of physiological condition of the patient. The method can include: receiving, using a transmitter, a pairing signal from a patient monitor via a first wireless communication protocol; transmitting, using the transmitter, an identification information to the patient monitor via the first wireless communication protocol; establishing a wireless communication between the transmitter and the patient monitor based at least on the pairing signal and the identification information, the wireless communication based at least on a second wireless communication protocol; collecting raw physiological data of a patient using a sensor element of the noninvasive sensor assembly; processing, using a processor of the transmitter, the raw physiological data to generate physiological parameters; and transmitting the physiological parameters to the patient monitor via the wireless communication.

The method of preceding paragraph can include one or more of following features: The method can include generating power from the signal using the transmitter. The power can be used for transmission of the identification information. The first wireless communication protocol can be different from the second wireless communication protocol. The transmitter may not require a power source to receive the pairing signal. The transmitter may not include a power source. The method can include receiving power from a battery of the noninvasive sensor assembly. Collecting of the raw physiological data can include: generating an emitter signal using a processor of the noninvasive sensor assembly; transmitting the emitter signal to an emitter of the noninvasive sensor assembly; generating, using the emitter, an optical output based at least on the emitter signal; detecting the optical output using a detector; and converting the optical output to generate the raw physiological data. The transmitter can be reusable. The noninvasive sensor assembly can be disposable. The first wireless communication protocol can be near-field communication (NFC). The second communication protocol can be Bluetooth®. The identification information can be an RFID tag uniquely identifying the transmitter. The transmission of the identification information can occur automatically in response to receiving the pairing signal. Establishing the wireless communication between the transmitter and the patient monitor can include associating the transmitter with the patient monitor using at least in part the pairing signal and the identification information.

In some embodiments, a method of collecting patient physiological data using a noninvasive sensor system having a disposable sensor assembly and a reusable transmitter assembly is disclosed. The reusable transmitter assembly can wirelessly transmit the physiological data to a patient monitor. The method can include: establishing a first wireless communication between a reusable transmitter assembly and a patient monitor; transmitting, using the reusable transmitter, pairing parameters to the patient monitor via the first wireless communication; establishing a second wireless communication between the reusable transmitter and the patient monitor; coupling the reusable transmitter with a disposable sensor assembly; collecting raw physiological data using a sensor element of the disposable sensor assembly; and transmitting, using the reusable transmitter, physiological parameters to the patient monitor.

The method of the preceding paragraph can include one or more of following features: The first wireless communication can be different from the second wireless communication. The first wireless communication can be based on near-field communication (NFC) and the second wireless communication can be based on Bluetooth®. The reusable transmitter may not include a power source. Transmitting the pairing parameters can include: receiving a pairing signal from the patient monitor; and generating power from the pairing signal, the power used for transmitting the pairing parameters to the patient monitor. Transmitting the physiological parameters to the patient monitor can include receiving power from a battery of the disposable sensor assembly. The method can include processing the raw physiological data using a processor of the transmitter to generate physiological parameters. Collecting of the raw physiological data can include: generating an emitter signal; transmitting the emitter signal to an emitter of the disposable sensor assembly; generating, using the emitter, an optical output based at least on the emitter signal; detecting the optical output using a detector; and converting the optical output to generate the raw physiological data. The reusable transmitter can include an RFID tag uniquely identifying the reusable transmitter. The transmission of the pairing parameters can occur automatically after the reusable transmitter is brought within a predetermined distance of the patient monitor. Establishing the second wireless communication between the reusable transmitter and the patient monitor can include associating the reusable transmitter with the patient monitor using at least the pairing parameters. Establishing the first wireless communication between the reusable transmitter and the patient monitor can include bringing the reusable transmitter proximate to a specific location on the patient monitor. The patient monitor can be a mobile device. The patient monitor can be a bedside patient monitor.

In some embodiments, a method of collecting and displaying patient physiological data using a sensor system having a disposable sensor assembly and a reusable transmitter assembly is disclosed. The method can include: establishing a wireless communication between the reusable transmitter and the patient monitor; collecting raw physiological data using a sensor element of the disposable sensor assembly; transmitting, using the reusable transmitter, the raw physiological data to the patient monitor; processing the raw physiological data to determine physiological parameters using a processor of the patient monitor; and displaying, using a display of the patient monitor, the physiological parameters.

The method of the preceding paragraph can include one or more of following features: Establishing the wireless communication between the reusable transmitter assembly and the patient monitor can include: receiving, using the reusable transmitter assembly, pairing signal from the patient monitor; transmitting, using the reusable transmitter assembly, pairing parameters to the patient monitor; and associating the reusable transmitter assembly with the patient monitor using at least in part the pairing parameters. The pairing parameters can be transmitted using a first wireless protocol, and wherein the first wireless protocol can be near-field communication (NFC). The reusable transmitter assembly may not require a power source to receive the pairing signal. The reusable transmitter assembly can include a RFID tag that can include the pairing parameters. The transmission of the pairing parameters can occur automatically in response to the receipt of the pairing signal. The reusable transmitter assembly may not include a power source. The reusable transmitter assembly can receive power from a battery of the disposable sensor assembly. Collecting the raw physiological data can include: generating an emitter signal; transmitting the emitter signal to an emitter of the disposable sensor assembly; generating, using the emitter, an optical output based at least on the emitter signal; detecting the optical output using a detector; and converting the optical output to generate the raw physiological data. The wireless communication between the reusable transmitter assembly and the patient monitor can be based at least on Bluetooth®. Establishing the wireless communication between the transmitter and the patient monitor can include associating the reusable transmitter assembly with the patient monitor. Establishing the wireless communication between the reusable transmitter and the patient monitor can include bringing the reusable transmitter proximate to a specific location on the patient monitor.

In some embodiments, a flexible circuit for a disposable sensor assembly is disclosed. The disposable sensor assembly can collect physiological data of a patient and transmit the physiological data to a patient monitor via a transmitter assembly. The flexible circuit can include a body and elongate members. The body can include a first plurality of electrical contacts. The elongate members can include a second plurality of electrical contacts. The elongate members can extend from the body along a longitudinal axis of the body. The elongate members can be arcuate. The first plurality of electrical contacts can be operatively connected to a sensor element and a battery of the disposable sensor. The first electrical contacts and the second electrical contacts can be connected such that electrical signals can be transmitted between the first and the second electrical contacts.

The flexible circuit of the preceding paragraph can include one or more of following features: The elongate members can be flat. An interaction between tips of the elongate members and the disposable sensor can cause the elongate members to be arcuate. The second plurality of electrical contacts can be located at an apex of each of the elongate members when the elongate members are arcuate. The elongate members can be arcuate with a first degree of curvature when installed on the disposable sensor, and wherein the elongate members can be arcuate with a second degree of curvature when a reusable transmitter is mated with the disposable sensor. The second degree of curvature can be less than the first degree of curvature. The elongate members can have a first height when installed on the disposable sensor, and the elongate members can have a second height when a reusable transmitter is mated with the disposable sensor. The first height can be greater than the second height. The elongate members can be supported by a plurality of arcuate supports of the disposable sensor when installed on the disposable sensor.

In some embodiments, a pairing system for establishing a wireless communication between a transmitter assembly of a physiological sensor system and a patient monitor is disclosed. The patient monitor can display physiological parameters of a patient. The pairing system can include an adaptor, a housing, and a cable assembly. The adaptor can be coupled to a patient monitor. The housing can include a processor and a wireless communication interface. The processor can generate a pairing signal. The wireless communication interface can establish a wireless communication with a transmitter assembly and receive physiological parameters from the transmitter assembly. The physiological parameters can be based at least in part on physiological data collected by a disposable noninvasive physiological sensor removably coupled to the patient. The cable assembly can be coupled to the adaptor and the housing. The cable assembly can allow transmission of the physiological parameters the adaptor and the housing.

The pairing system of the preceding paragraph can include one or more of following features: The housing can be removably coupled to a body of the patient monitor. The processor can transmit the pairing signal to the transmitter assembly. The pairing signal can be used to establish the wireless communication between the wireless communication interface and the transmitter assembly. The pairing signal can be transmitted to the transmitter assembly when the transmitter assembly is proximate a specific location on the patient monitor. The housing can include an inset surface. The inset surface can indicate a location of the wireless communication interface. The wireless communication interface can establish a wireless communication with the transmitter assembly via a first wireless communication protocol. The first wireless communication protocol can be near-field communication (NFC). The wireless communication interface can wirelessly receive an identification information from the transmitter assembly. The identification information can be an RFID tag unique to the transmitter assembly. The wireless communication interface can wirelessly receive the identification information from the transmitter assembly in response to the transmission of the pairing signal. The processor of the housing can receive the identification information from the wireless communication interface and transmit the identification information to the patient monitor. The identification information can include pairing parameters unique to the transmitter assembly. The patient monitor can establish a wireless communication with the transmitter assembly based at least on the identification information of the transmitter assembly. The wireless communication between the patient monitor and the transmitter assembly can be based on Bluetooth®. The pairing system can receive power from the patient monitor via the adaptor and the cable assembly. The pairing signal can generate power for the transmitter assembly. The pairing signal can be transmitted to the transmitter assembly when the transmitter assembly is within a predetermined distance from the wireless communication interface or when the transmitter assembly contacts the housing. The wireless communication interface can receive physiological parameters from the transmitter assembly and transmit the physiological parameters to the patient monitor for display. The wireless communication interface can receive physiological parameters from the transmitter assembly using a wireless communication protocol different from one used for transmitting the pairing signal to the transmitter assembly. The adaptor can be plugged into a sensor input of the patient monitor. The pairing system can provide wireless communication capability for the patient monitor.

In some embodiments, an apparatus for storing a reusable wireless transmitter assembly is disclosed. The reusable wireless transmitter can receive patient physiological data from a disposable noninvasive sensor assembly and transmit the patient physiological data to a patient monitor via a wireless communication. The apparatus can include a base and a body. The base can be coupled to a housing of a patient monitor. The patient monitor can receive patient physiological parameters from a reusable wireless transmitter assembly. The body can include a support surface that can receive a corresponding mating surface of the reusable wireless transmitter assembly. The body can protrude out from the base in a direction orthogonal to the base. The body can include a magnet to retain the reusable wireless transmitter assembly. The support surface can be arcuate and perpendicular to the base.

The apparatus of the preceding paragraph can include one or more of following features: The base can include a magnet configured to retain the wireless transmitter. The magnet can be positioned about the support surface of the body. An outer surface of the body can be flush with an outer surface of the reusable wireless transmitter assembly when the reusable wireless transmitter assembly is coupled to the apparatus. A shape of the base can correspond to a shape of the reusable wireless transmitter assembly such that an outline of the base matches that of the reusable wireless transmitter assembly when the reusable wireless transmitter assembly is coupled to the apparatus.

In some embodiments, a method of coupling a wireless transmitter assembly with a noninvasive sensor assembly configured to collect physiological data from a patient is disclosed. The method can include: positioning a wireless transmitter assembly such that legs of the wireless transmitter assembly can be substantially aligned with and facing slots formed on a dock of a noninvasive sensor assembly, the slots can be dimensioned and shaped to receive the legs of the wireless transmitter assembly; pushing the wireless transmitter assembly towards the slots such that the legs can be positioned within the slots; and pressing down the wireless transmitter assembly to removably couple the wireless transmitter assembly with the dock of the noninvasive sensor assembly, thereby causing the wireless transmitter assembly to receive patient physiological data from the noninvasive sensor assembly and to transmit the patient physiological data to a proximate bedside patient monitor.

The method of the preceding paragraph can include one or more of following features: The sensor assembly can include a housing. The slots can be defined between the dock and the housing. The housing can include lips. Each of the lips can correspond to each of the slots of the dock. The legs of the wireless transmitter can be positioned under the lips of the housing. The dock can include a retainer that can hold the transmitter assembly within the dock. The retainer can be positioned opposite from the slots. Pressing down the transmitter assembly can cause the retainer to change from a first configuration to a second configuration, thereby allowing the transmitter assembly to be seated within the dock. The retainer can be substantially vertical with respect to the dock when in the first configuration, and the retainer can be bent in a direction away from the dock in the second configuration. The retainer can be in the first configuration when the transmitter assembly is coupled with the dock, and the retainer in the first configuration can hold the transmitter assembly within the dock.

In some embodiments, a system for collecting patient physiological parameters and transmitting the parameters to a mobile device is disclosed. The patient physiological parameters can be collected with a noninvasive sensor assembly. The parameters can be transmitted to the mobile device using a transmitter assembly. The system can include a noninvasive sensor assembly, a transmitter assembly, and a patient monitor. The noninvasive sensor assembly can include a sensor element and a battery in a first housing. The sensor element can collect physiological data from a patient. The transmitter assembly can include a processor and a wireless communication module in a second housing. The transmitter assembly can establish wireless communication with a patient monitor. The patient monitor can display physiological parameters and transmit the patient physiological parameters to a mobile device.

The system of the preceding paragraph can include one of more of following features: The sensor element can include an emitter and a detector. The emitter and the detector can be optical. The transmitter assembly may not include a power source for providing power for the processor and the wireless communication module. The transmitter assembly can be reusable. The noninvasive sensor assembly can be disposable. The transmitter assembly can receive power from the battery of the noninvasive sensor assembly. The reusable transmitter assembly can receive raw physiological data from the disposable sensor assembly. The raw physiological data may be collected by the sensor element. The noninvasive sensor assembly can be removably coupled to the patient. The noninvasive sensor assembly can be coupled to a wrist of the patient. The sensor element can be coupled to a fingertip of the patient. The first housing or the second housing can be waterproof or shockproof. The wireless communication module can use a first wireless communication protocol to associate the transmitter assembly with the patient monitor, and the wireless communication module can use a second wireless communication protocol to transmit data to the patient monitor. The processor of the transmitter assembly can receive the physiological data from the noninvasive sensor assembly and process the physiological data to generate the physiological parameters. The transmitter assembly can wirelessly transmit the physiological parameters to a mobile device. The patient monitor can wirelessly transmit the physiological parameters to a mobile device. The patient monitor can be Root® platform.

In some embodiments, a method transmitting physiological data from a noninvasive sensor assembly to a patient monitor using a wireless transmitter assembly is disclosed. The method can include: approximating a wireless transmitter assembly to a pairing device of a patient monitor to receive a pairing signal from the pairing device and transmit pairing parameters to the pairing device; and coupling the wireless transmitter assembly to a noninvasive sensor assembly to receive power from a battery of a noninvasive sensor assembly and receive physiological data from a sensor element of the noninvasive sensor assembly, wherein the wireless transmitter assembly can determine physiological parameters based at least in part on the physiological data and transmit the physiological parameters to the patient monitor.

The method of the preceding paragraph can include one or more of following features: The reception of the pairing signal and the transmission of the pairing parameters can be conducted via a first wireless communication protocol. The wireless transmitter assembly can transmit the physiological parameters to the patient monitor via a second wireless communication protocol. The first wireless communication protocol can be near-field communication (NFC). The second wireless communication protocol can Bluetooth®. The wireless transmitter assembly may not include a power source. The wireless transmitter can be reusable. The wireless transmitter assembly can be coupled to a dock of the noninvasive sensor assembly. The sensor element can include a detector and an emitter. The detector and the emitter can be optical. Coupling the wireless transmitter assembly automatically can cause the wireless transmitter assembly to determine physiological parameters and transmit the physiological parameters to the patient monitor.

In some embodiments, a flexible circuit for transmitting physiological data from a noninvasive sensor assembly to a transmitter assembly is disclosed. The transmission of the physiological data can occur when the transmitter assembly is coupled to the noninvasive sensor assembly. The flexible circuit can include a first plurality of electrical contacts, a second plurality of electrical contacts, a flexible body, and flexible elongate members. The first plurality of electrical contacts can receive physiological data from a sensor element of the noninvasive sensor assembly. The second plurality of electrical contacts can be in electronic communication with the first plurality of electrical contacts and can receive the physiological data from the first plurality of electrical contacts. The flexible elongate members can be coupled to the flexible body. Each of the elongate members can include a corresponding electrical contact of the second plurality of electrical contacts such that the second plurality of electrical contacts are in contact with the transmitter assembly when the transmitter assembly is coupled to the noninvasive sensor assembly.

The flexible circuit of the preceding paragraph can include one or more of following features: The flexible circuit can be coupled to the noninvasive sensor assembly. The flexible elongate members can be arcuate. Each of the flexible elongate members can have a first portion extending away and upwards with respect to a longitudinal axis of the body and a second portion extending away and downwards with respect to the longitudinal axis. The flexible elongate members can be supported on arcuate supports of the noninvasive sensor assembly. The arcuate supports can ensure contact between the flexible elongate members and the transmitter assembly when the transmitter assembly is coupled to the noninvasive sensor assembly. The sensor element of the noninvasive sensor assembly can include an emitter and a detector. The flexible elongate members of the flexible circuit can have a first configuration when the transmitter assembly is not coupled to the noninvasive sensor assembly and a second configuration when the transmitter assembly is coupled to the noninvasive sensor. The elongate members in the first configuration can be associated with a first degree of curvature and the elongate member in the second configuration can be associated with a second degree of curvature. The second degree of curvature can be less than the first degree of curvature. The flexible circuit can be coupled to a battery of the noninvasive sensor assembly such that the flexible circuit can receive power from a battery of the noninvasive sensor assembly and transmit the power to the transmitter assembly when the transmitter assembly is coupled to the dock.

In some embodiments, a wearable noninvasive sensor assembly for collecting physiological data from a patient is disclosed. The wearable noninvasive sensor assembly can include a dock, a transmitter assembly, and a sensor element. The dock can be coupled to a housing. The dock can include a retainer and an attachment mechanism. The transmitter assembly can be coupled to the dock. The sensor element can be coupled to the housing via a cable. The sensor element can collect physiological data from the patient. At least a portion of the cable can be positioned within the retainer.

The wearable noninvasive sensor assembly of the preceding paragraph can include one or more of following features: The attachment mechanism can include a plurality of straps that can wrap around the patient. The sensor element can include an emitter and a detector. The retainer can be coupled along a side of the dock and include a channel that can receive the cable. The retainer can limit the movement of the cable in at least a first direction while allowing movement in a second direction. The housing can house a battery that powers the sensor element. The battery can further power the transmitter assembly when the transmitter assembly is coupled to the dock. The wearable noninvasive sensor assembly can be coupled to the patient's wrist and the sensor element can be coupled to the patient's fingertip. The transmitter assembly can include a processor and a wireless communication module that can establish a wireless communication with a patient monitor. The wearable noninvasive sensor assembly can be waterproof or shockproof. The transmitter assembly can establish a wireless communication with a patient monitor, and the patient monitor can receive the physiological data from the transmitter assembly and display the physiological data on a display. The dock can include arcuate supports and a flexible circuit that can include elongate members supported by the arcuate supports. The arcuate supports can ensure contact between the elongate members of the flexible circuit and the transmitter assembly when the transmitter assembly is coupled to the dock. The dock can further comprises a flexible circuit. The flexible circuit can include elongate members. The elongate members can be flexible. The elongate members can be supported on arcuate supports of the dock, wherein the arcuate supports can ensure contact between the elongate members and the transmitter assembly when the transmitter assembly is coupled to the noninvasive sensor assembly. The elongate members can have a first configuration when the transmitter assembly is not coupled to the dock and a second configuration when the transmitter assembly is coupled to the dock. The elongate members in the first configuration can be associated with a first degree of curvature and the elongate member in the second configuration can be associated with a second degree of curvature. The second degree of curvature can be less than the first degree of curvature. The flexible circuit can be coupled to a battery of the noninvasive sensor assembly such that the flexible circuit receives power from a battery of the noninvasive sensor assembly and transmits the power to the transmitter assembly when the transmitter assembly is coupled to the dock.

In some embodiments, a system for collecting physiological data related to physiological conditions of a patient is disclosed. The physiological data can be collected using a disposable sensor assembly and a reusable transmitter assembly. A patient monitor can be used to display physiological parameters. The system can include a patient monitor, a disposable sensor assembly, and a reusable transmitter assembly. The patient monitor can include a display device. The disposable sensor assembly can include a battery, a sensor element, a housing, and a securement strap. The sensor element can collect physiological data from a patient. The disposable sensor assembly can include a flexible circuit having a plurality of electrical contacts. The securement strap can removably couple the disposable sensor assembly to the patient. The reusable transmitter assembly can include a processor and a wireless transmission module. The reusable transmitter assembly can receive the physiological data from the disposable sensor assembly. The processor can determine physiological parameters based at least in part on the physiological data. The wireless transmission module can establish a wireless communication with the patient monitor and transmit the physiological parameters of the patient to the patient monitor.

The system of the preceding paragraph can include one or more of following features: The patient monitor can include a communication module that can establish wireless communication with the reusable transmitter assembly. The sensor element can include an emitter and a detector. The battery can generate power by reacting with oxygen in the air. The sensor system can include channels and openings. The channels can be formed on a top surface of the housing and the openings can be formed on an inner surface of the channels. The channels and the openings can allow the air to enter into the housing and react with the battery. The reusable transmitter assembly may not include a power source for providing power for the processor and the wireless communication module. The reusable transmitter assembly can receive power from the battery of the disposable sensor assembly. The reusable transmitter assembly can be removably coupled to the dock of the disposable sensor assembly. The reusable transmitter assembly or the disposable sensor assembly can be waterproof or shockproof. The wireless communication module can use at least a first wireless communication protocol to associate the reusable transmitter assembly with the patient monitor. The wireless communication module can use at least a second wireless communication protocol to transmit data between the wireless communication module and the patient monitor. The first wireless communication protocol can be near-field communication (NFC). The second wireless communication protocol can be different from the first wireless communication protocol. The second wireless communication protocol can be Bluetooth®. The association between the reusable transmitter assembly and the patient monitors can be based at least on a pairing signal transmitted from the patient monitor to the reusable transmitter assembly and an identification information transmitted from the reusable transmitter assembly to the patient monitor. The patient monitor can transmit the pairing signal to the reusable transmitter assembly when the reusable transmitter assembly is brought within a predetermined distance from the patient monitor. The identification information can be transmitted from the reusable transmitter assembly to the patient monitor in response of the transmission of the pairing signal from the patient monitor to the reusable transmitter assembly. The transmission of the identification information can occur automatically. The transmission of the identification information may not occur automatically. The identification information can be an RFID unique to the reusable transmitter assembly. The patient monitor can retain the identification information of the reusable transmitter assembly and prevent other patient monitors from establishing wireless communication with the reusable transmitter assembly. The patient monitor can retain the identification information of the reusable transmitter assembly for a predetermined period of time when the wireless communication between the patient monitor and the reusable transmitter assembly is interrupted. The patient monitor can remove the identification information of the reusable transmitter assembly after the predetermined period of time. The patient monitor can reestablish the wireless communication with the reusable transmitter assembly using the identification information in response of the reusable transmitter being within a predetermined distance from the patient monitor. The flexible circuit can be configured to transmit the physiological data from the disposable sensor assembly to the reusable transmitter assembly. The dock can include arcuate supports and the flexible circuit comprises elongate members supported by the arcuate supports. The arcuate supports can push the elongate members of the flexible circuit against the reusable transmitter assembly when the reusable transmitter assembly is coupled to the dock of the disposable sensor assembly. The plurality of electrical contacts of the flexible circuit can come in contact with electrical contacts of the reusable transmitter assembly when the reusable transmitter assembly is coupled with the disposable sensor assembly. The flexible circuit can be in contact with the battery such that the flexible circuit can transmit power from the battery to the reusable transmitter assembly when the reusable transmitter assembly is coupled with the disposable sensor assembly. The patient monitor can be a bedside patient monitor. The patient monitor can be a mobile device. The patient monitor can monitor the strength of wireless signals via the wireless communication between the patient monitor and the reusable transmitter assembly. The patient monitor can generate a notification that the wireless signals is weak when the strength of the wireless signals is below a predetermined signal strength threshold. The patient monitor can monitor a charge level of the battery. The patient monitor can generate a notification that the charge level is low when the charge level of the battery is below a predetermined charge threshold.

For purposes of summarizing the disclosure, certain aspects, advantages, and novel features have been described herein. Of course, it is to be understood that not necessarily all such aspects, advantages, or features will be embodied in any particular embodiment.

BRIEF DESCRIPTION OF THE DRAWINGS

FIGS. 6C and 6D illustrate sides views of the flex circuit of FIG. 6A, showing a change of a configuration of the flex circuit.

FIGS. 9A-9C illustrate a reusable module and a computing device coupled to a dongle, providing additional details for a method of pairing the reusable module with the computing device.

FIG. 13A illustrates a mobile application for establishing a wireless communication with a reusable module.

FIGS. 13B-13E illustrate various views of the mobile application of FIG. 13A displaying patient parameters in various display formats.

DETAILED DESCRIPTION

Introduction

Figure 1:
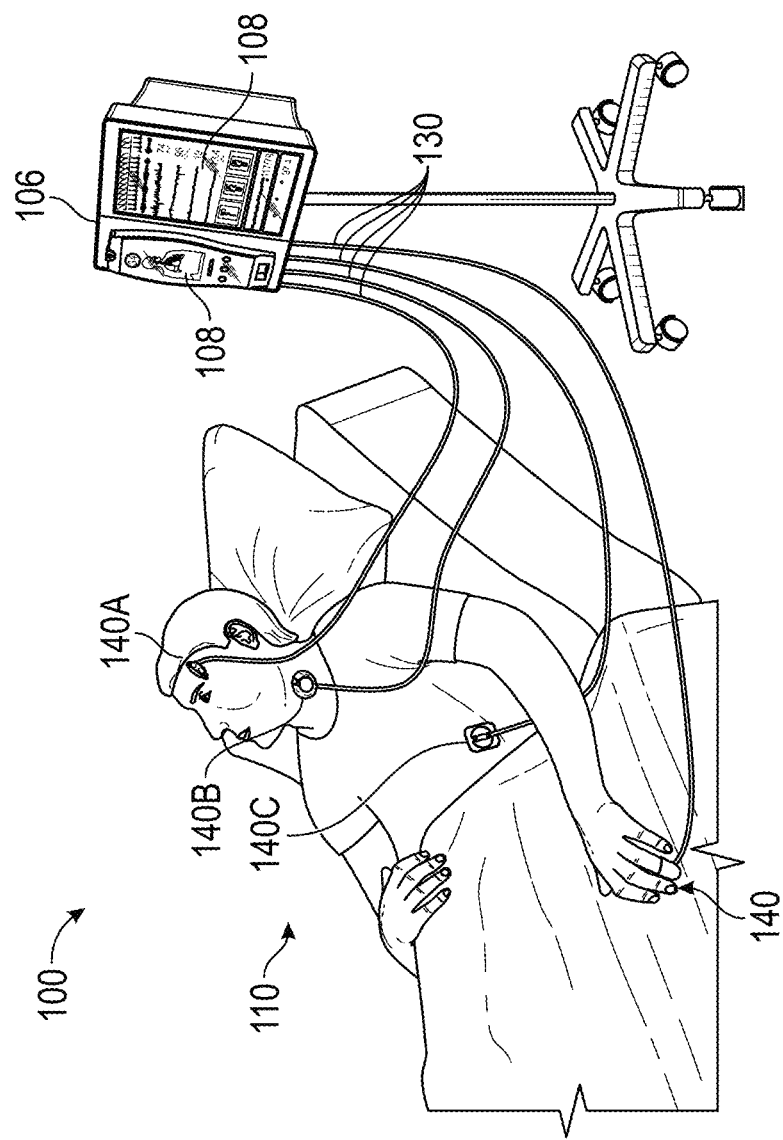
FIG. 1 illustrates an embodiment of a sensor system including sensors attached to a patient and transmitting patient physiological data to a computing device via cable.

Wired solution for sensors may be cumbersome and difficult to manage when there are multiple sensors attached to a patient as shown in FIG. 1. For example, the cable for the sensors can be tangled and damaged after repeated use. Moreover, since the sensors are tethered to a patient health monitor, patients have to be located proximate to the health monitor and movement of the patients can be limited. If a longer cable is required, the sensor and the cable have to be replaced together. Similarly, the sensors being tethered to the monitor can make transportation of the patient very difficult as it would require the patient to remain close to the monitor during transportation or disconnecting the sensors which would result in loss of measurements.

Overview

FIG. 1 illustrates an example of a sensor system 100 including a computing device 106 coupled sensors 140A, 140B, 140C, 140D via a cable 130, where the sensors are attached to a patient 110. The computing system 106 can include a display 108 that can display various physiological parameters. The sensors 140A, 140B, 140C, 140D can collect various types of physiological data from the patient 110 and transmit the data to the computing system 106 via the cable 130. Some example of the sensors 140A, 140B, 140C, 140D include, but not limited to, a rainbow acoustic monitoring sensor (RAM), O3 Regional Oximetry sensor, SpO2 sensor, a blood pressure sensor, an ECG sensor, and the like.

However, the cables 130 can be cumbersome to the patient and prone to tangling. The cables 130 can develop kinks and be damaged over time. In addition, because the sensors 140A, 140B, 140C, 140D are connected to the computing system 106 via the cables 130, location of the computing system 106 can be restricted to the lengths of the cables 130 attached to the sensors 140A, 140B, 140C, 140D. The cables 130 can also restrict patient movements. Therefore, a wireless solution including wireless communication capacity between the sensors and the computing device may resolve some of the concerns of the wired configuration. The wireless configuration can eliminate the need of the cables 130 between the sensors and the computing device and thus provide greater patient mobility.

However, the wireless solutions may have their own limitations. For example, wireless patient monitoring sensors require internal power source (for example, battery), which can have limited capacity due to size of the sensors. In addition, since continuous data collection and wireless transmission can require significant power usage, operation of the sensors can be very limited. Moreover, it may be expensive to replace the entire device when the internal battery is depleted. Furthermore, having a rechargeable battery may not be suitable in a hospital environment where nurses might not have enough time to wait for the battery to recharge. Also, it may not be ideal for a patient to wait for the battery to recharge in time of need. Accordingly, it can be advantageous to provide a sensor system that is compatible with existing sensors and monitors and is capable of wireless communication as discussed herein.

Figure 2A:
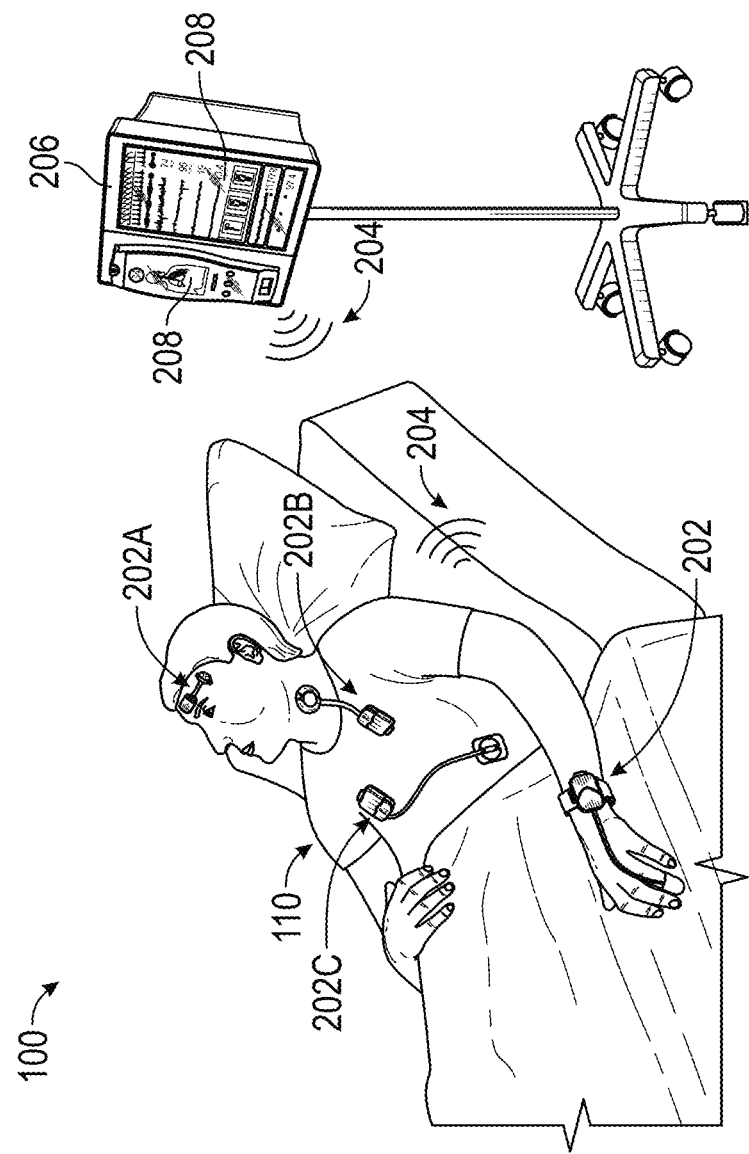
FIG. 2A illustrates another embodiment of a sensor system including sensor assemblies collecting and wirelessly transmitting patient physiological data to a computing device.

FIG. 2A illustrates the sensor system 100 including a computing device 206 wirelessly receiving patient physiological data of the patient 110 from sensor assemblies 202A, 202B, 202C, 202D. The sensor assemblies 202A, 202B, 202C, 202D can establish communication with the computing device 206 such that data can be wirelessly transmitted between the sensor assemblies 202A, 202B, 202C, 202D and the computing device 206. The computing device 206 can include a display 208 that can display patient parameters determined from the patient physiological data received from the sensor assemblies 202A, 202B, 202C, and 202D.

Figure 2B:
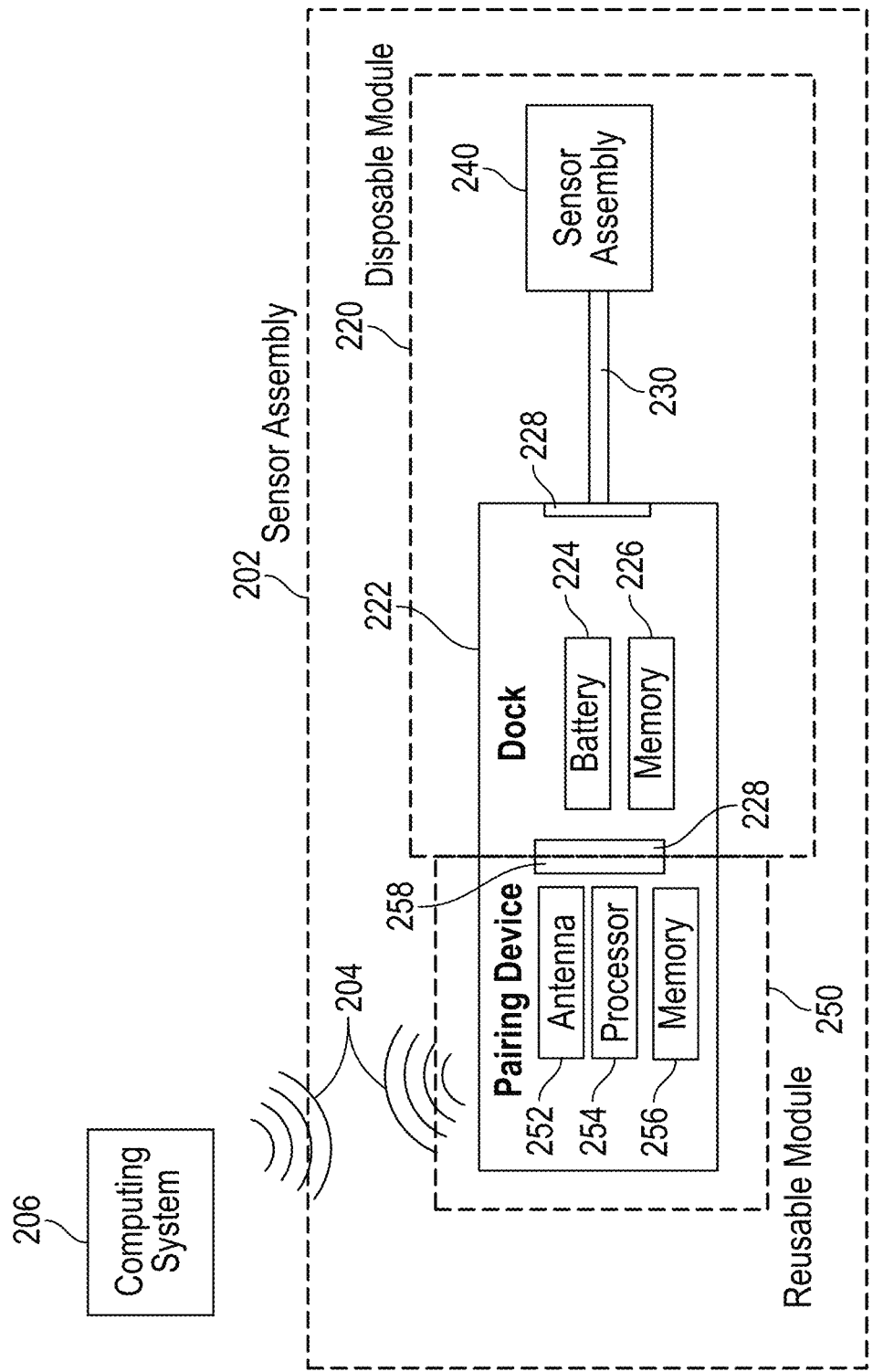
FIG. 2B illustrates a schematic diagram of an embodiment of a sensor assembly and a computing device, showing additional details of the sensor assembly.

FIG. 2B illustrates a schematic diagram the sensor assembly 202 wirelessly connected to a computing device 206. The sensor assembly 202 can include a disposable module 220 and a reusable module 250. The reusable module 250 can be a pairing device capable of establishing wireless connection with the computing device 206.

The disposable module 220 can include a dock 222 coupled to a sensor 240 via a cable 230. The dock 222 can be removably connected to the reusable module 250. The reusable module 250 and the computing device 206 can together establish a wireless communication 204 and perform wireless transmission of data between. The reusable module 250 can transmit patient physiological parameters to the computing device 206, where the parameters are calculated from raw physiological data collected by the sensor 240. The transmitted patient data can be raw data collected by the sensor 240.

The reusable module 250 alone or in combination with the dock 222 can perform signal processing on the raw physiological data and transmit the processed physiological data to the computing device 206. The reusable module 250 can establish wireless communication 204 with the computing device 206 to allow data be transmitted between the reusable module 250 and the computing device 206. The reusable module 250 can establish wireless communication 204 with one or more computing devices 206. As shown in FIG. 2A, the computing device 206 can establish wireless communication 204 with the sensor assemblies 202A, 202B, 202C, and 202D. The computing device 206 can establish wireless communication 204 with less than four or more than four sensor assemblies 202.

The reusable module 250 can establish wireless communication 204 with portable mobile devices such as mobile phone, smartphone, tablets, and the like. The computing device 206 can be a hospital patient monitoring system, which includes various types of monitors capable of displaying patient health data. The computing device 206 can be a mobile monitoring system or a personal mobile device. The computing device 206 can be Root® Platform, a patient monitoring and connectivity platform available at Masimo Corporation, Irvine, CA A mobile physiological parameter monitoring system usable with the cable is described in U.S. Pat. No. 9,436,645, issued on Sep. 6, 2016, titled "MEDICAL MONITORING HUB," the disclosure of which is hereby incorporated by reference in its entirety.

The cable 230 can be flexible or non-flexible. The cable 230 can be a thin film including electrical circuitries. The cable 230 can be surrounded by different types of electrical insulating material. The cable 230 can be substantially flat or round.

The sensor 240 can be an acoustic sensor, ECG sensor, EEG sensor, SpO2 sensor, or any other types of patient monitoring sensors. The sensor 240 can include one or more emitters and detectors. The emitters can be low-power, high-brightness LEDs (light-emitting diodes) to increase the life of the batteries 224. The sensor 240 can measure raw physiological data responsive to various types of patient physiological parameters including, but not limited to, temperature, blood pressure, blood oxygen saturation, hemoglobin level, electrocardiogram, and the like. The sensor measurements can be used by physicians to determine patient conditions and treatment for the patient. The sensor 240 can transmit the raw physiological data to the dock 222 via the cable 230. The sensor 240 and the dock 222 may form a unitary body such that the dock 222 receives the physiological data directly from the sensor 240 without the cable 230. The dock 222 can be integrated with one or more of the sensors 340.

The sensor 240 can output a raw sensor signal or a conditioned sensor signal. The sensor 240 can include a signal processor that can process the raw or conditioned sensor signal to derive and calculate physiological parameters associated with the raw or conditioned sensor signal.

The sensor 240 can perform mixed analog and digital pre-processing of an analog sensor signal to generate a digital output signal. As discussed above, the sensor 240 can include a signal processor that can perform digital post-processing of the front-end processor output. The input sensor signal and the output conditioned signal may be either analog or digital. The front-end processing may be purely analog or purely digital. The back-end processing may be purely analog or mixed analog or digital.

The sensor 240 can include an encoder, which translates a digital word or serial bit stream, for example, into a baseband signal. The baseband signal can include the symbol stream that drives the transmit signal modulation, and may be a single signal or multiple related signal components. The encoder can include data compression and redundancy.

The sensor 240 can include a signal processor, an encoder, and a controller. The sensor 240 can utilize emitters 242 and the detectors 244 to generate sensor signals, such as a plethysmograph signal. The signal processor then can use the sensor signal to derive a parameter signal that can include a real time measurement of oxygen saturation and pulse rate. The parameter signal may include other parameters, such as measurements of perfusion index and signal quality. The signal processor can be an MS-5 or MS-7 board available from Masimo Corporation, Irvine, CA The signal processing step can be performed by the processor 254 of the reusable module 250, as described above.

The dock 222 can be placed on various locations of a patient's body. For example, the dock 222 is placed on the patient's chest. The dock 222 can be placed on other locations on the patient including, but not limited to, torso, back, shoulder, arms, legs, neck, or head. Various means can be used to affix the dock 222 to the patient. For example, the dock 222 is affixed to the patient with an adhesive. In another example, the dock 222 is affixed to the patient with a fastener, such as tape, laid over at least a portion of the dock 222. The dock 222 can be mechanically attachable to at least one strap, which can wrap around the patient.

The reusable module 250 can receive physiological data from the sensor 240 via the dock 222. The reusable module 250 can wirelessly transmit the physiological data to the computing device 206. The reusable module 240 can couple with the dock 222 to establish an electronic communication between the reusable module 250 and the dock 222. The electrical communication between the dock 222 and the reusable module 250 can allow physiological data to be transmitted from the dock 222 to the pairing device 250. The coupling between the reusable module 250 and the dock 222 can be waterproof or shockproof. The disposable module 220 and the reusable module 250 may be shockproof or waterproof. The disposable module 220 and the reusable module 250 can be durable under various types of environments. For example, the reusable module 250 can be fully enclosed, allowing it to be washed, sanitized, and reused.

As shown in FIG. 2B, the dock 222 can include a memory 226 and battery 224. The reusable module 250 can include an antenna 252, a processor 254, and a memory 256. The antenna 252, the processor 254, and the memory 256 can be operatively connected with one another to allow electronic communication or transmission between them.

The antenna 252 can be an RFID (radio-frequency identification) antenna. The antenna 252 can be a Bluetooth® antenna. The reusable module 250 can include one or more antennae 252. In some aspects, the reusable module 250 includes a first antenna and a second antenna, where first antenna is a receiving antenna and the second antenna is a transmitting antenna. The first antenna can be a transmitting antenna and the second antenna can be a receiving antenna. Both the first antenna and the second antenna can both receive data from or transmit data to the computing device 206. The first antenna can be a passive antenna while the second antenna can be an active antenna. The first antenna can be an active antenna while the second antenna can be a passive antenna. An active antenna can include a built-in amplifier that can amplify certain spectrum or frequency of signals. The first antenna can establish an RFID or NFC (near field communication) connection with the computing device 206 while the second antenna can establish a Bluetooth® connection with the computing device 206. In another aspect, both the first and the second antenna are capable of establishing RFID and/or Bluetooth® wireless connection. The process of establishing wireless communication 204 with the computing device 206 and wirelessly transmitting the patient physiological data to the computing device 206 will be further described below in detail.

The memory 256 can be computer hardware integrated circuits that store information for immediate use for a computer (for example, the processor 254). The memory 256 can store the patient physiological data received from the sensor 240. The memory 256 can be volatile memory. For example, the memory 256 is a dynamic random access memory (DRAM) or a static random access memory (SRAM). The memory 256 can be a non-volatile memory. For example, the memory 256 is a flash memory, ROM (read-only memory), PROM (programmable read-only memory), EPROM (erasable programmable read-only memory), and/or EEPROM (electrically erasable programmable read-only memory).

The memory 256 of the reusable module 250 can store patient physiological data received from the sensor 240. The memory 256 can store electronic instructions that, when accessed, prompts the processor 254 to receive patient physiological data from the memory 226 of the dock 222, store the data in the memory 256, retrieve the data from the memory 256, transmit the data to the antenna 252, and use the antenna 252 to wirelessly transmit the data to the computing device 206. One or more of the actions discussed above can be performed simultaneously. For example, the processor 254 of the reusable module 250 can receive patient physiological data from the memory 226 of the dock 222 and simultaneously store the data in the memory 256.

The memory 256 can store patient data and health-related events related to a patient when the sensor assembly 202 is no longer in range with or is otherwise unable to communicate with the computing system 206. The memory 256, as noted above, can have sufficient capacity to store patient health data and/or health-related events. The memory 256 can store patient physiological information regardless of whether the reusable module 250 is paired with the computing device 206. Some examples of the health-related events include arrhythmia, low blood pressure, blood oxygen level (SpO2), and the like. Such data and/or health-related events may be accessed via a mobile application on a mobile device (for example, a smartphone, tablet, and the like). Patient data and/or health-related events can be relayed to a device without a display. In such circumstances, the device can have a light source (for example, an LED) that can blink in different colors or patterns to tell the patients or medical personnel something has happened or the data needs to be reviewed. Different rules can be used to determine when or in what situations can patient physiological information be transmitted from the sensor assembly 202 to other external devices (for example, monitoring devices, mobile devices, and the like). In order to maximize the life of the memory 256, the memory 256 may only store health-related event data. For example, this data can be as simple as a time stamp when an event occurred or it can be a snapshot of data taken just before and just after an event. The memory can also store large sections of data. The memory 256 can store up to 96 hours or more of data.

In some aspects, the data stored in the memory 256 can be transmitted to an outside server. The memory 256 can transfer the entire patient physiological information to the outside server or transmit only certain portions of the information. For example, the memory 256 can transmit timestamp information and associated event information to the external server. In another example, the memory 256 can transmit a snapshot of patient physiological information.

The processor 254 can be a chip, an expansion card/board, or a stand-alone device that interfaces with peripheral devices. For example, the processor 254 is a single integrated circuit on a circuit board for the reusable module 250. The processor 254 can be a hardware device or a software program that manages or directs the flow of data.

The processor 254 can communicate with the antenna 252 and the memory 256 of the reusable module 250. For example, the processor 254 communicates with the antenna 252 and the memory 256 of the reusable module 250 to retrieve or receive patient physiological data and to transmit the data to external devices via the antenna 252. The processor 254 can be a Bluetooth® chipset. For example, the processor 254 is a SimpleLink™ Bluetooth® low energy wireless MCU (microcontroller unit) by Texas Instruments Incorporated.

The processor 254 of the reusable module 250 can be connected to the sensor 240 such that it receives patient physiological data from the sensor 240 when the reusable module 250 is mated with the dock 222. The processor 254 can retrieve the patient physiological data from the memory 226 of the dock 222 and transmit the data to the antenna 252. The processor 254 can be operatively connected to the antenna 252 such that the processor 254 can use the antenna 252 to wirelessly transmit the patient physiological parameters to the computing device 206. The patient physiological data transmitted from the reusable module 250 to the computing device 206 can be raw patient physiological data in analog format (for example, 1131001310113100) or patient physiological parameters in a digital format (for example, 60% SpO2).

The sensor 240 can transmit raw or analog patient physiological data to the processor 254 of the reusable module 250. The processor 254 can then perform signal processing on the raw data to calculate patient physiological parameters. It can be advantageous to have the processor 254 to perform signal processing on the raw patient physiological data instead of having the computing device 206 perform signal processing on the raw data. Raw data can comprise strings of binary bits, whereas processed data can comprise digital (not binary) data (for example, 36 degrees Celsius, 72 beats per minute, or 96% blood oxygen level). Therefore transmitting digital data can require less power consumption than transmitting raw data. Thus, by performing signal processing on the raw data using the processor 254 and transmitting the processed data (as opposed to raw data) to the computing device 206, life of the battery 224 can be extended.

The battery 224 of the dock 222 can provide power for the sensor 240. Additionally, the battery 224 can provide power for the reusable module 250. In some aspects, the reusable module 250 may not have an internal power source to transmit patient data to the computing device 206. When the reusable module 250 is mated with the dock 222, the processor 254 of the reusable module 250 can draw power from the battery 224. The processor 254 can use the power from the battery 224 to process patient physiological data from the sensor 240 and to wirelessly transmit the data to the computing device 206. The battery 224 may or may not be rechargeable. The battery 224 can have wireless charging capacity.

Figure 2C:
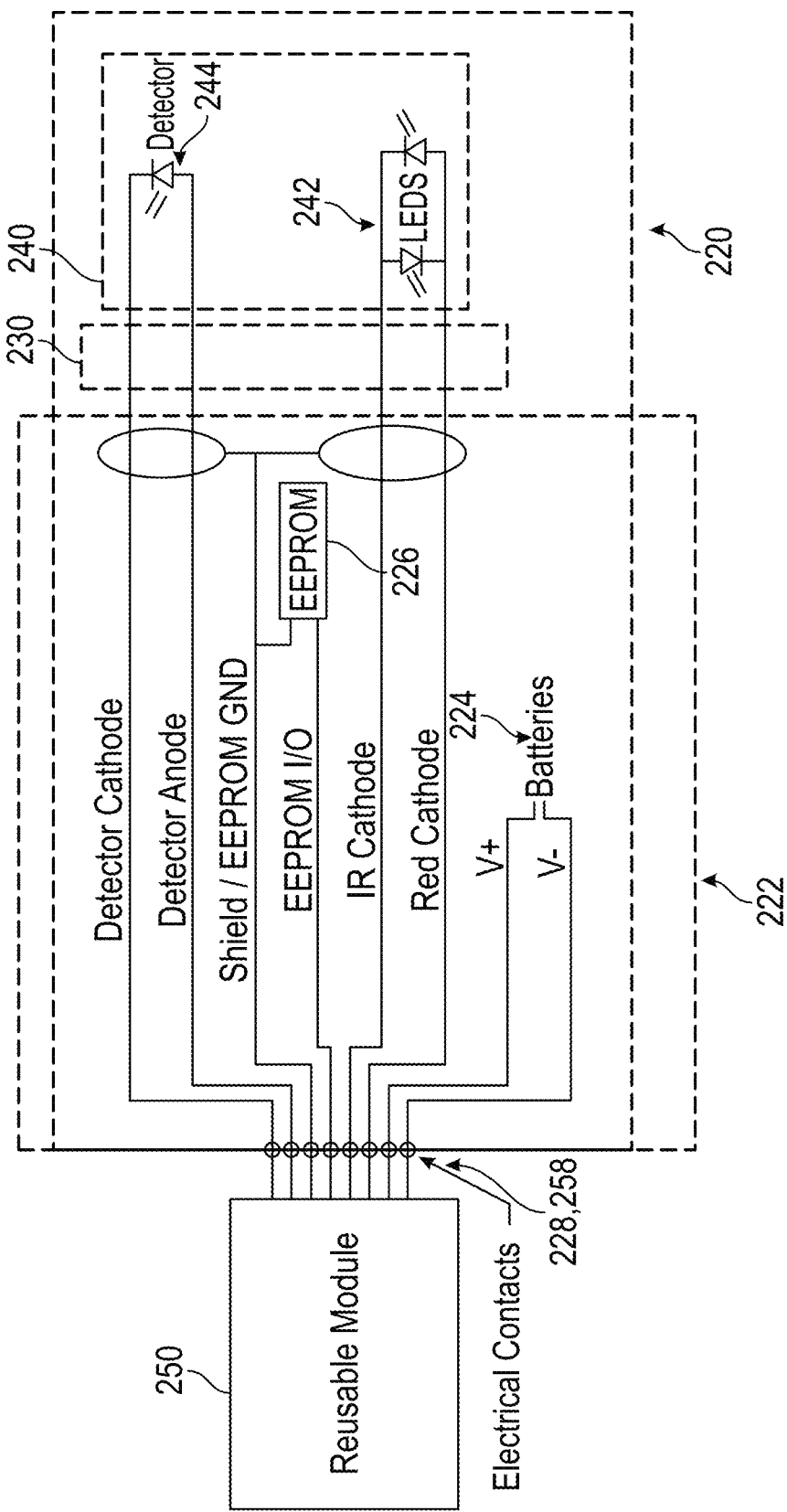
FIG. 2C illustrates a wiring diagram of an embodiment of a sensor assembly.

FIG. 2C illustrates a wiring diagram for the sensor system 202. The sensor 240 can include one or more detectors 244 and one or more emitters 242. The detectors 244 and the emitters 242 can be optical. The emitters 242 can be LEDs. The detectors 244 can detect light generated by the emitters 242. The emitters 242 and the detectors 244 are used to collect different types of patient physiological data, such as blood oxygen level, heart rate, and respiratory rate. As discussed below, the sensor 240 can include one of the following sensor elements including, but not limited to, piezoelectric elements for acoustic sensors, electrodes for EEG sensors, electrodes for ECG sensors, and the like.

The dock 222 and the reusable module 250 can include one or more electrical contacts 228 and electrical contacts 258, respectively. The electrical contacts 228 and 258 can establish electronic communication between the dock 222 and the reusable module 250 when the reusable module 250 is mated with the dock 222. The electrical communication between the electrical contacts 228 and 258 can allow the reusable module 250 to receive power from the battery 224 of the disposable module 220. Additionally and/or alternatively, the electrical connection between the electrical contacts 228 and 258 can allow the reusable module 250 to receive patient physiological data from the memory 226 of the dock 222. The coupling of the reusable module 250 and the dock 222 will be further described below.

Sensor Assembly

Figure 3A:
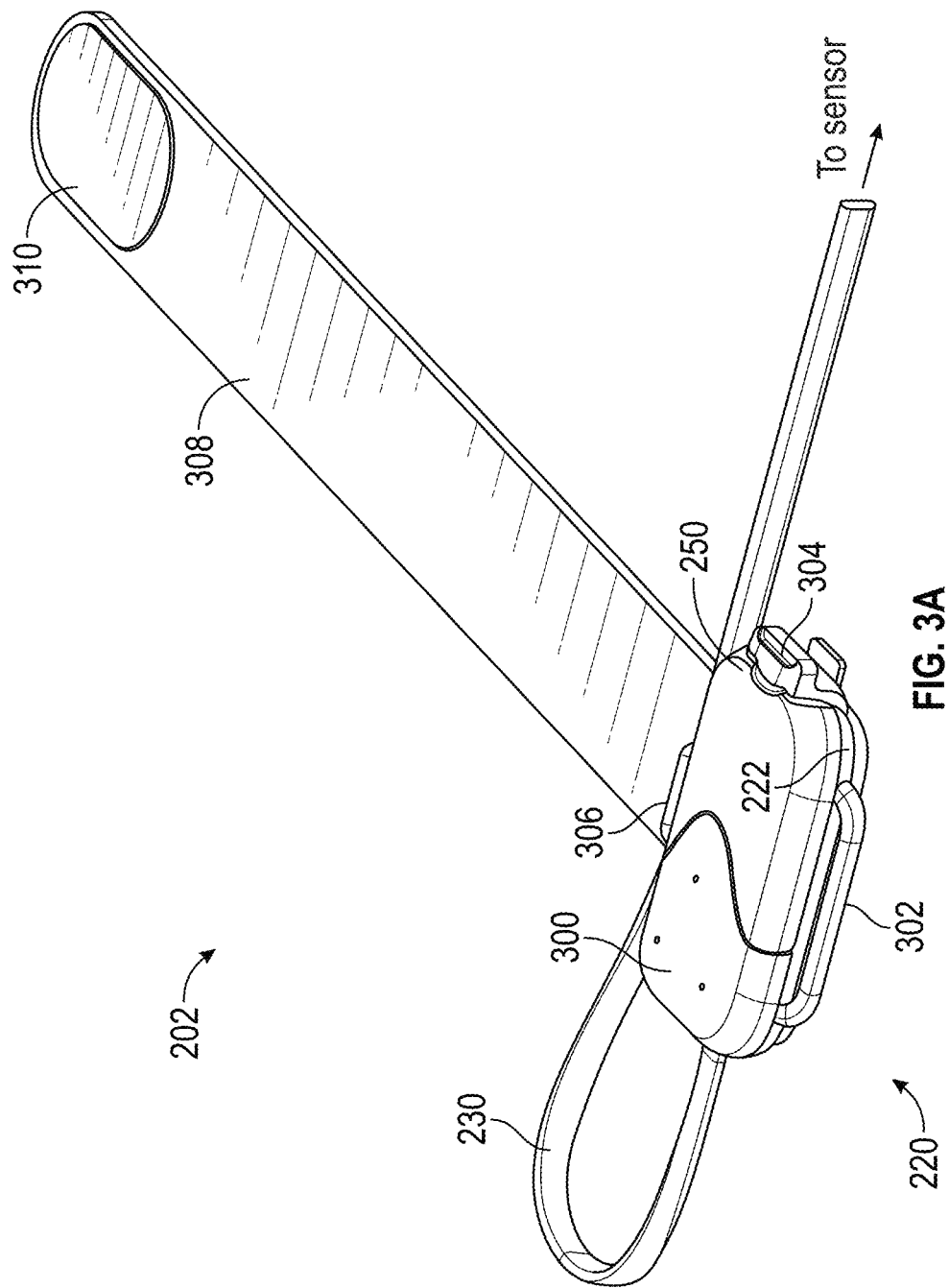
FIG. 3A illustrates a perspective view of an embodiment of a sensor assembly for collecting and wirelessly transmitting patient physiological data to a computing device.

FIG. 3A shows a front perspective view of an example of the sensor assembly 202 including the reusable module 250 and the disposable module 220. As discussed above, the reusable module 250 can be a pairing device that can establish wireless connection with the computing device 206. The disposable device 220 can include the dock 222 and the cable 230 coupling the dock 222 to the sensor 240 (not shown).

The dock 222 can include a strap 308 that is coupled to a bottom portion of the dock 222. The strap 308 can loop around a patient (e.g., a wrist or an arm) to removably attach the dock 222 to the patient (see FIG. 7H). The dock 222 can also include a strap loop 302 having a slot for the strap 308 to extend through. The strap 308 can extend through the strap loop 302 and loop around to removably attach the dock 222 to the patient. The strap 308 can include a fastener 310 disposed near a distal end of the strap 308 that can interact with the strap 308 to fix the distal end of the strap 308. The fastener 310 can be located at a distal end of the strap 308, as shown in FIG. 3A. The fastener 310 can be located at other locations of the strap 308. The dock can also include a retainer 304 that holds the reusable module 250 within the dock 222 to maintain electrical connection between the reusable module 250 and the dock 222. Moreover, the dock 222 can include a housing 300 that can house the battery 224 and the memory 226.

The dock 222 can include a cable retainer 306 disposed on a side of the dock 222. The cable retainer 306 can be dimensioned and sized to retain the cable 230. The cable retainer 306 can be removably connected to the dock 222. At least a portion of the cable retainer 306 may be flexible to facilitate insertion of the cable 230 into the cable retainer 306. The cable retainer 306 can advantageously limit movement of the cable 230 to prevent possible tangling of cables of different sensor assemblies. The cable retainer 306 can include a channel to through which the cable 230 can extend. The channel of the cable retainer 306 can be dimensioned such that the cable 230 is snug within the channel, thereby limiting movement of the cable 230.

Figure 3B:
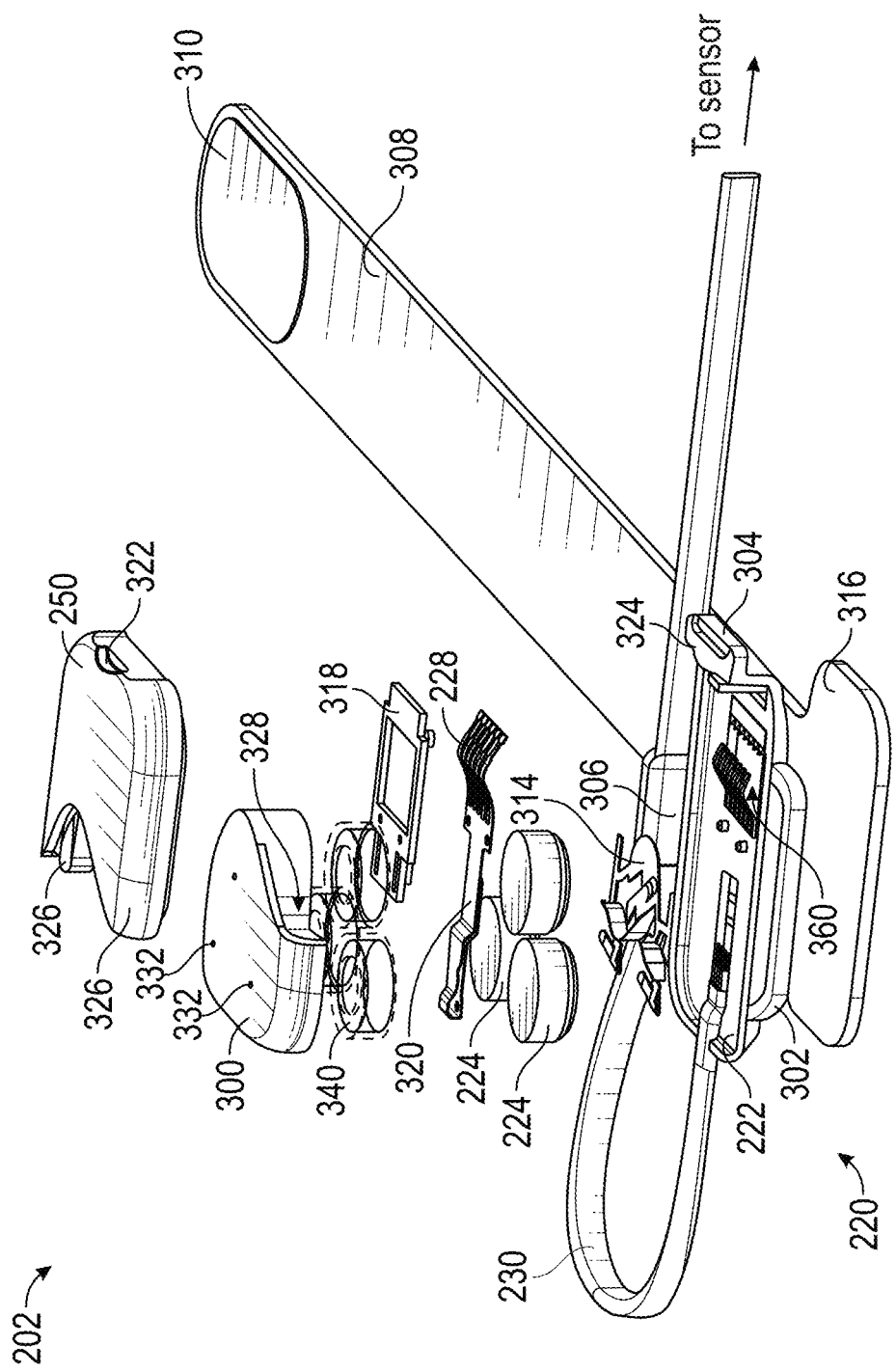
FIG. 3B illustrates an exploded, top perspective view of the sensor assembly of FIG. 3A.
Figure 3C:
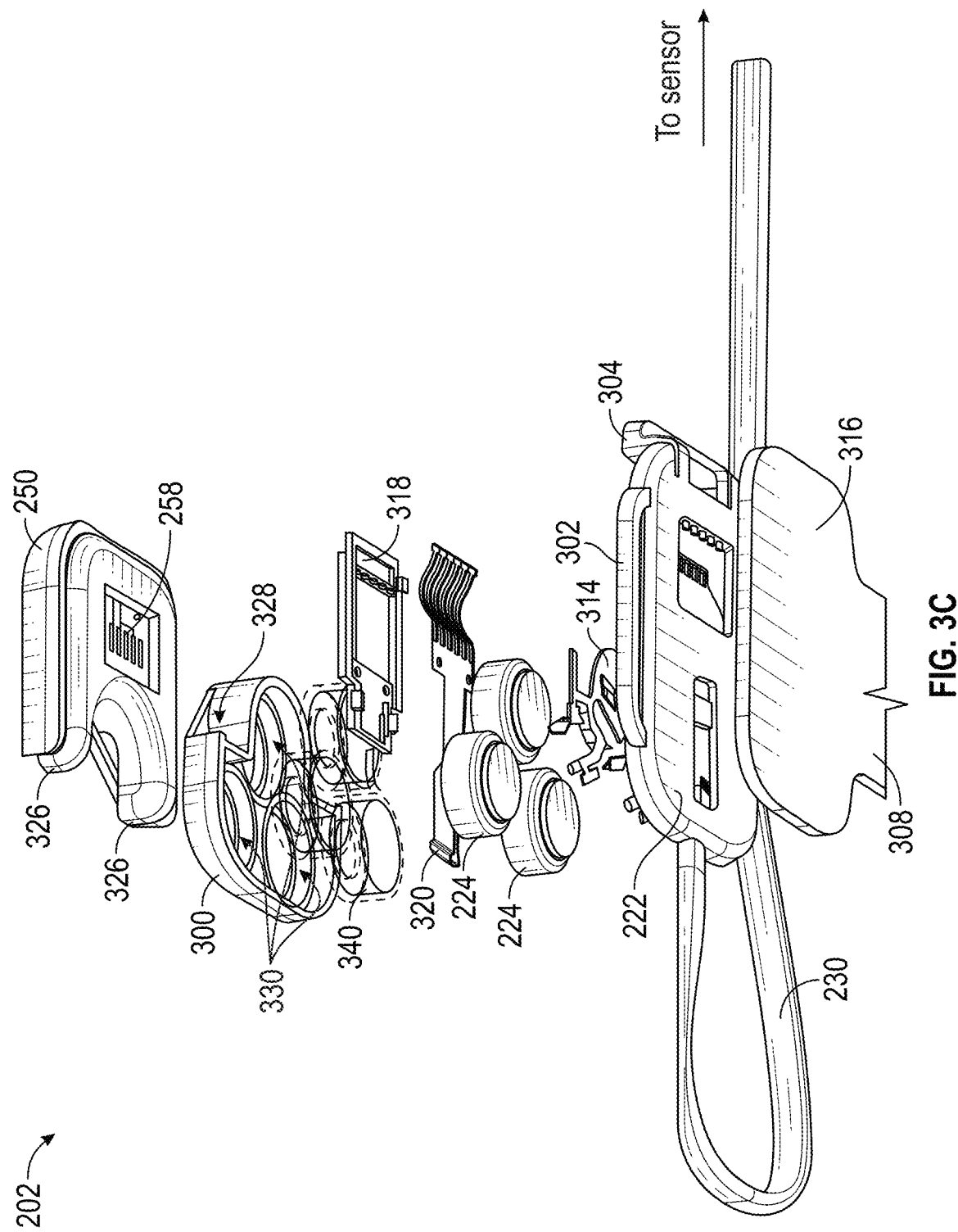
FIG. 3C illustrates an exploded, bottom perspective view of the sensor assembly of FIG. 3A.

FIG. 3B illustrates an exploded, top perspective view of the sensor assembly 202 of FIG. 3A. FIG. 3C illustrates an exploded, bottom perspective view of the sensor assembly 202 of FIG. 3A. The dock 222 of the disposable module 220 can include a support plate 316 disposed under the dock 222. The support plate 316 can be integrated with the strap 308. The strap 308 can be modular with respect to the support plate 316 and/or the dock 222. The dock 222 may not include the support plate 316 such that the strap 308 is coupled directly to the dock 222.

The retainer 304 of the dock 222 can include a protrusion 324 that can interact with a groove 322 of the reusable module 250. The interaction between the groove 322 and the protrusion 324 can maintaining coupling between the reusable module 250 and the dock 222. For example, when the reusable module 250 is inserted into the dock 222, the retainer 304 is pushed in a direction away from the housing 300 of the dock 222 in order to allow the reusable module 250 to mate with the dock 222. When the reusable module 250 is fully inserted into the dock 222, the retainer 304 can snap back to its original position to engage the groove 322 of the reusable module 250. The retainer 304 and the groove 322 can together prevent vertical displacement of the reusable module 250.

The retainer 304 can have a first position and a second position. When in the first position, the retainer 304 is substantially vertical with respect to the dock 222. When in the second position, the retainer 304 is pushed in a direction away from the housing 300 so that the retainer 304 forms an angle greater than 90 degrees with respect to the dock 222. Before the reusable module 250 is inserted into the dock 222, the retainer 304 can be in the first position. While the reusable module 250 is being pushed into the dock 220, the reusable module 250 interacts with the retainer 304 and causes the retainer 304 to be in the second position. When the reusable module 250 is fully engaged with the dock 222, the retainer 304 reverts to the first position so that the protrusion 324 engages the groove 322.

The dock 222 can also include a flex circuit 320 and a cover 318 to retain the flex circuit 320. The flex circuit 320 can include the electrical contacts 228 of the dock 222, where the flex circuit 320 serves as a connection between the cable 230 and the electrical contact 228. Therefore any information or data transmitted from the sensor 240 via the cable 230 to the dock 222 can be transmitted to the electrical contacts 228 via the flex circuit 320. Additional details of the flex circuit 320 will be provided below.

The housing 300 of the dock 222 can include one or more slots 328 that can interact with one or more legs 326 of the reusable module 250. The slots 328 can be dimensioned and shaped to allow the legs 326 of the reusable module 250 to slide into the slots 328. The legs 326 can slide into the slots 328 to assist in maintaining connection between the reusable module 250 and the dock 222. Once the legs 326 are inserted into the slots 328, the legs 326 can prevent vertical displacement of the reusable module 250.

It can be advantageous to have the battery 224 in a disposable portion such as the dock 222 or the sensor 240. Establishing wireless communication 204 and performing wireless transmission requires a significant amount of power. If the reusable module 250 has an internal power source, its functionalities (for example, establishing wireless communication 204 and performing wireless transmission) can be limited by the capacity of the internal power source. In such configuration, the reusable module 250 needs to be replaced once its internal power source is depleted. In a wireless patient monitoring context, it is desirable to keep the same pairing device for each patient because having to use multiple pairing devices for the same patient often can lead to confusion and can create a need to reestablish connections between pairing devices and display devices. When the reusable module 250 has an external power source such as battery 224 of the dock 222, it does not need to be replaced when the battery 224 is depleted.

The batteries 224 can be zinc-air batteries powered by oxidizing zinc with oxygen in the air. It can be advantageous to use zinc-air batteries because they have higher energy density and thus have greater capacity than other types of batteries for a given weight or volume. In addition, zinc-air batteries have a long shelf life if properly sealed to keep the air out. The housing 300 can include one or more openings 332 that allow air to enter and react with the batteries 224. The one or more openings 332 can be sealed prior to use to prevent the air from entering and reacting with the batteries 224, thereby reducing capacity of the batteries 224. Once ready to use, the seal placed on the one or more openings 332 may be removed to allow the batteries 224 to provide power for the reusable module 250. The housing 300 may include a gasket 330 to seal the batteries 224 from the air. The gasket 330 can further increase the capacity of the batteries 224.

Having a disposable element (for example, the disposable module 220) as a power source for the reusable module 250 can address the above issues by eliminating the need to replace the reusable module 250. In this configuration, only the dock 222 or the sensor 240 needs to be replaced when the battery 224 is depleted. Since the cost of replacing the dock 222 or the sensor 240 can be much less than the cost of replacing the reusable module 250, this configuration can be advantageous in reducing operation costs. The sensor 240 may include the battery 224 that provides power to the reusable module 250. Both the sensor 240 and the dock 222 can include the battery 224. The reusable module 250 can include a battery consumption priority setting such that the reusable module 250 receives power first from the sensor 240 then from the dock 222.

The dock 222 can include a battery circuit 314 in contact with the batteries 224. The battery circuit 314 can be in contact with the flexible circuit 320. When the reusable module 250 is mated with the dock 222, the electronic contacts 258 can be in contact with the electronic contacts 228 of the flexible circuit 320 to allow the reusable module 250 to receive power from the batteries 224 via the flexible circuit 320.

The dock 222 can include an opening 362 and one or more supports 360. The one or more supports 360 can be formed on a side of the opening 362 and extend over a substantial portion of the opening 362. The supports 360 can be arcuate. The supports 360 can extend over the length of the opening 362. The cover 318 for the flexible circuit 320 can be placed over the opening 362 to hold the flexible circuit 320 over the opening 362.

The dock 222 can include a slot dimensioned to retain the reusable module 250 during the use of the sensor assembly 202. The reusable module 250 can be disposed between the housing 300 and the retainer 304. The slot of the dock 222 can include one or more arcuate surfaces or one or more angular corners. The slot of the dock 222 may be substantially rectangular or circular in shape. The slot can have substantially the same size, shape, and/or dimensions as that of the reusable module 250.

The reusable module 250 can include one or more electrical contacts 258. The electrical contacts 258 can be located on a bottom surface of the reusable module 250. The electrical contacts 258 can be substantially rectangular or circular in shape. The electrical contacts 258 can establish contact with electrical contacts 228 of the dock 222 when the reusable module 250 is mated with the dock 222. The contact between the electrical contacts 228 and electrical contacts 258 can allow information or data be transmitted between the reusable module 250 and the dock 222 of the disposable module 220.

As disclosed herein, the batteries 224 can be zinc-air batteries powered by oxidizing zinc with oxygen in the air. The openings 332 formed on the housing 300 can allow the air to enter through and react with the battery 224. The battery 224 then provides power for the disposable module 220 and the reusable module 250. However, the openings 332 may sometimes be covered by blankets, clothes, and the like, which can prevent the air from entering through the openings 332 and react with the battery 224. Consequently, power supply for the disposable module 220 and the reusable module 250 can be interrupted if the openings 332 are covered.

Figure 3D:
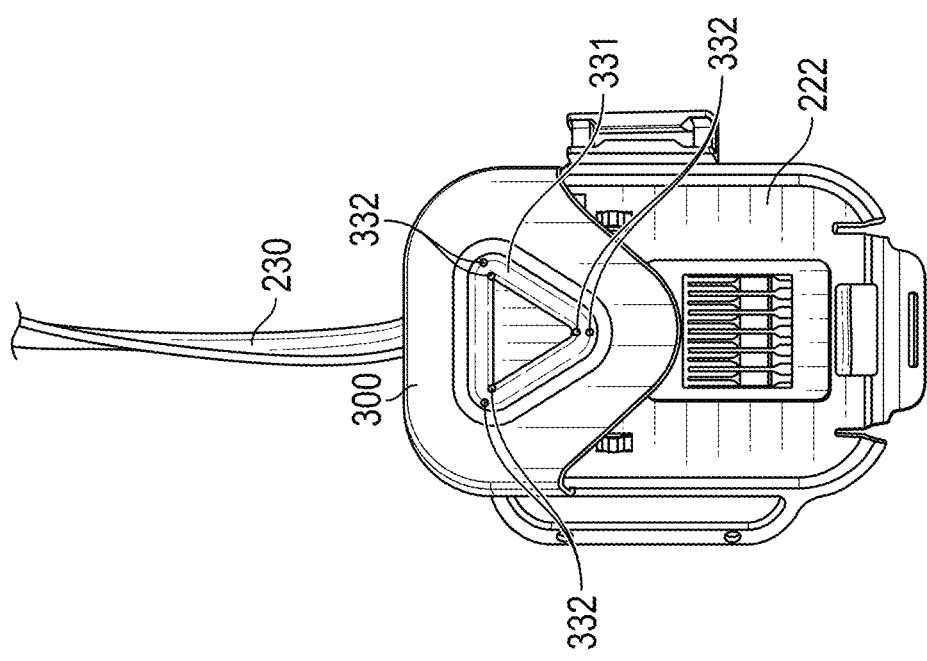
FIG. 3D illustrates a top view of an embodiment of a sensor assembly.

As shown in FIG. 3D, the housing 300 can include one or more recesses 331, such as, for example, channels, that can facilitate the air to enter through the openings 332. The recesses 331 can be formed on a top surface of the housing 300 such that the recesses 331 form openings that allow air flow. The openings 332 may be formed on an inner surface of the recesses 331. The inner surfaces of the recesses 331 are at least a predetermined distance away from the top surface of the housing 300 so that even when the housing 300 is covered, the openings 332 may remain uncovered and exposed to the air. The housing can have a single channel or multiple recesses, such as dimples or cutouts of any shape or size.

The number, dimensions, orientation, or positions of the channels 331 may be varied depending on the size of the housing 300 of the reusable module 250. The channels 331 can be oriented such that they together form a shape on the housing 300. The channels 331 may be oriented in a triangular shape (as shown in FIG. 3D), rectangular shape, pentagonal shape, hexagonal shape, and the like. The cross-sectional shape of the channels 331 can be circular, triangular, rectangular, or the like. In some examples, the channels 331 can extend to one or more edges of the housing 300 so that even when the top surface of the housing 300 is covered, the channels 331 extending to the edges of the housing 300 can ensure that the openings 332 remain exposed to the air.

Figure 4:
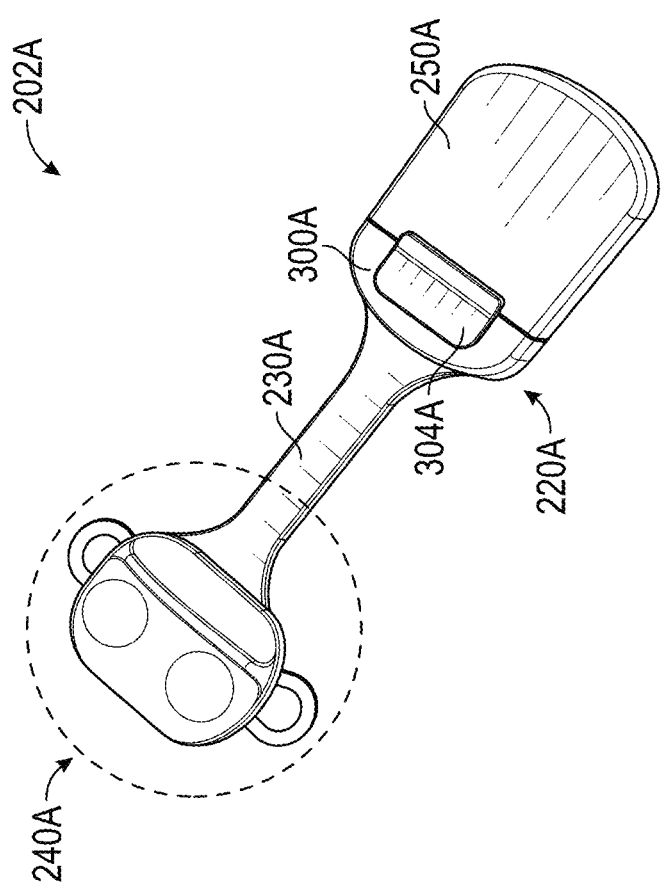
FIG. 4 illustrates a perspective view of another embodiment of a sensor assembly for collecting and wirelessly transmitting patient physiological data to a computing device.

FIG. 4 illustrates an example the sensor assembly 202, identified generally by the reference numeral 202A. Parts, components, and features of the sensor assembly 202A are identified using the same reference numerals as the corresponding parts, components, and features of the sensor assembly 202, except that a letter "A" has been added thereto. The illustrated example includes a disposable module 220A and a reusable module 250A coupled to each other.

The sensor assembly 202A can include a sensor 240A. The sensor 240A can be an O3 sensor that can be adhered to a forehead of a patient. The sensor assembly 202A can include a cable 230A that couples the sensor 240A and a dock 222A of the disposable module 220A. The cable 230A can be flat or round. As discussed above, the sensor 240A can include one or more batteries that can provide power for a reusable module 250A. The mating of the dock 222A and the reusable module 250A can facilitate electronic communication therebetween. The dock 222A can include a housing 300A that includes a retainer member 304A. Pressing down the retainer member 304A can allow the reusable module 250A to be coupled with or removed from the dock 222A.

Figure 5:
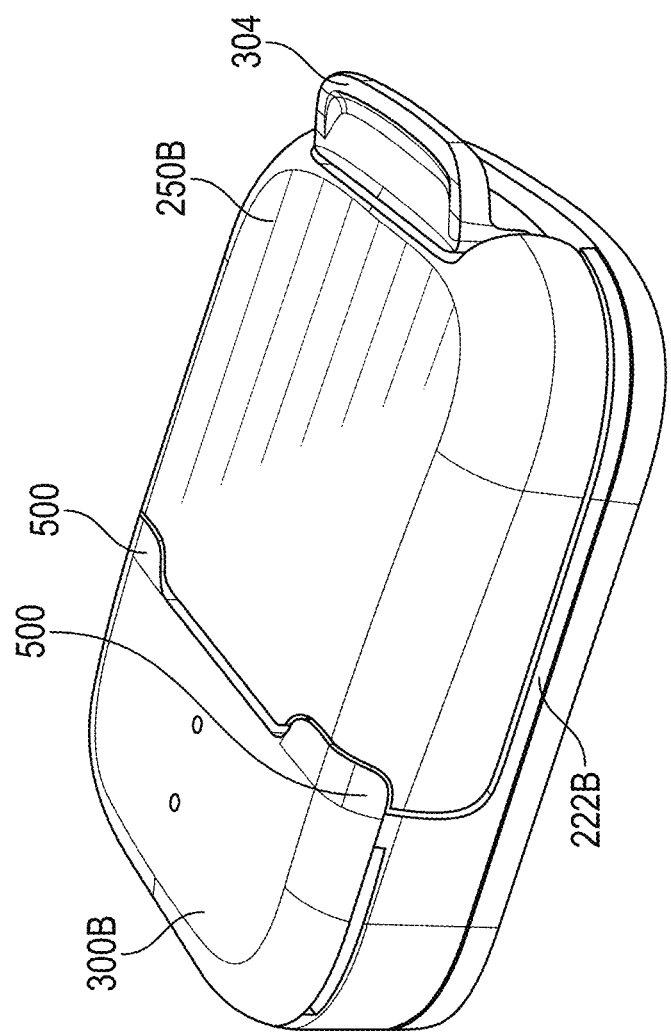
FIG. 5 illustrates a perspective view of another embodiment of a sensor assembly for collecting and wirelessly transmitting patient physiological data to a computing device.

FIG. 5 illustrates an example of the sensor assembly 202, identified generally by the reference numeral 202B. Parts, components, and features of the sensor assembly 202B are identified using the same reference numerals as the corresponding parts, components, and features of the sensor assembly 202, except that a letter "B" has been added thereto. The illustrated example includes a disposable module 220B and a reusable module 250B coupled to each other.

The sensor assembly 202B can include a sensor 240B. The sensor 240B can be a RAM sensor adhered to a neck of a patient. The sensor 240B can be an ECG sensor that can be adhered to a chest or abdominal area of a patient. The dock 222B can include a housing 300B and a retainer member 304B. The housing 300B can include one or more extensions 500 that can extend from the body of the housing 300B towards the retainer member 304B. The reusable module 250B can include cutouts that correspond to the one or more extensions 500. When the reusable module 250B is coupled with the dock 222B, the extensions 500 can extend over the cutouts of the reusable module 250B, preventing the reusable module 250B from being dislodged from the dock 222B.

Flexible Circuit

Figure 6A:
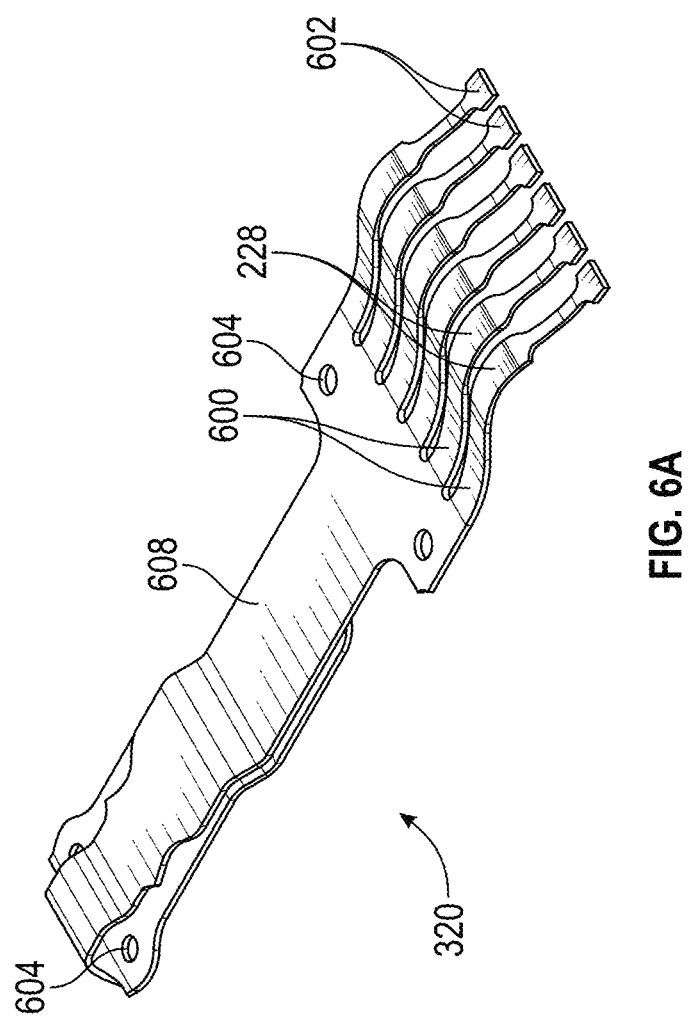
FIGS. 6A and 6B illustrate various views of a flex circuit of a disposable module of a sensor assembly.

FIG. 6A illustrates a perspective view of the flex circuit 320. The flex circuit 320 can include one or more elongate members 600 that can each include a tip 602, and a body 608. The electrical contracts 228 can be disposed on the one or more elongate members 600. The elongate members 600 can extend distally from the body 608. The tips 602 can be located at distal ends of the elongate members 600 of the flex circuit 320. The elongate members 600 can be flat or arcuate as shown in FIG. 6A. The elongate members 600 can become arcuate due to their interaction with the supports 360 and the cover 318. The elongate members 600 can include one or more substantially flat portions and/or one or more arcuate portions. Each of the one or more tips 602 can correspond to each of the one or more elongate members 600 of the flex circuit 320. Some of the elongate members 600 may not have electrical contacts 228. The flex circuit 320 can include the same or different number of the elongate members 600 and the tips 602. The flex circuit 320 can include one or more openings 604 that couple the flex circuit 320 to the dock 222.

As shown in FIGS. 6C and 6D, the tips 602 of the elongate members 600 can be positioned under the cover 318 while the elongate members 600 are supported by supports 360. Because the tips 602 can be wedged under the cover 318, the elongate members 600 can retain its arcuate shape over the supports 360.

Figure 6B:
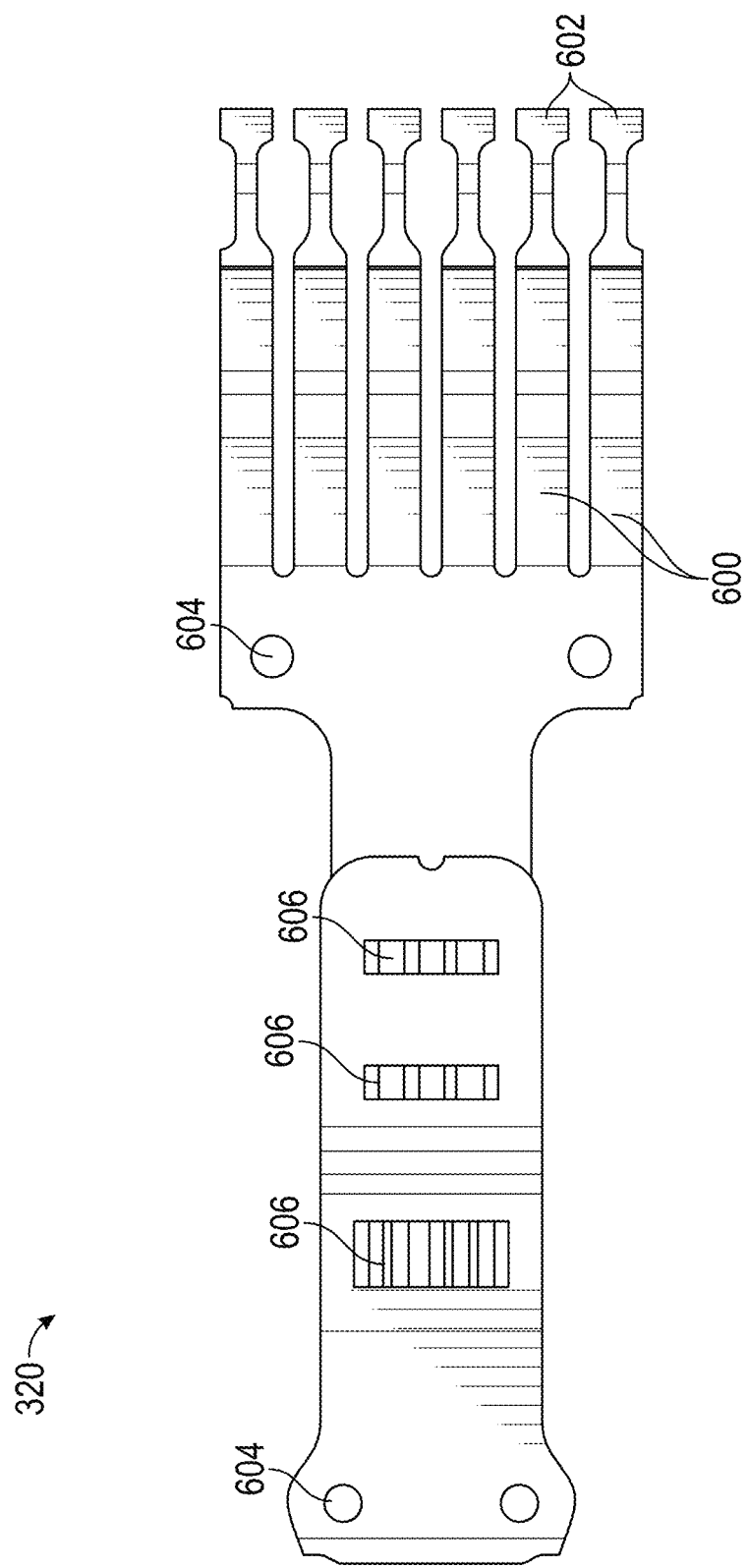

FIG. 6B illustrates a bottom view of the flex circuit 320. The flex circuit 320 can include one or more electrical contacts 606 that can be connected to the cable 230 and the battery circuit 314 (see FIGS. 3A and 3C). Therefore, power from the battery 224 can be transmitted to the electrical contacts 228 of the dock 222 via the electrical contacts 606 of the flex circuit 320. Moreover, the electrical contacts 606 can establish connection between the electrical contacts 228 and the sensor 240 via the cable 230.

The number of the elongate members 600 can correspond to the number of electrical contacts 258 of the reusable module 250 (see FIG. 3C). For example, the reusable module 250 has six electrical contacts 258 and the flex circuit 320 has six fingers, where each of the six fingers includes an electrical contact 228. The number of electrical contacts 258 of the reusable module 250 can be different from the number of elongate members 600 of the flex circuit 320. For example, the flex circuit 320 can include six elongate members 600 each having a corresponding electrical contact 310a, while the reusable module 250 has only four electrical contacts 258. The number of electrical contacts 258 of the reusable module 250 may be different from or the same with the number of electrical contacts 228 disposed on the elongate members 600 of the flex circuit 320.

Each the elongate members 600 of the flex circuit 320 can include an arcuate portion with a first curvature. The arcuate portions of the elongate members 600 can be laid over the opening 362 of the dock 222. The one or more electrical contacts 228 of the flex circuit 320 can be disposed over a portion of the elongate members 600 of the flex circuit 320. For example, the one or more electrical contacts 228 are located at an apex of each of the elongate members 600 of the flex circuit 320. In another example, the entire upper surface of each of the elongate members 600 defines the electrical contacts 228. The elongate members 600 of the flex circuit 320 can be configured such that the apex of the arcuate portions of the elongate members 600 of the flex circuit 320 are located at a predetermined distance away from the opening 362 of the dock 222. The apex of the elongate members 600 of the flex circuit 320 can point away from the opening 362 of the dock 222 such that the arcuate portions of the elongate members 600 define a concave surface facing the opening of the dock 222. The apex of the elongate members 600 can be arcuate in shape or substantially flat.

It can be advantageous to have the elongate members 600 of the flex circuit 320 include a curved portion upward and away (for example, concave downward) from the opening 362 of the dock 222. Such configuration can allow the elongate members 600 to act as springs providing reactive upward forces when pressed downward by the reusable module 250. Such upward forces provided by the elongate members 600 can allow the electrical contacts 228, 258 of the dock 222 and the reusable module 250, respectively, to maintain adequate contact between them.

The elongate members 600 of the flex circuit 320 can have different curvatures. For example, a first elongate member of the flex circuit 320 has a first curvature while a second elongate member of the flex circuit 320 has a second curvature. The first curvature of the first elongate member and the second curvature of the second elongate member can be the same or different. The first curvature of the first elongate member is greater than, less than, or equal to the second curvature of the second elongate member.

The elongate members 600 of the flex circuit 320, in their resting positions, may not have any arcuate portions. The elongate members 600 of the flex circuit 320 can be substantially linear prior to being installed on the dock 222. The elongate members 600, can be linear or curved. The elongate members 600 of the flex circuit 320 can include more than one linear portions.

The elongate members 600 of the flex circuit 320 can be flexible or not flexible. The flex circuit 320 can be laid on the dock 222 such that the elongate members 600 are laid over one or more supports 360 of the dock 222. The elongate members 600 can extend distally away from the body 608 of the flex circuit 320. The flex circuit 320 can include more than one elongate members 600. The flex circuit 320 can include one or more elongate members 600 that are flexible. Some the elongate members 600 may be flexible while other elongate members 600 are not.

As discussed above, the dock 222 can include the opening 362 over which the elongate members 600 of the flex circuit 320 can extend over. The dock 222 can include one or more supports 360 dimensioned and shaped to support the elongate members 600 of the flex circuit 320. When the flex circuit 320 is installed on the dock 222, the supports 360 can provide a surface on which the elongate members 600 of the flex circuit 320 can be placed on.

The supports 360 of the dock 222 can be curved and define the curvature of the arcuate portions of the elongate members 600. The supports 360 can be arcuate. It can be advantageous to have the supports that correspond to each of the elongate members 600 of the flex circuit 320. For example, the dock 222 has six independent supports 360 associated with each of the six elongate members 600 of the flex circuit 320. Such configuration allows each of the corresponding elongate members 600 and the supports 360 of the dock 222 to move independently from other elongate members 600 and supports 360 as opposed to all of the elongate members 600 and the supports 360 moving that the same time. Such configuration can make inserting the reusable module 250 into the slot 940 of the dock 222 easier.

Moreover, this can allow interoperability between the dock 222 and the reusable module 250 that have different height configurations for the electrical contacts 258.

It can be advantageous to have the supports 360 for the flex circuit 320 include a curved portion upward and away (e.g., concave downward) from a bottom portion of the dock 222. Such configuration can allow the supports to act as springs providing reactive upward force when pressed downward by the reusable module 250. Such upward forces can allow the electrical contacts 228, 258 of the dock 222 and the reusable module 250, respectively, to maintain adequate contact between them. The supports 360 can include a first upward portion that is concave upward, a second upward portion that is concave downward, and a third downward portion that is concave downward. The supports 360 may include a first upward portion that is concave upward and a second upward portion that is concave downward. The supports 360 can include one or more inflection point, defined as a point where the supports 360 changes from being concave to convex, or vice versa. The supports 360 can also include one or more linear portions.

The supports 360 may also provide sufficient force to push the reusable module 250 away the dock 222 when the retainer member 304 is pulled away from the reusable module 250. The support 360 may push the reusable module 250 away from the dock 222 when the retainer member 304 is in its second position, as discussed above. When the retainer 304 no longer engages the groove 322 of the reusable module 250, it may no longer provide force to counteract the force generated by the supports 360, allowing the supports 360 to push the reusable module 250 away from the dock 222.

The supports 360 can have a length that is greater than, less than, or equal to the length of the elongate members 600 of the flex circuit 320. The supports 360 have a width that is greater than, less than, or equal to the width of the elongate members 600. The supports 360 can have a thickness that is greater than, less than, or equal to the thickness of the elongate members 600 to allow the supports 360 to provide sufficient mechanical support and to withstand the downward force exerted on the elongate members 600 and the supports 360 by the reusable module 250. The interaction between the elongate members 600, supports 360, and the reusable module 250 will be further described below.

The supports 360 can be made out of the same or different material as the dock 222.

The body 608 of the flex circuit 320 can be laid under the housing 300 of the dock 222. The body 608 can be connected to the cable 230 connected to the dock 222 such that the flex circuit 320 allows the health monitoring data from sensor 240 to be transmitted to the electrical contacts 606 of the flex circuit 320.

FIGS. 6C and 6D illustrate a change in a configuration of the flex circuit 320. When the reusable module 250 is inserted into the slot 940 of the dock 222, the engagement between the reusable module 250 and the dock 222 can change the position of the tips 602 of the flex circuit 320. FIGS. 6C and 6D show relative positions of the tips 602 before and after the reusable module 250 is mated with the dock 222. The relative positions of the tips 602 before the reusable module 250 is inserted into the dock 222 are denoted by L1. When the reusable module 250 is inserted into the slot 940 of the dock 222, the reusable module 250 can apply a downward force (denoted as F) to the arcuate portions of the elongate members 600 and the supports 360. This downward force F can cause the arcuate portions and the supports 360 to move downward. This downward movement of the elongate members 600 and the supports 360 can cause the tips 602 to move distally along an axis defined by the elongate members 600 of the flex circuit 320. Specifically, such downward motion can cause the relative positions of the tips 602 to change from L1 to L2, where L2 is greater than L1.

FIGS. 6C and 6D illustrate another change in configuration of the flex circuit 320. When the reusable module 250 is inserted into the dock 222, the engagement between the reusable module 250 and the dock 222 can change the position of the tips 602 of the flex circuit 320. The relative difference between the heights of the apex of the arcuate portions of the elongate members 600 and the body 608 before for reusable module 250 is inserted is denoted by H1. When the reusable module 250 is inserted into the dock 222, the reusable module 250 can apply a downward force (denoted as F) to the arcuate portions of the elongate members 600 and the supports 360. This downward force F can cause the arcuate portions and the supports 360 to move downward. Such downward motion can cause the relative difference between the heights of the apex of the arcuate portions of the elongate members 600 and the body 608 to change from H1 to H2, where H2 is less than H1. It is possible that the relative different between the heights of the apex of the arcuate portions of the elongate members 600 and the body 608 can change while the relative positions of the tips 602 do not change from L1 to L2, or vice versa.

The downward force F in a first direction can cause the supports 360 of the dock 222 to provide a reactive force in a second direction. The second direction of the reactive force can be an opposite direction then the first direction of the downward force F. Specifically, the reactive force by the supports 360 can be upward away from the dock 222. The supports 360 can act as a spring such that as the supports 360 moves further downward from its natural position (for example, as H1 changes to H2), the magnitude of the reactive force increases. The directions of F and the reactive force may be opposite from each other. The magnitude of the reactive force is less than the downward force F in order to allow the supports 360 to move downward and allow the reusable module 250 to be inserted into the slot 940 of the dock 222. The magnitude of the downward force F caused by the reusable module 250 may correlate to the following: the change in the relative height difference between the apex of the elongate members 600 and the body 608 (for example, from H1 to H2) and the change in the positions of the tips 602 (for example, from L1 to L2).

The elongate members 600 of the flex circuit 320 can have a first degree of curvature before the reusable module 250 is inserted into the dock 222. The elongate members 600 can have a second degree of curvature after the reusable module is inserted into the dock 222. The first degree of curvature of the elongate members 600 can be greater than, less than, or equal to the second degree of curvature. The first degree of curvature can correspond to a first position of the tips 602 (for example, L1). The second degree of curvature can correspond to a second position of the tips 602 (for example, L2). Moreover, the first degree of curvature can correspond to a first position of the apex (for example, H1) of the elongate members 600. The second degree of curvature can correspond to a second position of the apex (for example, H2) of the elongate members 600.

The reactive force provided by the supports 360 can maintain sufficient contact between the electrical contacts 310a of the dock 222 and the electrical contacts 310b of the reusable module 250 to allow electrical signals be transmitted between the contacts.

Attachment Mechanisms

FIGS. 7A-7I illustrate various examples of an attachment mechanism for the disposable module 220 of the sensor assembly 202.

Figure 7A:
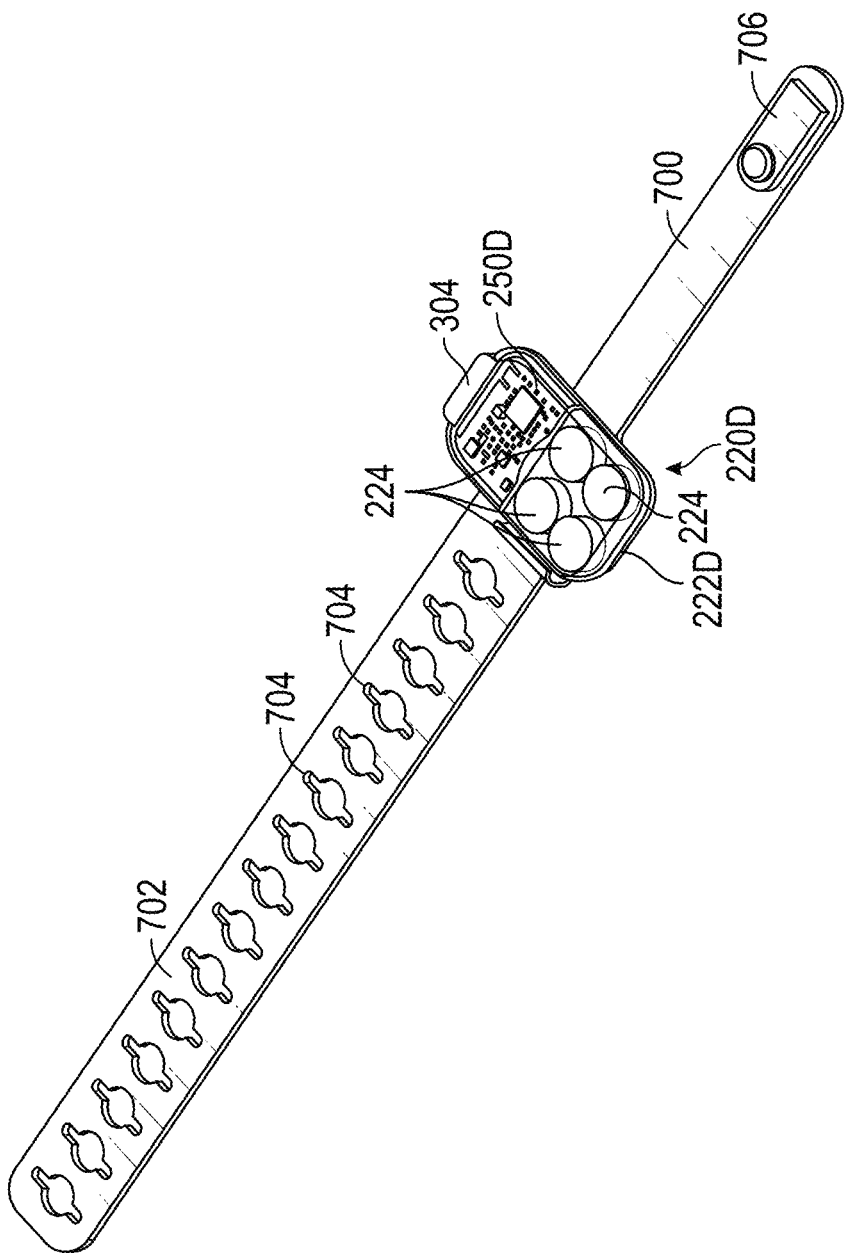
FIGS. 7A-7I illustrate various perspective view of different embodiments of sensor assembly coupled with various embodiments of attachment mechanisms.
Figure 7C:
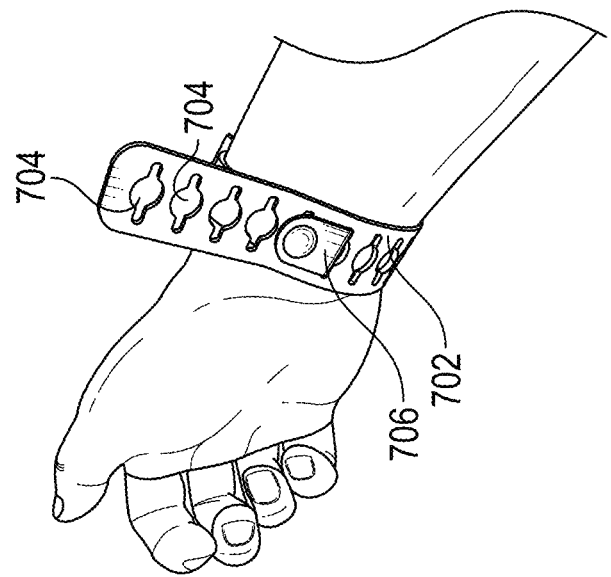
Figure 7B:
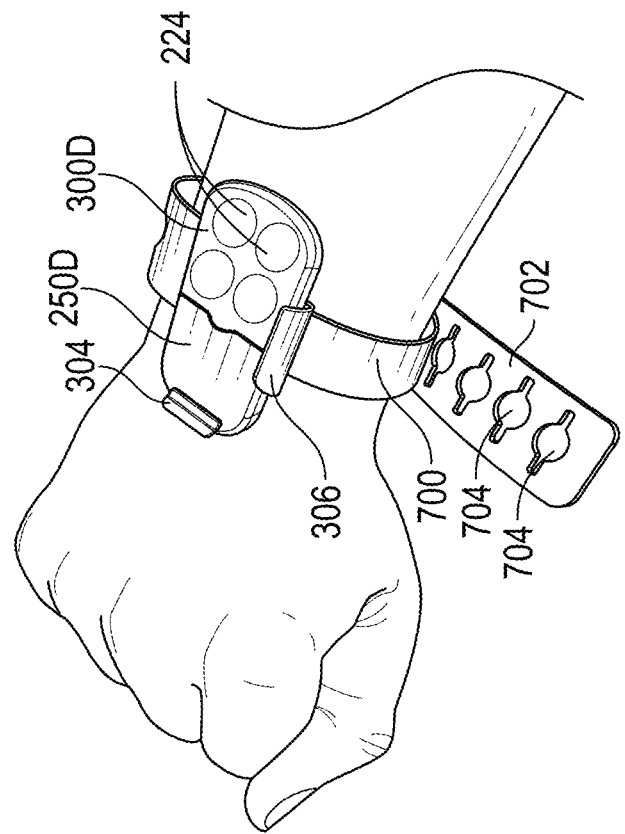

With reference to FIGS. 7A-7C, the dock 222 can be coupled to a first strap 700 and a second strap 702. The first strap 700 and the second strap 702 can be mechanically coupled to the dock 222. The straps 700, 702 may be removably coupled to the dock 222. Alternatively, the straps 700, 702 can be integrated to the dock 222. The second strap 702 can include one or more openings 704. The first strap 700 can include a fastener 706 configured to affix the second strap 702 to the first strap 700. The openings 704 can be dimensioned receive the fastener 706. The first strap 700 can be inserted through one of the openings 704 to removably attach the dock 222 to a patient. The straps 700, 702 can have varying thicknesses, lengths, and flexibility. The straps 700, 702 may be stretchable. The first strap 700 can include one or more openings 704 while the second strap 702 includes the fastener 706.

A distal end of the first strap 700 can be inserted into one of the openings 704 of the second strap 702. The fastener 706 of the first strap 700 may be inserted into one of the openings 704 of the second strap 702. The interaction between the fastener 706 and openings 704 can removably affix the dock 222 as shown in FIGS. 7B and 7C.

Figure 7E:
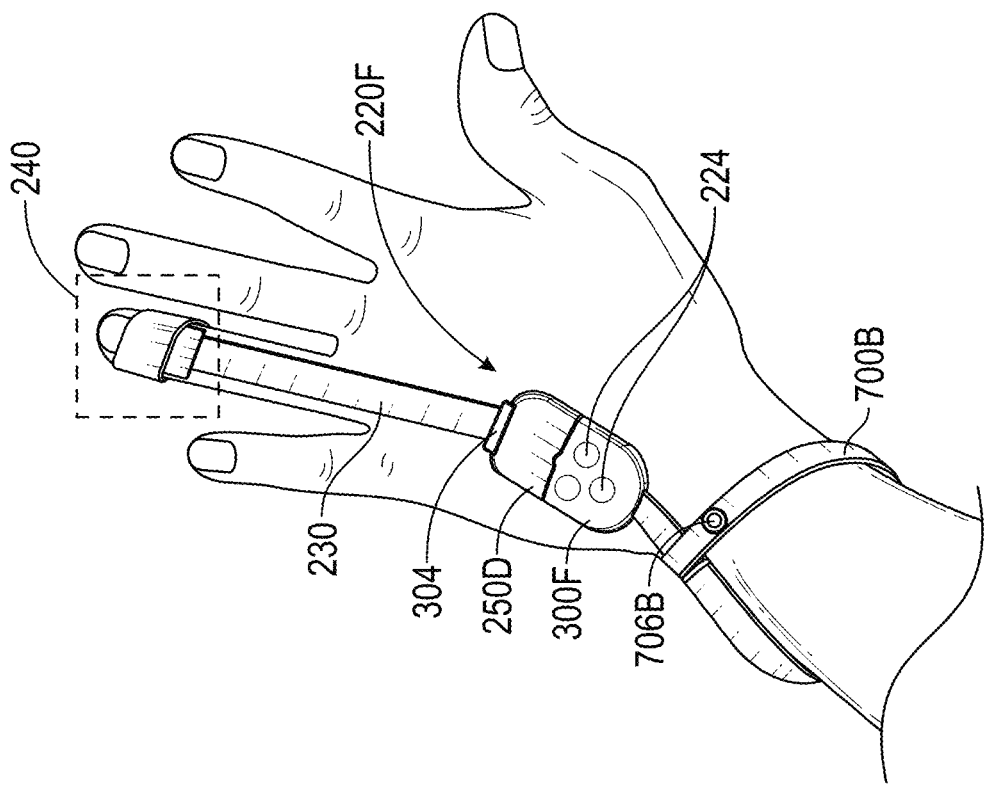
Figure 7D:
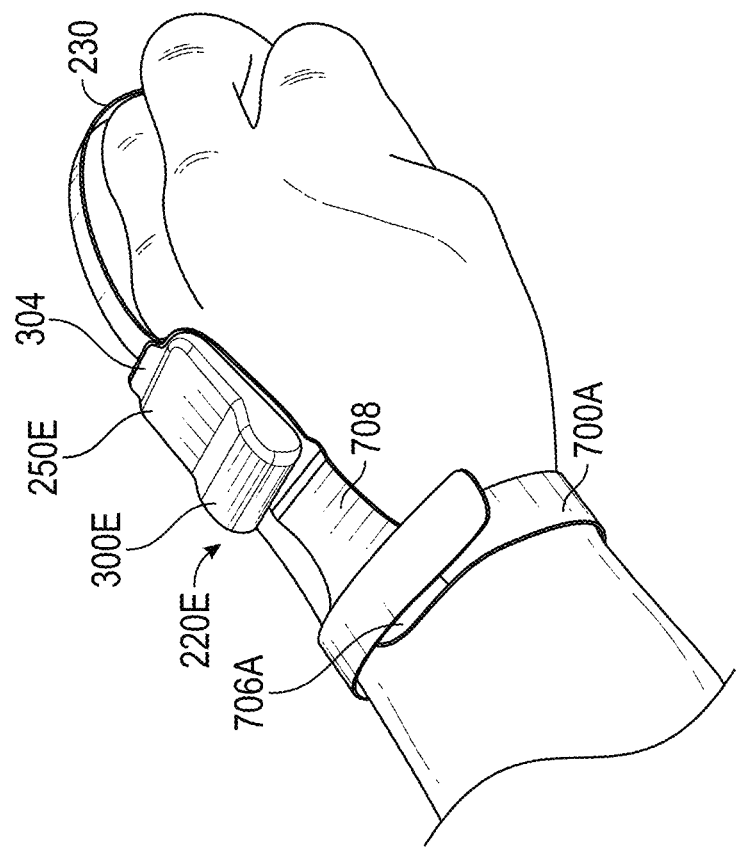

FIG. 7D shows the dock 222 of the disposable module 220 coupled to yet another example of an attachment mechanism. The dock 222 can be coupled to an extension 708 extending away from the disposable module 220. For example, as shown in FIG. 7D, the disposable module 220 can be placed on top of a hand and the extension 708 can extend towards a wrist of a patient. The extender 708 can include a strap 700A that can loop around the wrist to secure the disposable module 220 and the extension 708 to the wrist. The strap 700A can include a fastener 706A that can adhere the strap 700A to a top surface of the extension 708. The fastener 706A can be disposed at a distal end or a proximal end of the strap 700A. The fastener 706A may adhere to a top surface or a bottom surface of the 700A. The fastener 706A can incorporate one of the following mechanisms including a hook and loop system, Velcro, buttons, snaps, magnets, and the like.

FIG. 7E illustrates another example of an attachment mechanism for the disposable module 220. As shown here, the dock 222 can be coupled to a strap 700B. A first, proximal end of the strap 700B can be attached to the dock 222, while a second, distal end of the strap 700B can extend away from the dock 222. The distal end of the strap 700B can include a fastener 706B. The strap 700B can affix the dock 222 to a wrist of a patient by having the second, distal end looped around the wrist. The distal end of the strap 700B can be affixed by looping over or under the proximal end of the strap 700B. Once the distal end of the strap 700B looped around the first, proximal end of the strap 2310, the fastener 706B can be used to secure the distal end of the strap 700B. The fastener 706B can incorporate one of the following mechanisms including, but not limited to, a hook and loop system, Velcro, buttons, snaps, and/or magnets.

Figure 7F:
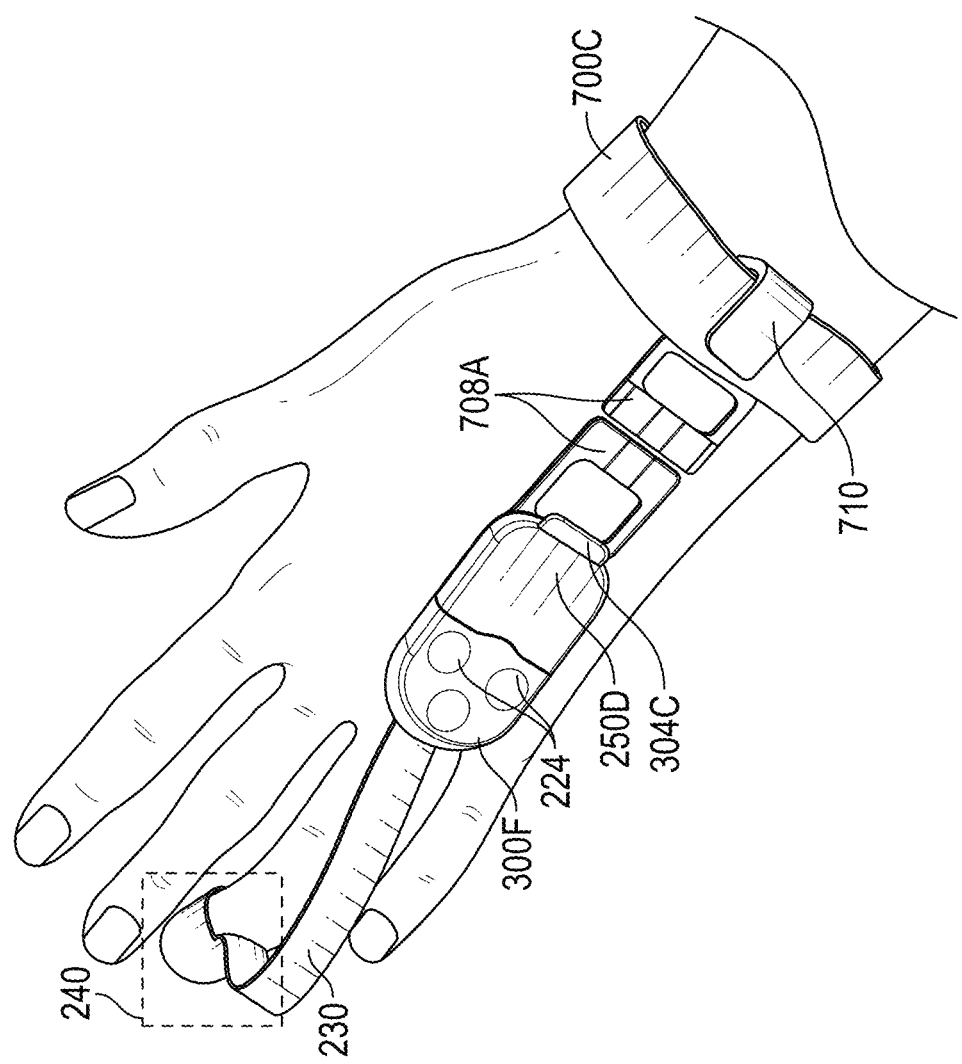

FIG. 7F shows yet another example of an attachment mechanism for the sensor assembly 202. The sensor assembly 202 can be coupled to an extender 708A which includes a hook 710. The extender 708A can extend away from the dock 222 of the sensor assembly 202, where the hook 710 is coupled to a distal end of the extender 708A. The hook 710 can wrap around the strap 700C such that the extender 708A and the dock 222 are substantially held in place with respect to a wrist of a patient. The strap 700C can be modular. The strap 700C may be removably connected or affixed to the hook 710 of the extender 708A. The strap 700C can be a flexible band that can tightly wrap around a patient's wrist, as shown in FIG. 7F.

Figure 7G:
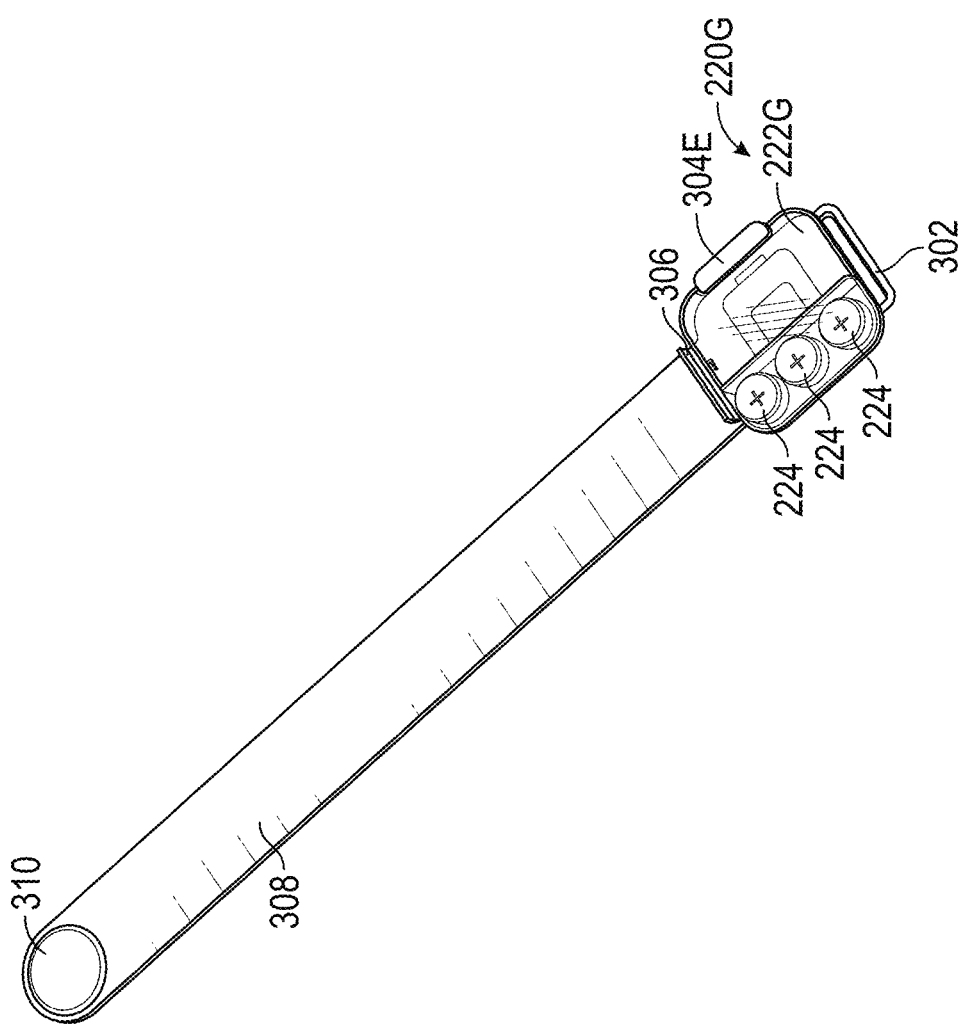

FIG. 7G shows yet another example of an attachment mechanism for the sensor assembly 202. The dock 222 can include the strap 308 extending from a first side of the dock 222, the strap 308 dimensioned to wrap around a patient's wrist in a first direction, and the strap loop 302 extending from a second side of the dock 222. The strap 308 can include the fastener 310 disposed near its distal end. The strap 3810 can be routed around the patient's wrist and through the strap loop 302 of the dock 222. Once routed through the strap loop 302 of the dock 222, the strap 308 can be routed around the strap loop 302 and wrap the wrist in a second direction. The first direction of wrapping the strap 308 around the wrist can be clockwise or counterclockwise. The second direction of wrapping the strap 308 around the wrist can be clockwise or counterclockwise. FIG. 7H shows the sensor assembly 202 of FIG. 3A affixed to a patient's wrist.

Figure 7I:
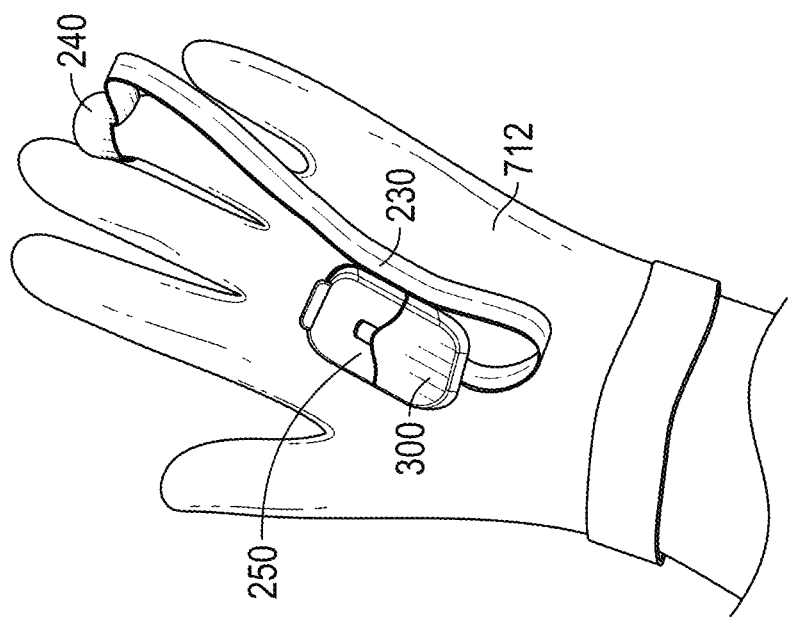
Figure 7H:
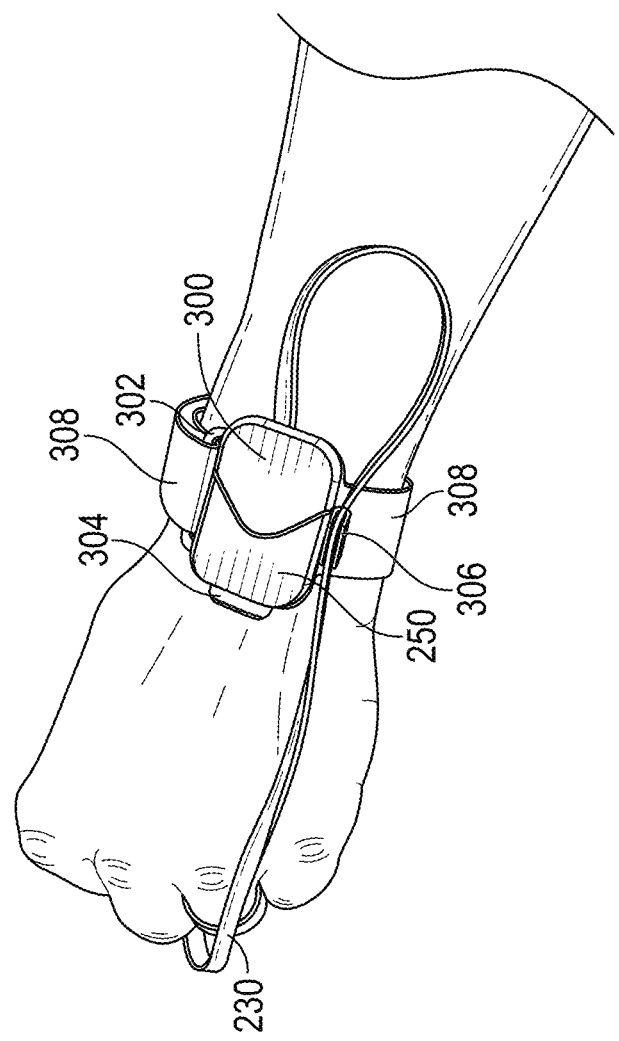

FIG. 7I illustrates yet another example of an attachment mechanism for the sensor assembly 202. The dock 222 and the sensor 240 can be coupled to a glove 712. When the glove 712 is placed on a patient's hand, the sensor 240 of the sensor assembly 202 can be placed one of the fingertips. The dock 222 can be attached to a top portion of the glove 712 as shown in FIG. 7I. The sensor 240 of the sensor assembly 202 can be built inside or outside the fingers of the glove 712. The sensor 240 can be integrated to the fingers of the glove 712. The cable 230 of the sensor assembly 202 can be integrated to the glove 712.

Dongle and Pairing

Given the time demands placed on clinicians in busy hospitals and the number of patients and patient monitoring devices, manual interaction to establish connection between the computing device 206 (for example, a mobile patient monitoring display device) and the reusable module 250 can be burdensome. In some cases, the time required to manually interact with a patient monitor device in order to establish connection with a pairing device can even jeopardize a patient's well-being in particularly urgent circumstances. For at least the foregoing reasons, it would be advantageous for the computing device 206, such as bedside patient monitors, central monitoring stations, and other devices, to have the capability to detect the presence of the reusable module 250 nearby and establish a wireless communication 204 with the reusable module 250.

Figure 8B:
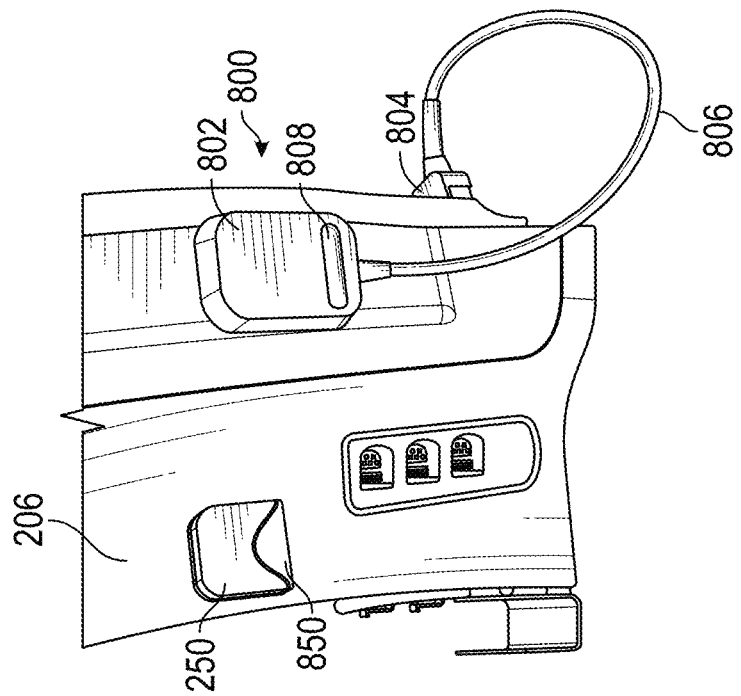
FIGS. 8A-8C illustrate various views of a dongle operatively connected to the computing device.
Figure 8A:
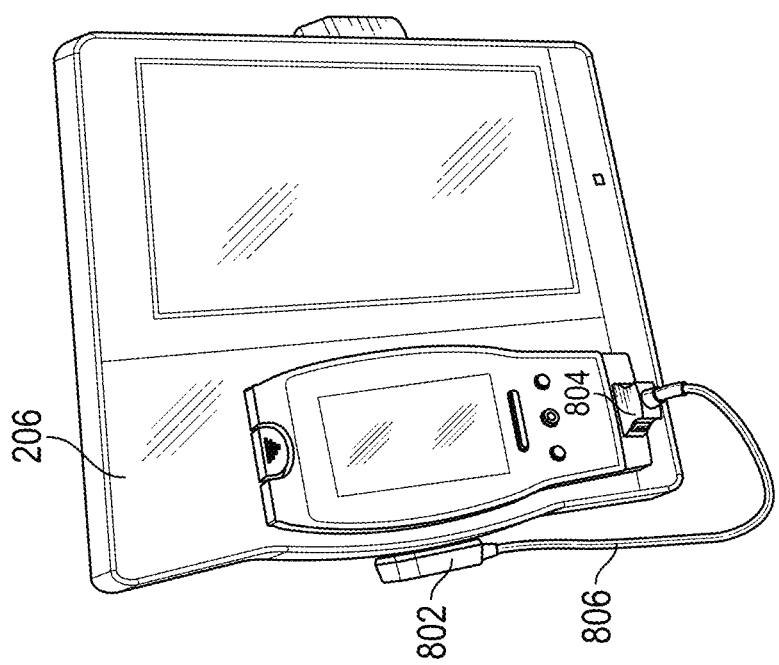
Figure 8C:
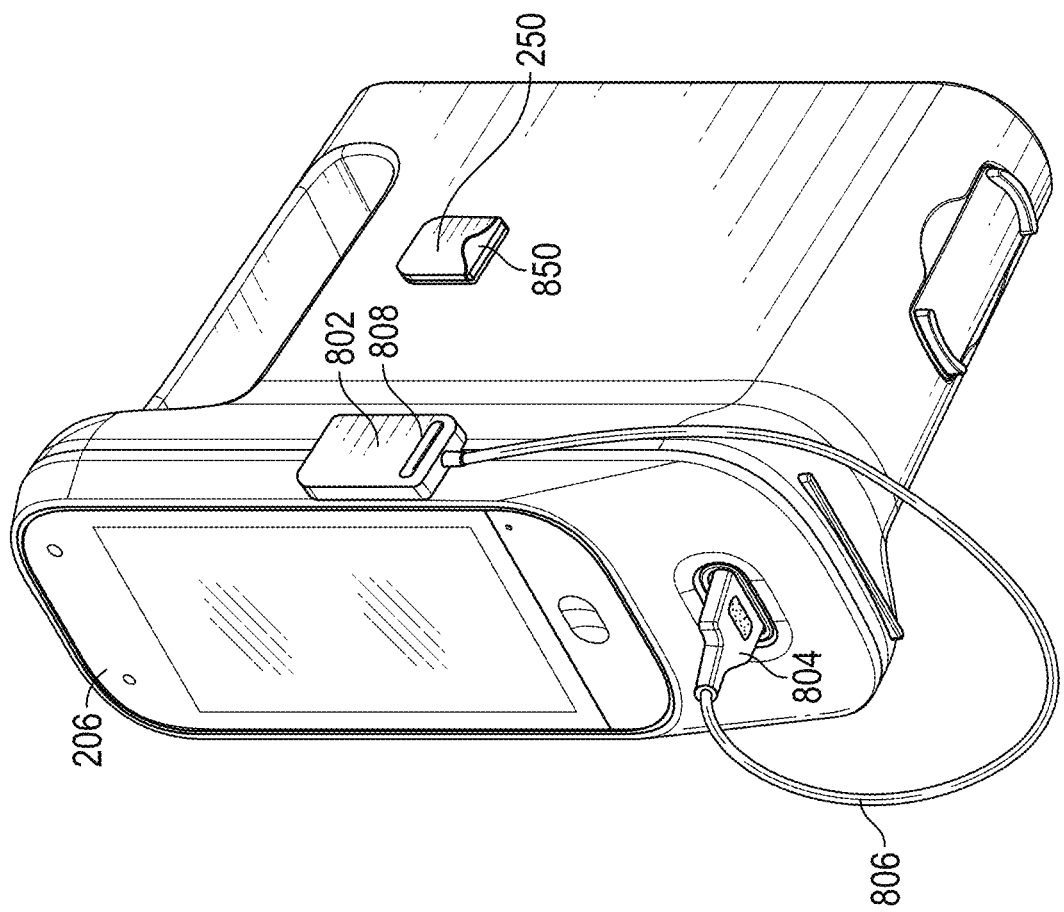

FIGS. 8A-8C illustrate various view of a dongle 800 connected to the computing device 206. The dongle 800 can include a body 802 and a connector 804 coupled to the body 802 via a cable 806. The connector 804 can connect to the computing device 206 to allow transmissions between the dongle 800 and the computing device 206. The cable 806 can include one or more conductive wires that can transmit data and/or power between the body 802 and the connector 804. The body 802 of the dongle 800 can be removably attached to the computing device 206. The body 802 can receive power from the computing device 206 via the connector 804 and the cable 806.

When the dongle 800 is connected to the computing device 206 via the connector 804, the computing device 206 can automatically detect the connector 804. The computing device 206 can determine a type of connector 804 and automatically change its settings. The settings may include, but not limited to, display settings for the display 208, display setting for the computing device 206 (for example, color of lights used to denote pair or communication status), communication protocol settings (for example, type of wireless communication utilized), communication signal settings (for example, varying communication signal type or strength based on different types of communications), and the like. Additionally, the settings for the dongle 800 can change to accommodate different types of computing devices 206 and their displays 208. Such setting can include display settings (for example, colors or messages denoting communication/pairing status), communication signal settings (for example, frequency of wireless signal used), communication protocol settings (for example, types of wireless communication used), and the like.

The computing device 206 can receive processed physiological parameter data and display on a display screen. This feature can be advantageous because it can reduce the amount of processing power required by the computing device 206. As discussed above, the reusable module 250 can perform signal processing on raw patient physiological data collected by the sensor 240 and calculate patient physiological parameters. Therefore, the data transmitted from the reusable module 250 to the computing device 206 via the body 802 includes patient physiological parameters that do not require further signal processing.

The reusable module 250 can transmit patient physiological parameters with low resolution and the dongle 800 can fill in the data using various methods. For example, the dongle 800 may use different types of averages to fill in the data transmitted from the reusable module 250. The reusable module 250 can send waveform data, for example, at a low resolution and the dongle 800 can increase the resolution of the waveform. This feature can further increase the life of the battery 224 of the disposable module 220.

The body 802 of the dongle 800 can include a transceiver or receiver, and a communication module for communicatively coupling the computing device 206 to other patient monitoring devices such as the reusable module 250. When the reusable module 250 is sufficiently proximate, the body 802 can communicate with the reusable module 250 so as to identify the reusable module 250. The body 802 can include a radio-frequency identification (RFID) reader and while the reusable module 250 can include an embedded RFID chip containing an identifying information unique to the reusable module 250. The RFID reader of the body 802 can identify the embedded RFID chip inside the reusable module 250 and establish a wireless communication 204 between the reusable module 250 and the body 802. The body 802 can include a transceiver that complies with one or more short-range wireless communications standards, such as Bluetooth®. Other types of wireless communication protocols may be utilized to establish communication and transfer data between the dongle 800 and the reusable module 250.

The body 802 can include a groove 808 dimensioned to receive a portion of the reusable module 250. The groove 808 can indicate a medical personnel where to place the reusable module 250 in order to associate (for example, pair) the reusable module 250 with the computing device 206.

The dongle 800 can include a holder 850 that can retain the reusable module 250 when not in use. The holder 850 can be separate from the dongle 800 as shown in FIG. 8B. The holder 850 can include a surface dimensioned and shaped to engage with a surface of the reusable module 250 to assist in retaining the reusable module 250. The holder 850 can use a magnet to retain the reusable module 250. The holder 850 can be attached on the computing device 206 via various mechanisms including, but not limited to, adhesives, Velcro, magnet, and the like.

Figure 9C:
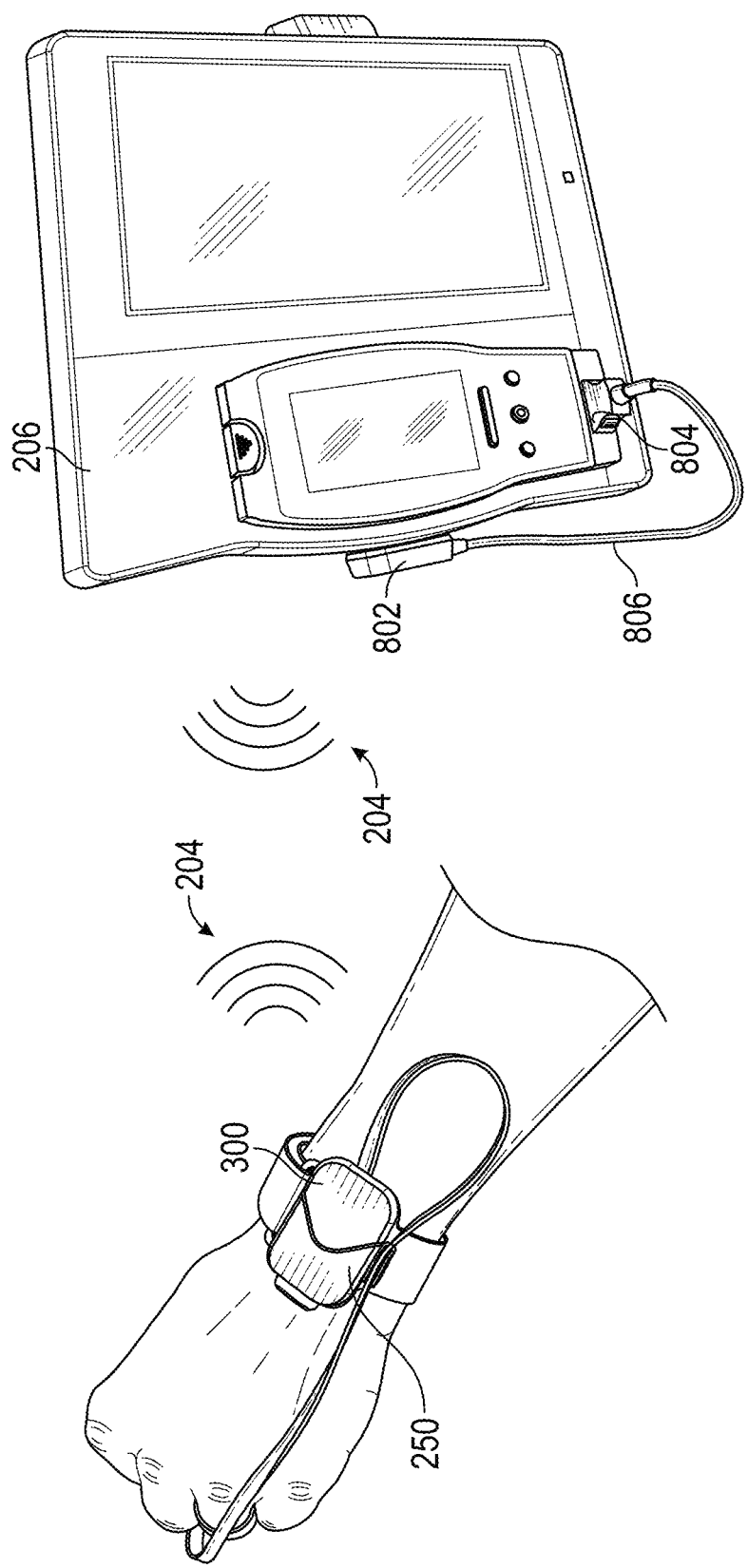

FIGS. 9A-9C illustrate a process of pairing the reusable module 250 with the computing device 206 using the dongle 800. Wireless communication 204 between the reusable module 250 and the computing device 206 can be initiated by coupling the connector 804 of the dongle 800 with the computing device 206 and placing the reusable module 250 within a certain distance away from the body 802 of the dongle 800. The reusable module 250 may or may not require a physical contact with the body 802 to transfer its identifying information to the dongle 800.

When the reusable module 250 is brought sufficiently close to the body 802 of the dongle 800, the body 802 can, for example, use RFID technology to receive from the reusable module 250 information that can identify the reusable module 250 to the computing device 206. The identifying information can be an ID tag of a token specific or unique to the reusable module 250. The identifying information can include Bluetooth® parameters of the reusable module 250. Other types of identification mechanisms can be used to allow the computing device 206 to identify and associate with the reusable module 250.

The identifying information of the reusable module 250 can be stored in the memory 256. The identifying information may be hardwired into the memory 256 or programmable. The identifying information can include pairing parameters (for example, a pairing device ID) that is unique to the reusable module 250. The identifying information may be unique to the patient to whom the reusable module is assigned. The identifying information of the reusable module 250 may also include other information such as, for example, the pairing device's information, information regarding the sensor 240 the reusable module 250 is operatively connected to, or a code or other indicator for initiating a predetermined action to be performed by the computing device 206. Additionally and/or alternatively, the identifying information of the reusable module 250 can be generated using physiological data collected by the sensors 240 of the sensor assembly 202.

The body 802 of the dongle 800 can include a RFID reader. The RFID reader can communicatively couple the computing device 206 to other patient monitoring devices such as the reusable module 250. When the reusable module 250 is proximate to the body 802, as shown in FIG. 9B, the RFID reader of the body 802 can receive the identifying information from the reusable module 250. Once the body 802 receives the identifying information, the identifying information can be transmitted to the computing device 206 via the cable 806 and the connector 804.

The computing device 206 can use the identifying information to associate the reusable module 250 with the computing device 206. For example, the Bluetooth® parameters of the reusable module 250 can be used to associate the reusable module with the computing device 206. Once associated, the reusable module 250 can connect with the computing device 206 using the pairing parameters (for example, Bluetooth® parameters) included in the identifying information. The computing device 206 can identify the reusable module 250 and allow wireless communication 204 with the reusable module 250 using the Bluetooth® parameters it received from the reusable module 250. After establishing connection with the computing device 206, the reusable module 250 can communicate with the dongle 800 and the computing device 206 via Bluetooth® transmission. Other types or standards of wireless communication can be used, including, for example, ultrasound, Near Field Communication (NFC), and the like. If multiple reusable modules 250 are proximate to the computing device 206, a priority scheme or a user acknowledgment may be used to determine which reusable modules 250 are accommodated.

The reusable module 250 can use the NFC to provide instructions to program the dongle 800 to take certain actions in certain situations. The NFC communication circuitry of the reusable module 250 can have an associated memory that can have read/write capabilities. For example, the reusable module 250 can use NFC to indicate how long the dongle 206 must wait before deleting the pairing parameters ("giving up"). In another example, the reusable module 250 can use the NFC to indicate when the dongle 800 is disallowed from deleting the pairing parameters ("not giving up"). The NFC can be used to allow the dongle 800 to associate with one or more reusable modules 250 at the same time.

The dongle 800 can use the NFC to receive various types of information from the reusable module 250. The dongle 800 can receive information associated with NFC components of the reusable module 250 and determine sensor types, patient types, patient information, physician information, hospital information, authorized uses, authorized supplies, authorized manufacturers, emitter wavelengths, or indications of the usage or life of the reusable module 250, parameters the reusable module 250 is capable of measuring, and the like. For example, the dongle 800 can receive information via the NFC to determine that a particular reusable module 250 is designed to work with sensor assembly 202. The dongle 800 can also write back using NFC. For example, the dongle 800 can provide programming information through NFC to the reusable module 250. The dongle 800 can also write sensor usage information to the reusable module 250. For example, the reusable module 250 may only be allowed to be used a certain number of times before it must be discarded in order to maintain quality. This information can be written to the reusable module 250 through NFC communication.

Throughout the present disclosure, it is to be understood that the dongle 800 may be incorporated directly into the computing device 206. For example, the dongle 800 can be built into the circuitry of the computing device 206 such that the dongle 800 and the computing device 206 are in the same housing. In another example, the dongle 800 and the computing device 206 are in the same housing but the dongle 800 is not built into the circuitry of the computing device 206. The dongle 800 can be incorporated into the computing device 206 such that the dongle 800 is located near an outer housing or body of the computing device 206. Such a configuration can allow the reusable module 250 to readily establish wireless communication 204 with the dongle 800. The dongle 800 incorporated directly into the computing device 206 can prevent possible connection issues between the dongle 800 and the computing device 206.

Once the computing device 206 is associated with the reusable module 250, it can transmit a signal to the reusable module 250 indicating that the reusable module 250 is associated with the computing device 206. Different types of notifications can be generated when the reusable module 250 has successfully established wireless communication 204 with the computing device 206. The notifications can be generated by the computing device 206, the reusable module 250, or both.

The computing device 206 can provide an auditory notification or a visual notification on the display 208. For example, the computing device 206 can play a pattern of beeps or a predetermined melody for successful pairing. In another example, the computing device can play an auditory message such as "SpO$_2$ sensor number 1234 has been successfully paired with patient monitoring device A123." Visual notifications can include a blinking LED on the display 208. Another example of a visual notification can be in a form of text such as "Pairing successful" displayed on the display 208. The reusable module 250 has one or more LEDs to indicate status of wireless communication 204 with the computing device 206. For example, the reusable module 250 can include a red LED to indicate that no wireless communication 204 has been established between the reusable module 250 and the computing device 206. In another example, the reusable module 250 can include a blue LED to indicate that the reusable module 250 has established the wireless communication 204 with the computing device 206. A blinking green LED may be used to indicate that the computing device 206 is waiting for the reusable module 250 to establish the wireless communication 204 with the computing device 206. Different color LEDs and different schemes can be used to indicate different status of wireless communication 204 between the reusable module 250 and the computing device 206.

After receiving the pairing parameters from the reusable module 250, the computing device 206 can wait for a predetermined time period for the reusable module 250 to establish the wireless communication 204 (for example, Bluetooth® connection). If the wireless communication 204 is not established within the predetermined time period, the pairing parameters can expire, requiring the reusable module 250 to retransmit the pairing parameters to the computing device 206 again. The predetermined time period can be modified.

Once the computing device 206 receives the pairing parameters from the reusable module 250, the reusable module 250 can be mated with the dock 222, as shown in FIG. 9C. Once the reusable module 250 is mated with the dock 222, it can draw power from the battery 224 to establish wireless communication 204 with the computing device 206. The reusable module 250 can use the power drawn from the battery 224 to perform signal processing on the raw data to calculate physiological parameters. Once the physiological parameters are determined, the reusable module 250 can use the power from the battery to transmit the physiological parameters to the computing device 206 via the wireless communication 204.

The computing device 206 can receive the patient data including patient physiological parameters from the reusable module 250 and display the parameters on the display 208. The computing device 206 can receive the patient data via the body 802 of the dongle 800. In other words, the body 802 of the dongle 800 can receive patient physiological parameters from the reusable module 250 and in turn transmit the parameters to the computing device 206. As discussed above, Bluetooth® can be used to transmit the patient data between the reusable module 250 and the computing device 206 (or the body 802). For example, the reusable module 250 operatively connected to a SpO$_2$ sensor can establish Bluetooth® communication with the computing device 206. The computing device 206 can receive the patient data including SpO2 parameters from the reusable module 250 and display the parameters on the display 208. In another example, the reusable module 250 operatively connected to a temperature sensor can establish Bluetooth® communication with the computing device 206. The computing device 206 can receive the patient data including temperature parameters from the reusable module 250 and display the parameters on the display 208. The computing device 206 can receive one or more parameters from the reusable modules 250 and display the one or more parameters on the display 208.

The reusable module 250 can include an ID tag that is active or passive RFID tag. An active RFID tag may be WiFi-enabled, for example. The ID tag can be a barcode (e.g., two-dimensional or three-dimensional) or a WiFi-enabled RFID tag. By communicating with the WiFi access points, the computing device 206 can triangulate its position relative to that WiFi access points. Likewise, the position of the reusable module 250 (and the sensor 240 if the reusable module 250 is operatively connected to the sensor 240) can be triangulated. Thus, the distributed WiFi access points can be used by, for example, the computing device 206 to determine the approximate position of the reusable module 250 (and/or the sensor 240) with respect to the computing device 206. The computing device 206 may also communicate directly with the reusable module 250 in order to, for example, enhance the position approximation determined using the distributed WiFi access points.

Positions of one or more reusable modules 250 can be used to determine relative or absolute positions of the one or more reusable modules 250. For example, consider reusable modules 250A, 250B, 250C, and 250D. When locations of the reusable modules 250A, 250B, and 250C are known, their positional information can be used to determine a position of the reusable module 250D.

The presence or proximity of the reusable module 250 to the computing device 206 may be determined by the reusable module 250 including an RFID tag. An "RFID tag" or simply "tag" can include any wireless communication device and/or communication standard (e.g., RFID, NFC, Bluetooth, ultrasound, infrared, and the like) that can remotely identify a proximate user to a monitor. Tags include, but are not limited to, devices in the form of badges, tags, clip-ons, bracelets or pens that house an RFID chip or other wireless communication components. Tags also encompass smart phones, PDAs, pocket PCs and other mobile computing devices having wireless communications capability. The RFID tag can include identifying information or pairing parameters for the reusable module 250.

The computing device 206 may respond to the departure of all proximate reusable modules 250 by automatically removing displays associated with the reusable modules 250. This feature can provide display patient physiological data only for sensors 240 associated with reusable modules 250 proximate to the computing device 206. The computing device 206 may respond in a similar manner by automatically silencing pulse "beeps" or other non-critical sounds when there are no proximate reusable modules 250 and associated sensors 240.

The computing device 206 can generate alarms when its wireless communication 204 with the reusable module 250 is disrupted or no longer exists. For example, the computing device 206 can create at least one of auditory and visual alarm when the reusable module 250 is no longer mated with the disposable sensor 220.

The computing device 206 can monitor signal strength of the wireless communication 204 between the computing device 206 and the reusable module 250. Under some circumstances, the reusable module 250 may move out of the range of the computing device 206 which may cause the wireless communication 204 to be disrupted. For example, a patient equipped with the reusable module 250 may visit an x-ray room for a routine visit and disrupt the wireless communication 204 between the reusable module 250 and the computing device 206. If the same reusable module 250 becomes available within the range within a period of time, the computing device 206 can automatically reestablish the wireless communication 204. For example, if the patient returns from the x-ray room within 30 minutes, the computing device 206 may be able to reestablish the wireless communication between the reusable module 250 and the computing device 206. Upon reestablishing communications, any information stored on the reusable module 250 for the time period where communication was disrupted can be downloaded to the computing device 206.

The computing device 206 can be configured to not lose (or delete) the pairing parameters received from the reusable dongle 250. This feature can prevent other reusable modules 250 from pairing with the computing device 206 even when the reusable module 250 is no longer wirelessly communicating with the computing device 206. For example, a first computing device 206 and a first reusable module 250 are in a first wireless communication 204. The first computing device 206 can be configured to not "give up" or "give up" the first reusable module 250 even after the first wireless communication 204 is terminated. When configured to "give up," a second reusable module 250 can be paired with the first computing device 206. When configured to "not give up," a second reusable module 250 cannot be paired with the first computing device 206.

This feature can also apply in situations in which the battery 224 of the disposable module 220 is about to be depleted or when the reusable module 250 is removed from the disposable module 220. Without power from the battery 224, the reusable module 250 cannot maintain the wireless communication 204 with the computing device 206. The computing device 206 can be configured to prevent or not prevent other computing device 206 from establishing wireless communication 204 with the reusable module 250. The reusable module 250 can also send a "dying" signal to the computing device 206 providing instructions on pairing or other instructions as the device is removed from the disposable module 220 or when the batteries are depleted. This dying instruction allows the pairing to be maintained.

Computing devices 206 (or dongle 800) can communicate to other computing devices 206 (or other dongles 800) to ensure that each computing device 206 (or dongle 800) is paired to a single reusable module 250 at any time. For example, when a first reusable module 250 is paired (or associated) with a first computing device 206, a second reusable module 250 may not be paired (or associated) with the first computing device 206. However, the first reusable module 250 may be able to pair with a second computing device 206. Pairing the first reusable module 250 with the second computing device 206 can cause the second computing device 206 to inform the first computing device 206 to release its pairing with the first reusable module 250.

The computing device 206 can identify the sensors 240 and the reusable modules 250 associated with the computing device 206. When one or more sensors 240 and reusable modules 250 are wirelessly associated to the computing device 206, it may be advantageous for the computing device 206 to distinguish and indicate different physiological parameters from different sensors 240 or reusable devices 250. For example, the computing device 206 can be associated with two different sensors 240 (and their respective reusable modules 250) for detecting peripheral capillary oxygen saturation (SpO$_2$) and acoustic respiration rate (RRa). The computing device 206 can display information pertaining to the sensors 240 or the reusable modules 250 (for example, sensor name, sensor type, sensor location, sensor ID, reusable module ID, reusable module name) to distinguish patient parameters from different sensors and/or reusable modules.

The reusable module 250 of the sensor assembly 202 can establish wireless communication 204 with mobile devices such as smartphones, tablets, smartwatches, laptops, and the like. The mobile devices can include a mobile application that allows the mobile devices to establish wireless communication 204 with the reusable module 250 of the sensor assembly 202, receive patient physiological parameters from the reusable module 250, and display the patient physiological parameters. In addition to the patient physiological parameters, the mobile application can also display other patient information including, but not limited to, name, age, past medical history, current medications, address, gender, and the like.

The wireless communication 204 between the mobile devices and the reusable module 250 can be in a form of Bluetooth®. The wireless communication 204 between the mobile devices and the reusable module 250 can be established via the Internet. For example, the computing device 206 can be connected to the Internet or a secured network server. Once wireless communication 204 between the reusable module 250 and the computing device 206 is established, the mobile devices can access the Internet or the secure network server to receive and display the patient physiological parameters via the mobile application described above.

The mobile application can include various security measures to prevent third-parties from accessing patient information. The mobile application can be associated with certain mobile devices that has been identified by a healthcare provider. Identification and a passcode may be required for using the application to connect to the reusable module 250 (or the computing device 206), receive patient data (for example, patient data and/or patient physiological parameters), and display patient data. Each of the mobile applications can be associated with a unique access code or an identification code that may be required for receiving patient data from the Internet or the secured network server. The unique access code or the identification code can be associated with the mobile device or the mobile application. The unique access code can be a media access control (MAC) address associated with each of the mobile devices.

Mating of the Dock and Reusable Module

Figure 10A:
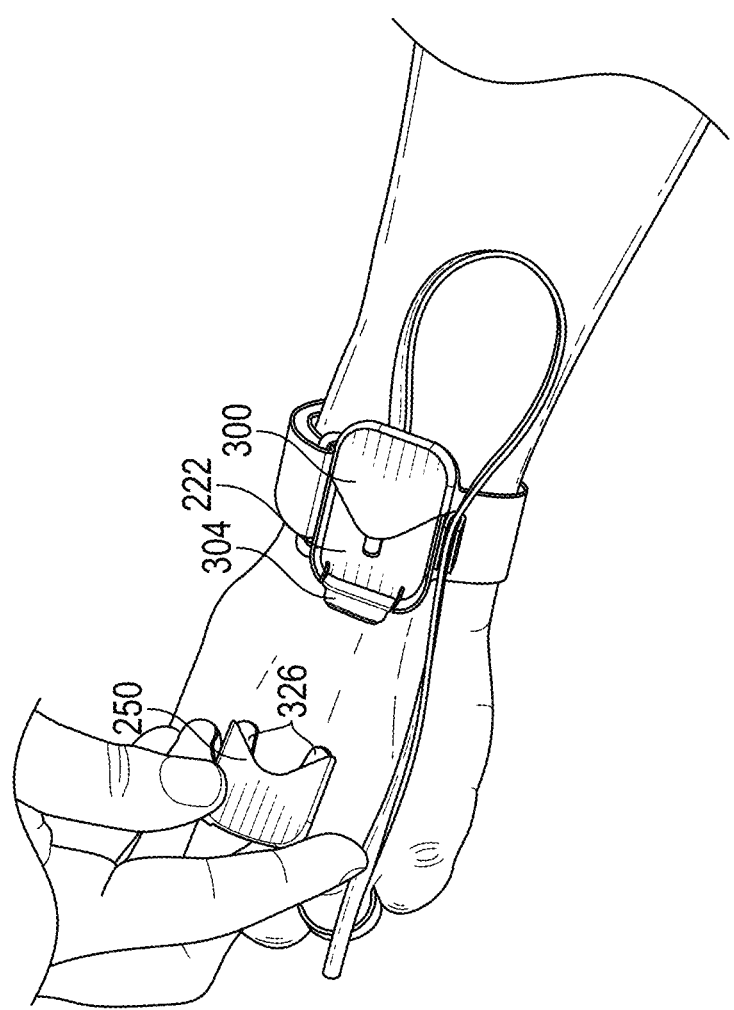
FIGS. 10A-10D illustrate various perspective views of the reusable module and the disposable module of FIG. 3A attached to a wrist of a patient, showing additional details for a method of mating the reusable module with the disposable module.

FIGS. 10A-10D illustrates the process of mating the reusable module 250 with the dock 222 of the disposable module 220. The dock 222 of the disposable module 220 can be attached to a wrist of a patient as shown in FIG. 10A. The dock 222 can include a housing 300 that includes slots 328 (see FIG. 3B) that correspond to the legs 326 of the reusable module 250.

Figure 10B:
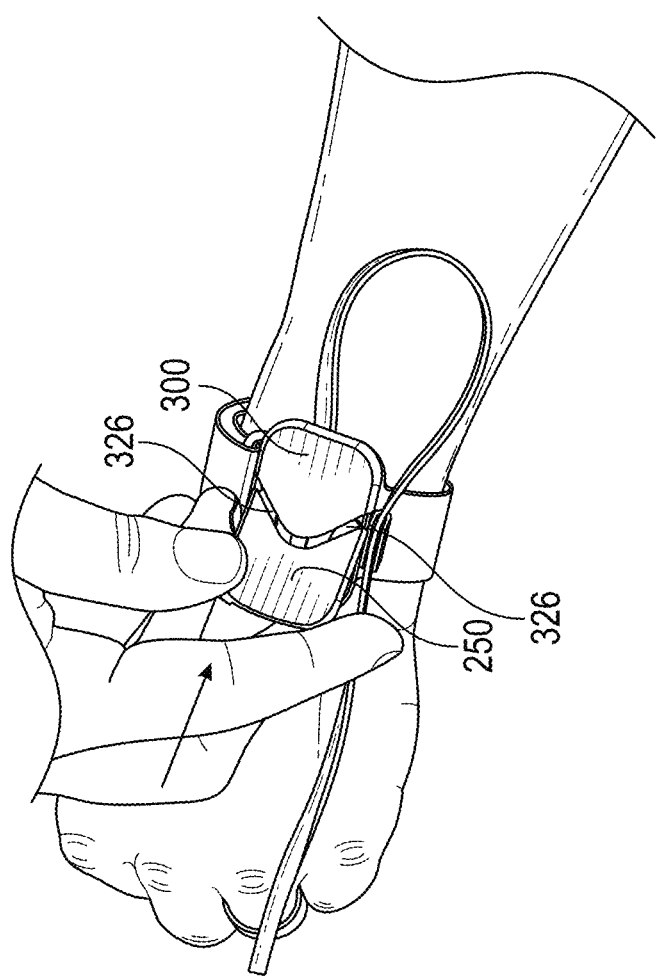

FIG. 10B illustrates the reusable module 250 being inserted into the dock 222. The legs 326 can face the slots 328 of the dock 222 as the reusable module 250 is inserted. When the legs 326 are substantially positioned within the slots 328 of the dock 222, body of the reusable module 250 can be positioned at an angle with respect to the dock 222. One end of the reusable module 250 may be positioned on top of the retainer 304 while at least a portion of the legs 326 are positioned in the slots 328 of the dock 222.

Figure 10C:
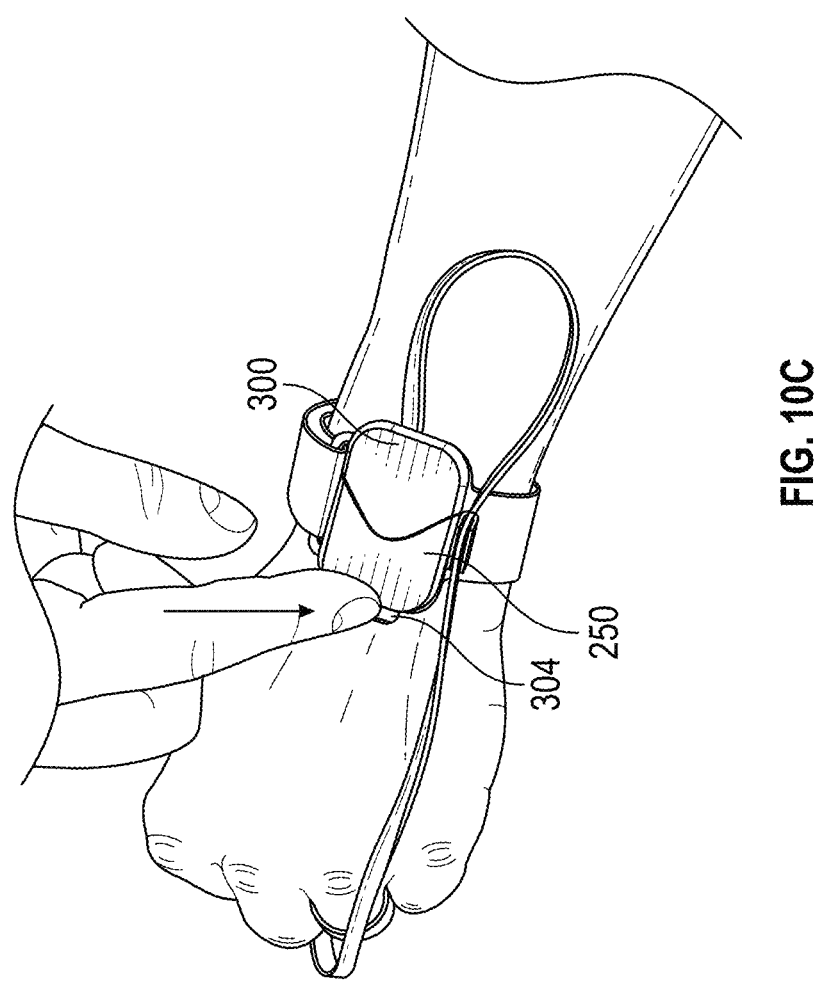
Figure 10D:
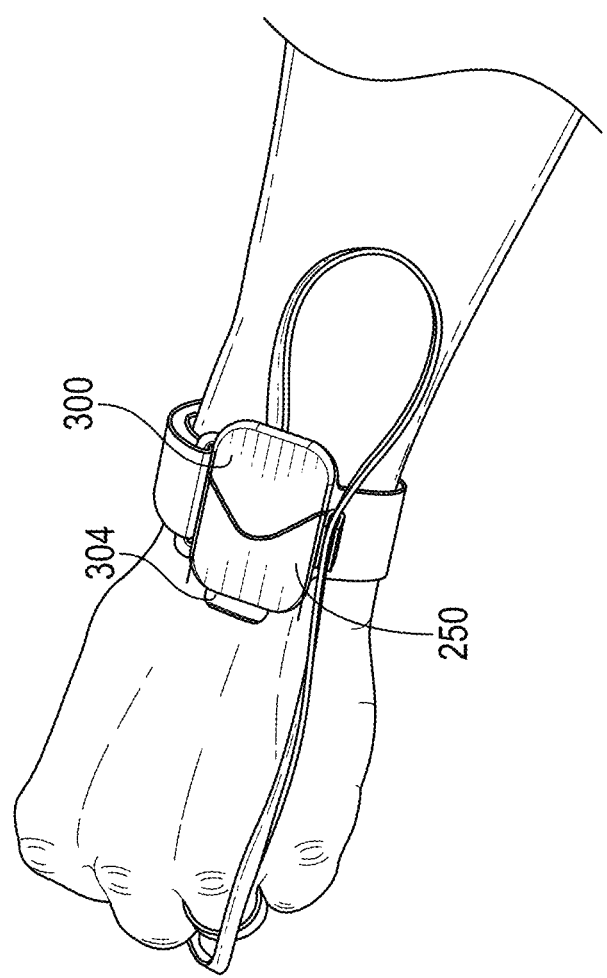

FIG. 10C illustrates the reusable module 250 being pushed down towards the dock 222. As shown in the FIG. 10C, the legs 326 can be partially inserted in the slots 328. The reusable module 250 can be pushed down, which causes the retainer 304 to move away from the housing 300, thus allowing the reusable module 250 to be fully inserted in the dock 222 and mated with the dock 222 as shown in FIG. 10D. When the reusable module 250 is fully inserted, the retainer 304 can snap back in a direction towards the housing 300 and engage with the groove 322 of the reusable module 250 (FIG. 3B). Mating between the reusable module 250 and the dock 222 can cause the legs 326 engage the slots 328 of the housing 300. The engagement between the groove 322 and the protrusion 324 (FIG. 3B) of the retainer 304 can hold the reusable module 250 in place while mated with the dock 222. The engagement between the slots 328 and the legs 326 can hold the reusable module 250 in place.

Methods of Pairing, Collecting Data, and Transmitting Data to Computing Device

Figure 11A:
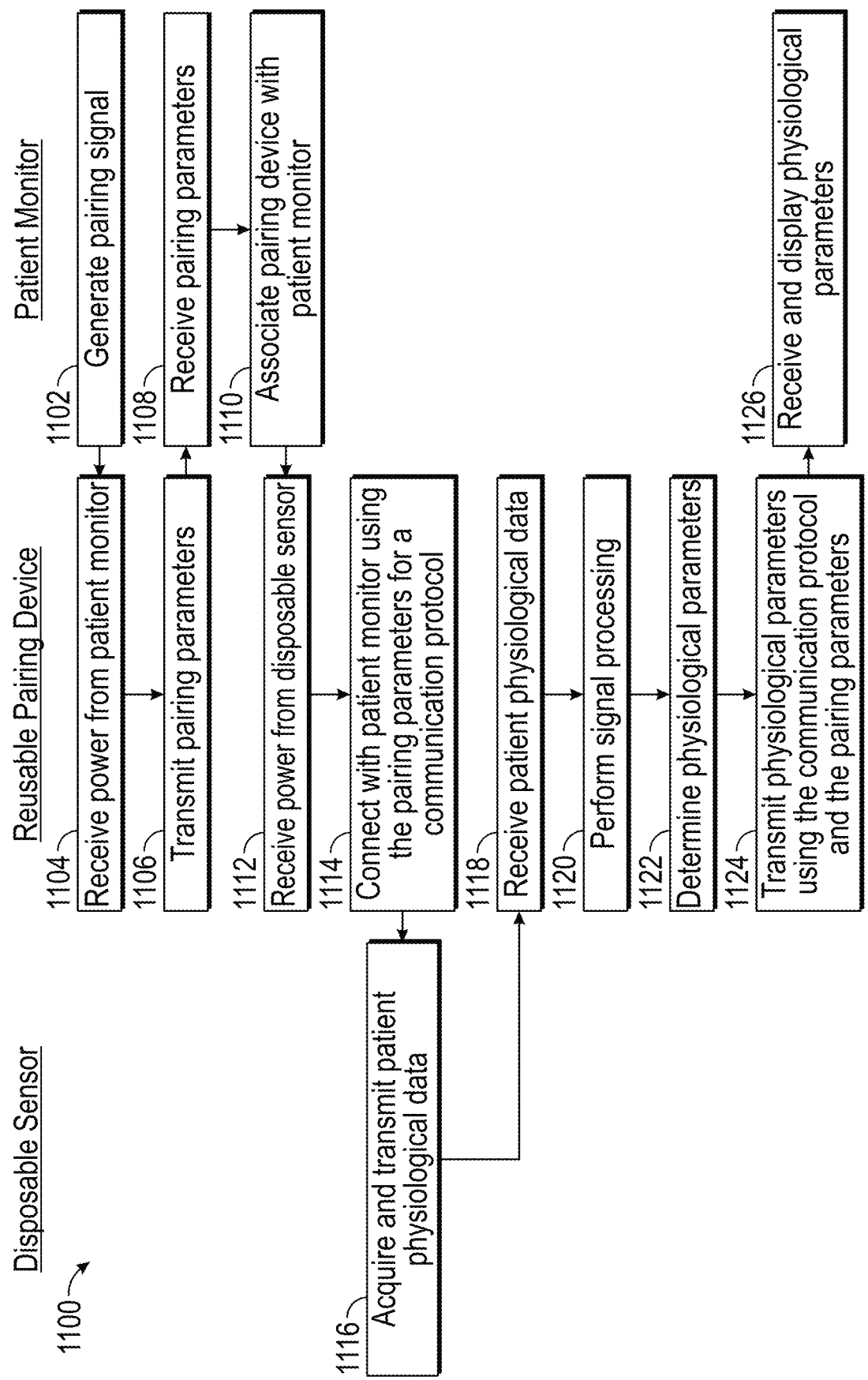
FIG. 11A illustrates a method of establishing a wireless communication using a reusable module, a disposable module, and a computing device for acquiring and displaying patient physiological parameters.

FIG. 11A illustrates a method 1100 of establishing wireless communication between the reusable module 250 and the computing device 206, determining patient physiological parameters using the sensor assembly 202, and displaying the physiological parameters using the computing device 206.

At block 1102, a patient monitor (for example, the computing device 206) can generate and transmit a pairing signal. Generating the transmitting the pairing signal can be done automatically or manually. The pairing signal may be a radio signal. The pairing signal can be configured such that a nearby device, upon receiving the signal, is triggered to transmit an identification information in response. The nearby device may be the reusable module 250. The pairing signal can also contain sufficient power to enable nearby devices to transmit pairing parameters in response to the pairing signal.

Generating and transmitting the pairing signal can be done by different devices. The computing device 206 can generate the pairing signal while the dongle 800 attached to the computing device 206 via the connector 804 can transmit the pairing signal. The dongle 800 can generate and transmit the pairing signal for the computing device 206.

The reusable module 250 located within a predetermined distance from the computing device 206 can receive the pairing signal. This can be advantageous in hospital environments where many patients can be placed within a short distance from an electronic device such as the computing device 206. Such configuration can allow the electronic device (for example, the computing device 206) to receive patient health data only from a patient who is nearby and prevent the electronic device from receiving patient health data from other patients who may not be a patient-in-interest. Strength of the pairing signal can be varied to allow the signal to travel further or closer.

At block 1104, the reusable module 250 can receive power from the pairing signal generated by the computing device 206. The pairing signal can be a high-frequency alternating current which can be used to create a voltage potential. The pairing signal of the computing device 206 may be received when the reusable module 250 is within a predetermined distance. As discussed above, physical contact between the computing device 206 (or the dongle 800) and the reusable module 250 may be required for the reusable module 250 to receive the power from the pairing signal. The reusable module 250 can automatically receive power from the pairing signal. By receiving power from the pairing signal, the antenna 252 of the reusable module may not need to draw power from the battery 226 of the disposable device 220.

At block 1106, the reusable module 250 can use the power received from the pairing signal to transmit identification information to the computing device 206. The identification information can include pairing parameters of the reusable module 250. The identification information may be a tag serial number unique to the reusable module 250. The identification information can include, but not limited to, stock number, lot number, batch number, production date, or other specific information. The computing device 206 can use the identification information to uniquely identify the reusable module 206. The transmission of the identification information can occur automatically.

The reusable module 250 can include a feature that prevents automatic transmission of the identification information to the computing device 206. This feature can be advantageous to prevent inadvertent pairing of the reusable module 205 with the computing device 206. Medical personnel can deal with patients in need of many different types of sensors. In such circumstances, reusable modules 250 may inadvertently be brought proximal to the computing device 206 (or dongle 800). Thus it can be advantageous for the reusable module 250 to have the feature to prevent the reusable modules 250 from automatically pairing with the computing device 206 (or dongle 800) to prevent inadvertent pairing.

At block 1108, the computing device 206 can receive the identification information from the reusable module 250. The dongle 800 connected to the computing device 206 can receive the identification information and relay it to the computing device 206. At block 1110, the computing device 206 can associate with the reusable module 250, which allows the wireless communication 204 to be established between the reusable module 250 and the computing device 206.

The association between the computing device 206 and the reusable module 250 can occur automatically. On the other hand, the association can require a user input via the computing device 206. For example, upon receiving the pairing parameters from the reusable module 250, the computing device 206 can generate a notification prompting a user to allow or disallow the computing device 206 to associate with the reusable module 250. If allowed, the computing device 206 can associate with the reusable module 250 and the reusable module 250 can establish a wireless communication 204 with the computing device 206. If not allowed, the computing device 206 may not associate with the reusable module 250 and the reusable module 250 may not establish a wireless communication 204 with the computing device 206.

Establishing wireless communication 204 can require the reusable module 250 to have an external power source. The battery 224 provides sufficient power for the reusable module 250 to receive raw patient physiological data from the sensor 240 and perform signal processing on the raw data to calculate patient physiological parameters. Moreover, the reusable module 250 can use the power from the battery 224 to use the antenna 252 to wirelessly transmit the calculated parameters to the computing device 206. Without the battery 224 connected to the dock 222, the reusable module 250 cannot receive power via the electrical contacts 228, 258.

At block 1112, the reusable module 250 can mate with the dock 222 and receives power from the battery 224 via the battery circuit 314 and the electrical contacts 228, 258. At block 1114, the reusable module 250 can establish wireless communication 204 with the computing device 206. The wireless communication 204 can be established using the pairing parameters. The wireless communication 204 can be via Bluetooth®, as discussed above. The wireless communication 204 can be one-way or two-way communication between the reusable module 250 and the computing device 206. For example, the reusable module 250 can transmit calculated physiological parameters to the computing device 206. The computing device 206, in return, can transmit a confirmation signal back to the reusable module 250 to let the reusable module 250 know that the calculated parameters were received. The reusable module 250 can include one or more light sources (for example, LEDs) that can generate light when the reusable module 250 receives the confirmation signal from the computing device 206.

At block 1116, the sensor 240 can acquire raw patient physiological data and transmits the data to the dock 222 via the cable 230 and the flex circuit 320. The raw physiological data can be transferred to the reusable module 250 via the electrical contacts 228, 258. The sensor 240 can include, but not limited to, an acoustic sensor, ECG sensor, EEG sensor, respiratory acoustic sensor (RAS), $SpO_2$ sensor, and the like. The sensor 240 can include one or more different types of sensors.

The sensor 240 can be placed on various areas of a patient. The location of the sensor 240 can depend on the type of sensor used for the sensor 240. For example, the sensor 240 can be an $O_3$ sensor typically adhered to a patient's forehead to monitor cerebral oxygenation. In another example, the sensor 240 can be a respiratory acoustic sensor typically attached to a patient's neck near the trachea to detect vibrations associated with respiration.

At block 1118, the processor 254 of the reusable module 250 can receive the raw patient physiological data from the sensor 240 of the disposable module 220. The raw patient physiological data can be stored in the memory 256.

At block 1120, the processor 254 of the reusable module 250 can perform signal processing on the raw physiological data. Various types of signal processing used on the physiological data raw can include, but not limited to, analog signal processing, continuous-time signal processing, discrete-time signal processing, digital signal processing, or nonlinear signal processing. For example, continuous-time signal processing such as time domain, frequency domain, and complex frequency domain can be used. Some of the signal processing methods that can be used on the raw physiological data include, but not limited to, passive filters, active filters, additive mixers, integrators, delay lines, compandors, multiplicators, voltage-controlled filters, voltage-controlled oscillators, phase-locked loops, time domain, frequency domain, fast Fourier transform (FFT), finite impulse response (FIR) filter, infinite impulse response (IIR) filter, and adaptive filters. Such processing techniques can be used to improve signal transmission, storage efficiency, and subjective quality. In addition, such processing techniques can be used to emphasize or detect components of interest in the raw physiological data. Noise filtering can be used to filter out raw physiological data corrupted by noise due to patient movement, electromagnetic interference, or ambient light.

Signal processing can determine the absorbance's of the light due to pulsating arterial blood. For example, pulse oximeter generates a blood-volume plethysmograph waveform from which oxygen saturation of arterial blood, pulse rate, and perfusion index, among other physiological parameters, can be determined. In the context of pulse oximetry, the sensor 240 can use adaptive filter technology to separate an arterial signal, detected by a pulse oximeter sensor, from the non-arterial noise for example, venous blood movement during motion). During routine patient motions (shivering, waving, tapping, etc.), the resulting noise can be quite substantial and can easily overwhelm a conventional ratio based oximetry system. This can provide accurate blood oxygenation measurements even during patient motion, low perfusion, intense ambient light, and electrocautery interference.

At block 1122, the processor 254 of the reusable module 250 can determine patient physiological parameters by processing the raw physiological data. The processor 254 can then store the processed data and the calculated parameters in the memory 256 before transmitting them to the computing device 206.

The processed data can be indicative of an amount of attenuation of predetermined wavelengths (ranges of wavelengths) of light by body tissues, such as, for example, a digit, portions of the nose or year, a foot, or the like. For example, the predetermined wavelengths correspond to specific physiological parameter data desired including, but not limited, blood oxygen information such as oxygen content (SpOC®), oxygen saturation ($SpO_2$), blood glucose, total hemoglobin (SbHb), methemoglobin (SpMet®), carboxyhemoglobin (SpCO), bulk tissue property measurements, water content, pH, blood pressure, respiration related information, cardiac information, perfusion index (PI), pleth variability indices (PVI®), or the like, which can be used by the mobile computing device to determine the condition of the user. The processed data can provide information regarding physiological parameters such as EEG, ECG, heart beats per minute, acoustic respiration rate (RRa), breaths per minute, end-tidal carbon dioxide ($EtCO_2$), respiratory effort index, return of spontaneous circulation (ROSC), or the like, which can be used to determine the physiological condition of the user.

At block 1124, the processor 254 of the reusable module 250 can transmit the patient physiological parameters to the computing device 206 via the antenna 252 using the communication protocol and the pairing parameters. It can be advantageous to transmit the calculated physiological parameters (for example, 60% $SpO_2$) as opposed to transmit the raw physiological data to the computing device 206. Compared to calculated physiological parameters, the raw physiological data can be larger in size and thus require larger bandwidth during transmission to the computing device 206. Calculated physiological parameters, on the other hand, can be much smaller in size and can require smaller bandwidth to transmit. Therefore, transmitting patient physiological parameters instead of raw physiological data can lead to decreased battery consumption and longer battery life for the disposable module 220.

The transmission of the physiological parameters can occur wirelessly via NFC. For example, the transmission of the physiological parameters occur wirelessly via Bluetooth. The transmission of the physiological parameters may occur via a cable.

At block 1126, the computing device 206 can receive the patient physiological parameters and displays them using the display 208. As discussed above, the computing device can include the display 208 that can display various patient physiological parameters including, but not limited to, body temperature, heart rate, blood oxygen level, blood pressure, and the like.

Figure 11B:
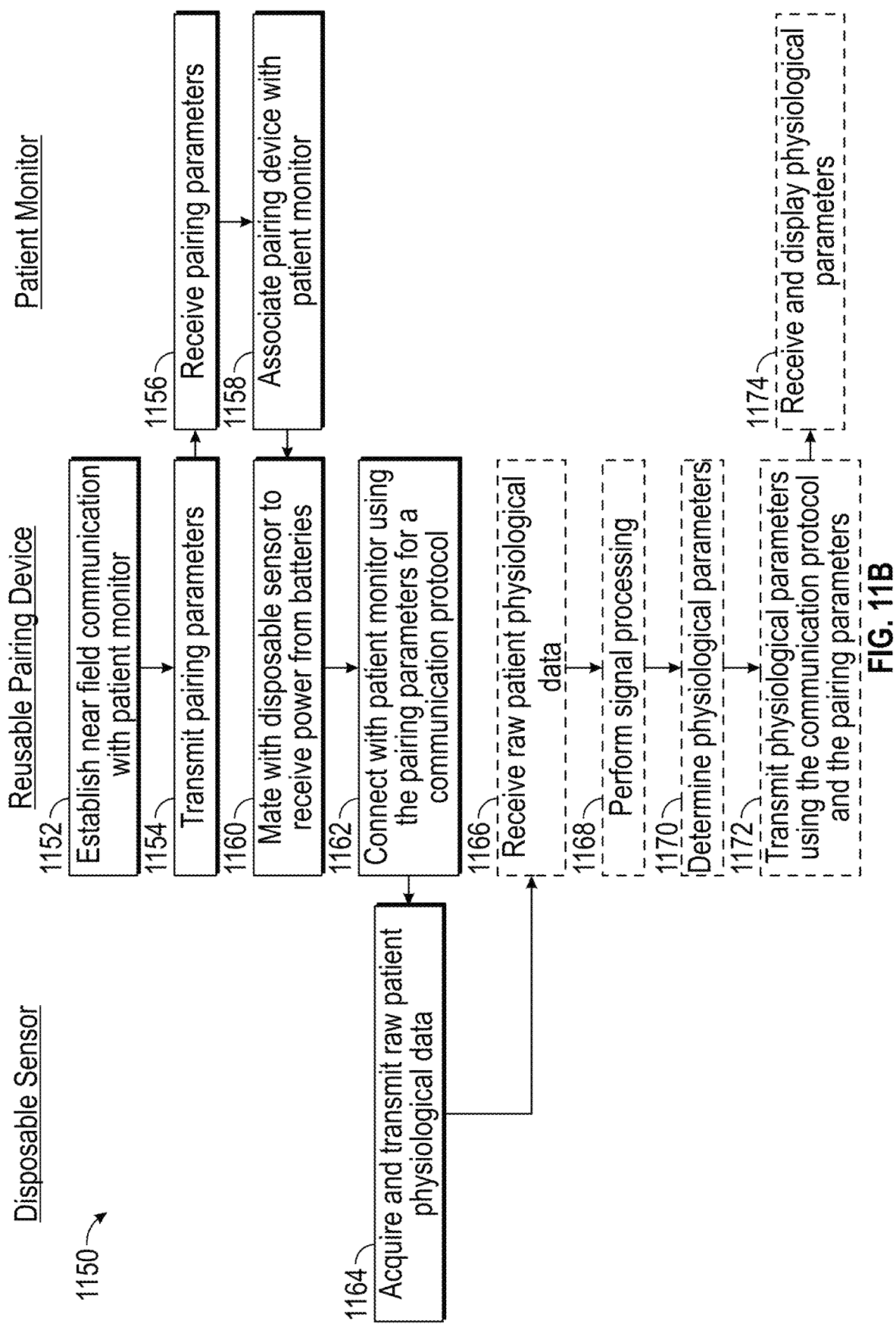
FIG. 11B illustrates another method of establishing wireless communication using a reusable module, a disposable module, and a computing device for acquiring and displaying patient physiological parameters.

FIG. 11B illustrates another method 1150 of establishing wireless communication between the reusable module 250 and the computing device 206, determining patient physiological parameters using the sensor assembly 202, and displaying the physiological parameters using the computing device 206.

At block 1152, the reusable module 250 can establish a NFC (near field communication) with the computing device 206. As discussed above, establishing a NFC can require the reusable module 250 to be within a predetermined distance of the computing device 206. As noted above, the NFC can be established between the body 802 of the dongle 800 and the reusable module 250.

At block 1154, the reusable module 250 can transmit pairing parameters to the computing device 206. The transmission of the pairing parameters to the computing device 206 can occur when the reusable module 250 establishes the NFC with the computing device 206. At block 1156, the computing device 206 can receive the pairing parameters from the reusable module 250. The computing device 206 can use the dongle 800 to receive the pairing parameters. For example, the body 802 of the dongle 800 can wirelessly receive the pairing parameters and transmit the pairing parameters to the computing device 206 via the cable 806 and the connector 804.

At block 1158, the computing device 206 or the body 802 can associate with the reusable module 250 using the pairing parameters. Once associated, the computing device 206 or the body 802 may wait for the wireless communication 204 from the reusable module 250. As noted above, the wireless communication 204 can be made via Bluetooth®. At block 1164, the sensor 240 of the disposable module 220 can acquire physiological data and transmit the data to the reusable module 250. The physiological data acquired by the sensor 240 and transmitted to the reusable module 250 can be raw physiological data.

Blocks 1166 through 1174 may be optional. At block 1166, the reusable module can receive the patient physiological data from the disposable module 220. At block 1168, the reusable module 250 can perform signal processing on the patient physiological data. At block 1170, the reusable module 250 can determine patient physiological parameters using the processed physiological data. At block 1172, the reusable module 250 can transmit patient physiological parameters using the wireless communication 204 established between the reusable module 250 and the computing device 206. The body 802 of the dongle 800 may wirelessly receive the patient physiological parameters from the reusable module 250 and transmit the parameters to the computing device via the cable 806 and the connector 804. At block 1174, the computing device 206 receives the patient physiological parameters and displays the parameters on the display 208.

Figure 12:
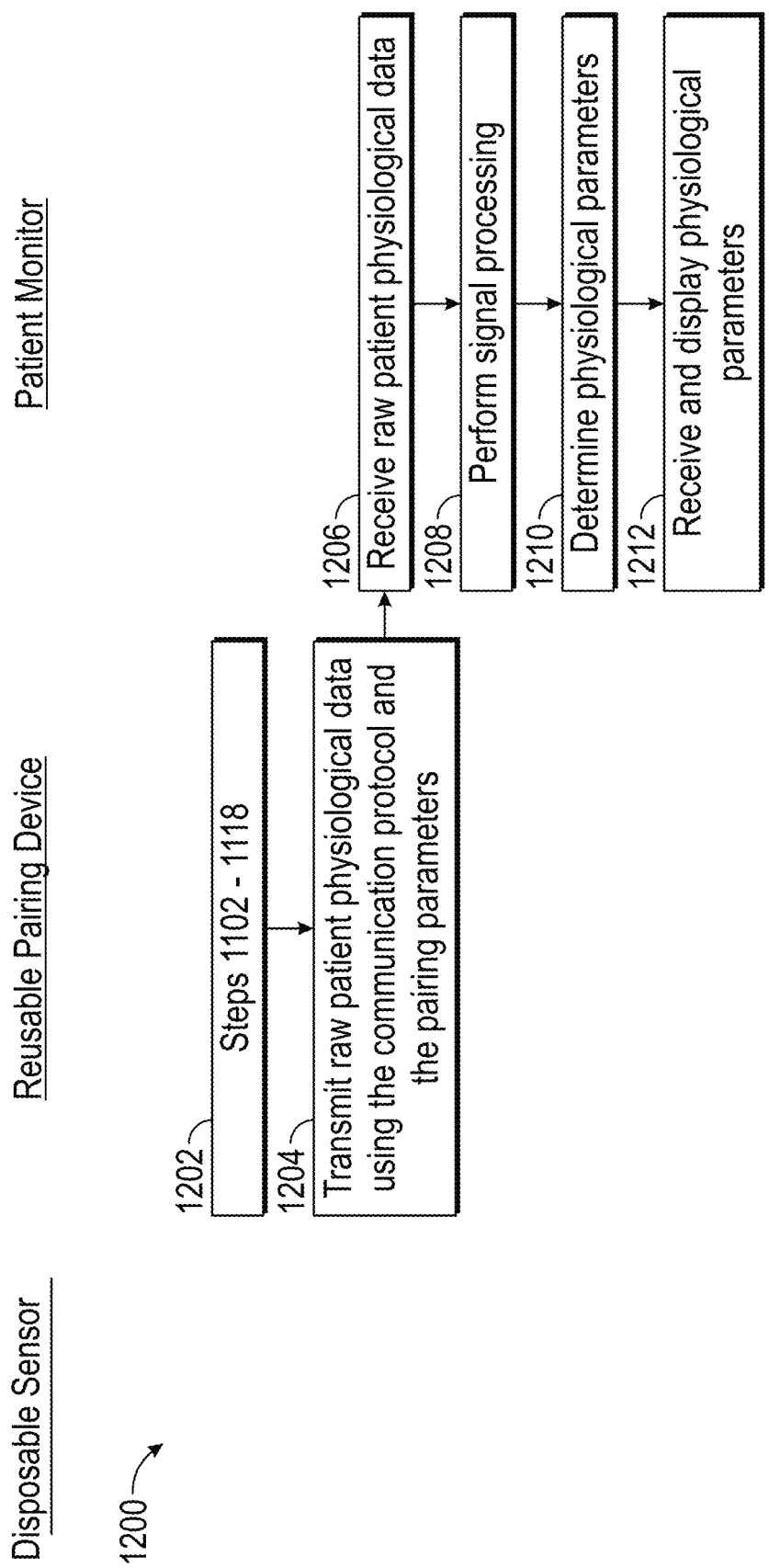
FIG. 12 illustrates another embodiment of a method of acquiring and displaying patient physiological parameters using a reusable module, a disposable module, and a computing device.

FIG. 12 illustrates another method 1200 of determining patient physiological parameters using the sensor assembly 202 and displaying the physiological parameters using the computing device 206.

At block 1202, the processor 254 of the reusable module 250 receives raw patient physiological data from the sensor 240 of the disposable module 220 according to the blocks 1102-1120 of FIG. 11.

At block 1204, the processor 254 of the reusable module 250 transmits the raw patient physiological data to the computing device 206. The process 254 can use the antenna 252 to transmit the raw data via the wireless communication 204 established between the reusable module 250 and the computing device 206. As mentioned above, the wireless communication 204 can be one-way or two-way between the reusable module 250 and the computing device 206.

At block 1206, the computing device 206 receives the raw patient physiological data. At block 1208, the computing device 206 performs signal processing on the raw patient physiological data. At block 1210, the computing device 206 determines patient physiological parameters using processed raw patient physiological data. At block 1212, the computing device 206 displays the determined physiological parameters on the display 208.

Mobile Application

As discussed above, the computing device 206 can be a mobile device 1300 such as a phone, tablet, watch and the like. The mobile device 1300 can include a mobile application that can establish wireless communication with the reusable module 250 via a wireless communication protocol, such as Bluetooth or the like.

FIG. 13A illustrates a mobile application being executed on the mobile device 1300 (for example, a mobile phone) to establish a wireless communication with the reusable module 250. The mobile application can pair with nearby reusable modules 250. In an example, a user can press a pair button 1302 to cause the mobile application to search for nearby reusable modules 250. The mobile application can create a screen 1304 to display nearby reusable modules 250. The screen 1304 can provide MAC address or any other pairing information unique to the reusable modules 250. The mobile application may automatically search for nearby reusable modules 250 without any user intervention or input.

FIGS. 13B-13E illustrate various examples the mobile application displaying patient parameters. Triggering a home button 1308 can cause the mobile application to show real-time, numerical and graphical illustration of patient parameters, as shown in FIG. 13A. The mobile application can show numerical parameters 1310 (for example, patient's $SpO_2$, PR BPM, and PI readings) in real time or with a predetermined delay. The mobile application may show graphical illustration 1314 of patient parameters that show real-time trend of the parameters. For example, a user can trigger an $SpO_2$ portion of the display to cause the mobile application to show real-time trend of the $SpO_2$ parameters.

Figure 13C:
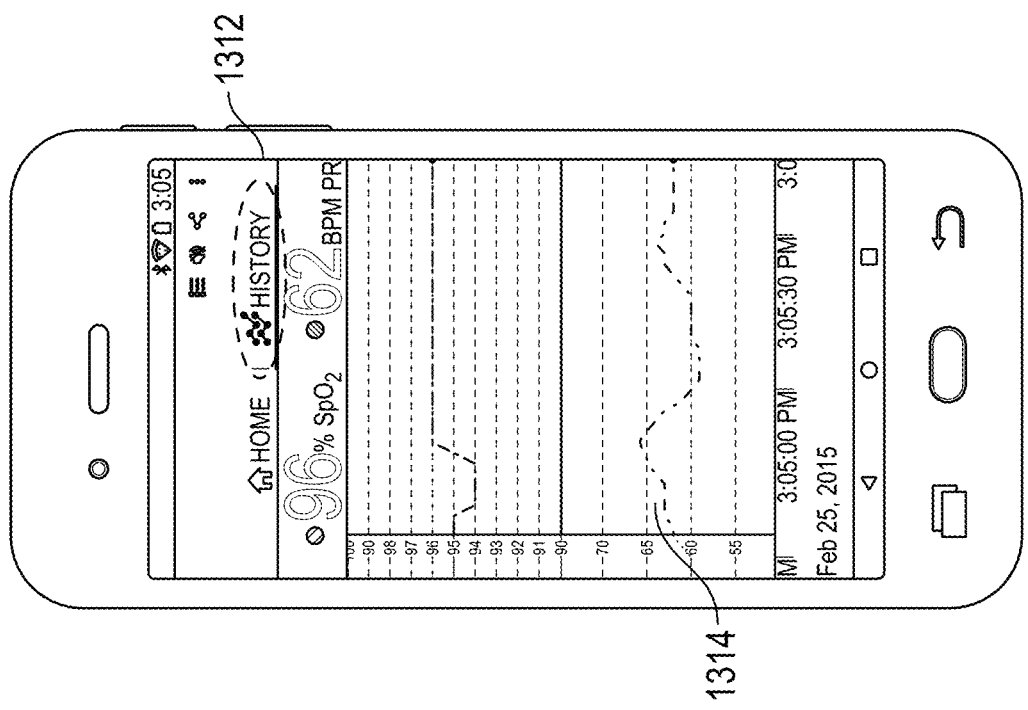

As shown in FIG. 13C, triggering a history button 1312 can cause the mobile application to show the graphical illustration 1314 showing historical trends of patient health parameters. The graphical illustration 1314 can have an x-axis showing timestamp and a y-axis showing parameter values. The mobile application may show real-time numerical values of patient health parameter above or below the graphical illustration 1314. The real-time numerical values can be embedded within the graphical illustration 1314.

Figure 13D:
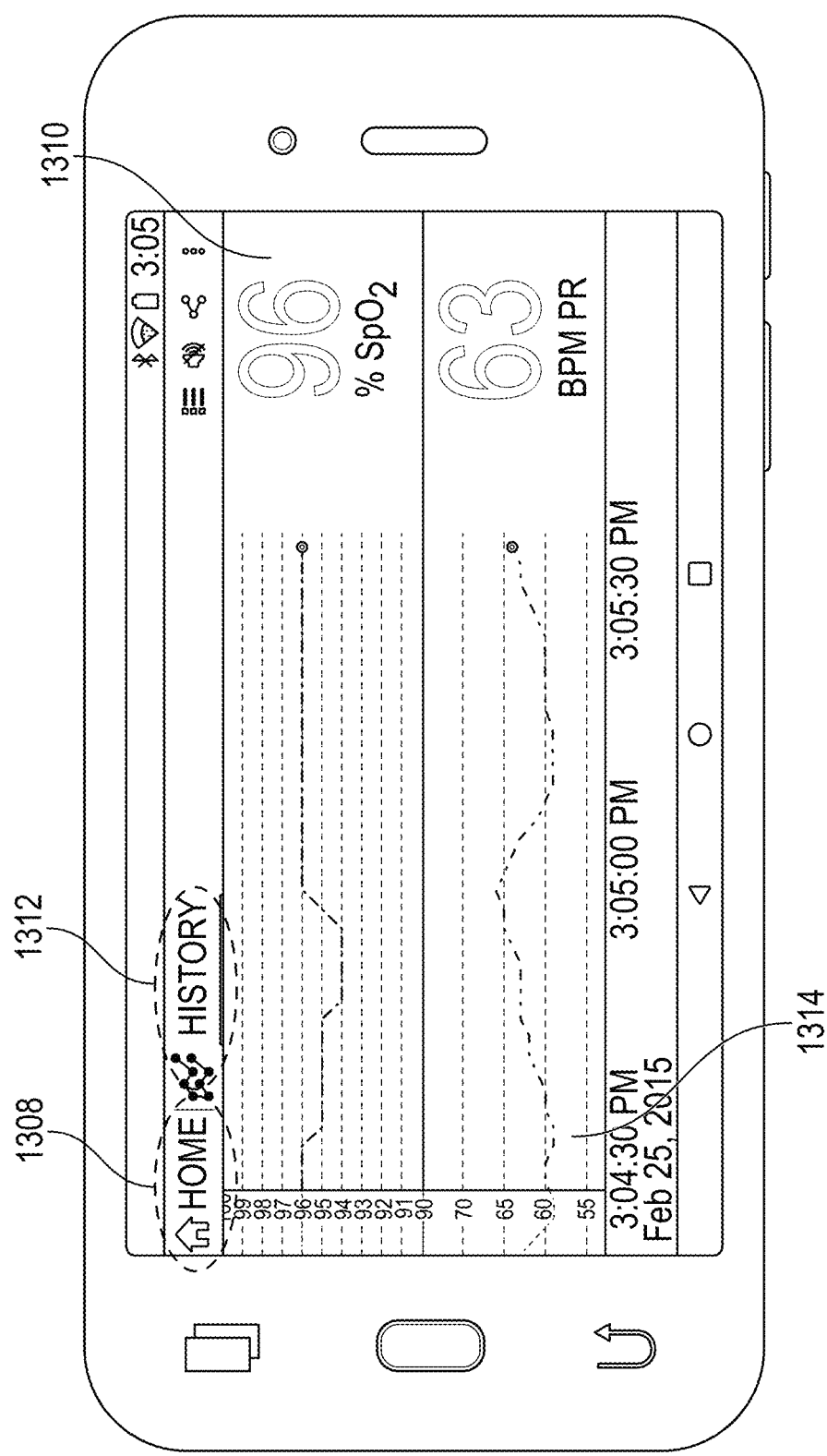
Figure 13E:
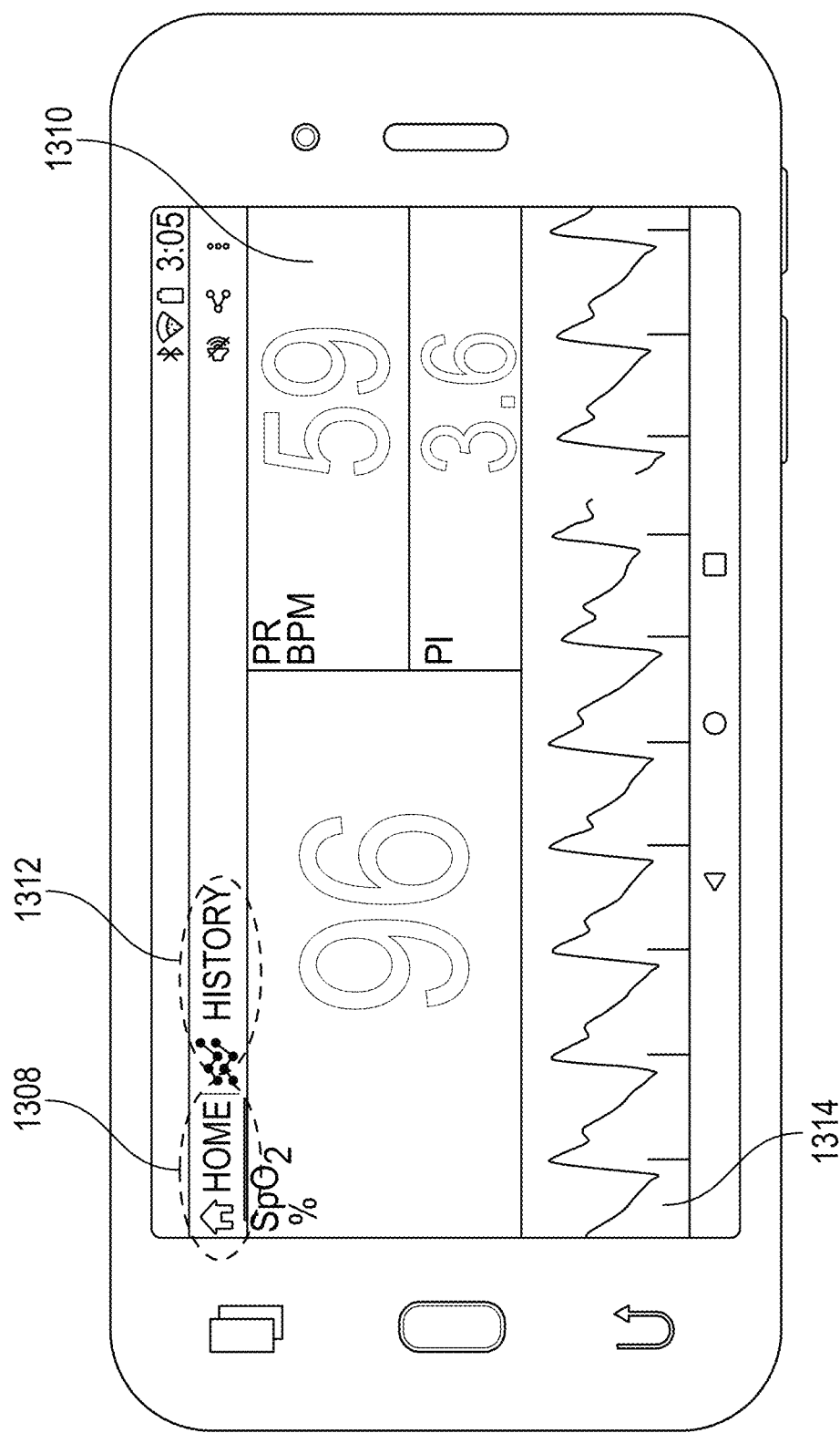

As shown in FIGS. 13D and 13E, the mobile application can display at least one of the numerical parameters 1310 and the graphical illustration 1314 in a landscape view.

Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the systems, devices or methods illustrated can be made without departing from the spirit of the disclosure. As will be recognized, certain embodiments described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred embodiments, but is to be defined by reference to claims.

What is claimed is:

1. A system for collecting and wirelessly transmitting physiological data of a patient, the system comprising:
  a disposable noninvasive sensor assembly comprising:
    a housing comprising an outer surface, a recess along a portion of the outer surface, at least one opening arranged within the recess and configured to allow air to enter an interior of the housing, a first end, a second end opposite the first end, a first lip at the first end, and a second lip at the first end, wherein the first and second lips are spaced from one another;
    a battery stored within the interior of the housing;
    a cable;
    a sensor element attached to the housing via the cable, the sensor element configured to attach to a finger of the patient;
    a dock coupled to the housing such that the housing covers a first portion of the dock, wherein the first lip of the housing and the dock define a first slot along the first end of the housing and the second lip of the housing and the dock define a second slot along the first end of the housing, the first and second slots spaced from one another; and a strap coupled to the dock and configured to attach the disposable noninvasive sensor assembly to the patient; and a reusable transmitter assembly comprising:
  a body comprising a top surface, a first end, a second end opposite the first end of the body;
  a first leg arranged on the first end of the body, wherein a portion of the first leg is recessed from the top surface of the reusable transmitter assembly;
  a second leg arranged on the first end of the body, wherein a portion of the second leg is recessed from the top surface of the reusable transmitter assembly, and wherein the first leg and the second leg are spaced from one another;
  a processor within an interior of the body;
  a memory within the interior of the body; and
  a wireless communication device within the interior of the body;
wherein the reusable transmitter assembly is configured to be secured to the disposable noninvasive sensor assembly at least partially via engagement of said recessed portions of the first and second legs with the first and second lips, said engagement between said recessed portions of the first and second legs with the first and second lips configured to operably position said recessed portions of the first and second legs within the first and second slots of the disposable noninvasive sensor assembly, and
wherein the reusable transmitter assembly is configured to receive the physiological data of the patient from the disposable noninvasive sensor assembly when secured thereto.

2. The system of claim 1, wherein the battery is configured to react with the air entering the interior of the housing via the at least one opening and generate power.

3. The system of claim 1, wherein the battery is configured to provide power for the disposable noninvasive sensor assembly and the reusable transmitter assembly.

4. The system of claim 1, wherein the reusable transmitter assembly does not include an energy storage device.

5. The system of claim 1, wherein the at least one opening is covered with a seal prior to use.

6. The system of claim 5, wherein the seal is configured to prevent the air from entering the interior of the housing via the at least one opening and reacting with the battery.

7. The system of claim 1, wherein the recess extends to one or more edges of the housing such that when a top surface of the housing is covered, the recess extending to the one or more edges of the housing ensures that the at least one opening remains exposed to the air.

8. The system of claim 1, wherein the recess is a channel.

9. A system for collecting and wirelessly transmitting physiological data of a patient, the system comprising:
  a disposable noninvasive sensor assembly comprising:
    a housing comprising at least one opening configured to allow air to enter an interior of the housing, a first end, a second end opposite the first end, a first lip at the first end, and a second lip at the first end, wherein the first and second lips are spaced from one another;
    a battery stored within the interior of the housing;
    a dock coupled to the housing such that the housing covers a first portion of the dock, wherein the first lip of the housing and the dock define a first slot along the first end of the housing and the second lip of the housing and the dock define a second slot along the first end of the housing, the first and second slots spaced from one another;
    a cable;
    a sensor element attached to the housing via the cable, the sensor element configured to attach to a finger of the patient; and
    a strap coupled to the dock; and
  a reusable transmitter assembly comprising:
    a top surface, a first end, a second end opposite the first end of the reusable transmitter assembly;
    a first leg arranged on the first end of the reusable transmitter assembly, wherein a portion of the first leg is recessed from the top surface of the reusable transmitter assembly; and
    a second leg arranged on the first end of the reusable transmitter assembly, wherein a portion of the second leg is recessed from the top surface of the reusable transmitter assembly;
    wherein the first leg and the second leg are spaced from one another;
  wherein the reusable transmitter assembly is configured to be secured to the disposable noninvasive sensor assembly at least partially via engagement of said recessed portions of the first and second legs with the first and second lips, said engagement between said recessed portions of the first and second legs with the first and second lips configured to operably position said recessed portions of the first and second legs within the first and second slots of the disposable noninvasive sensor assembly, and
  wherein the reusable transmitter assembly is configured to receive the physiological data of the patient from the disposable noninvasive sensor assembly when secured thereto.

10. The system of claim 9, wherein the reusable transmitter assembly further comprises a wireless communication device configured to wirelessly transmit the physiological data to a remote patient monitoring device.

11. The system of claim 9, wherein the strap is configured to attach the disposable noninvasive sensor assembly to a wrist of the patient.

12. A disposable noninvasive sensor assembly for collecting and transmitting physiological data of a patient to a remote monitoring device, the disposable noninvasive sensor assembly comprising:
  a sensor element configured to attach to a finger of the patient and collect physiological data of the patient;
  a housing comprising at least one opening configured to allow air to enter an interior of the housing, a first end, a second end opposite the first end, a first lip at the first end, and a second lip at the first end, wherein the first and second lips are spaced from one another;
  a battery stored within the interior of the housing, the battery configured to react with the air that enters the interior of the housing;
  a cable connected to the sensor element and the housing;
  a dock coupled to the housing such that the housing covers a first portion of the dock, wherein the first lip of the housing and the dock define a first slot along the first end of the housing and the second lip of the housing and the dock define a second slot along the first end of the housing, the first and second slots spaced from one another; and
  a strap coupled to the dock and configured to attach the disposable noninvasive sensor assembly to the patient;
  wherein the disposable noninvasive sensor assembly is configured to be secured to a reusable transmitter assembly at least partially via engagement of portions of the reusable transmitter assembly with the first and second lips, said engagement between said portions with the first and second lips configured to operably position said portions of the reusable transmitter assembly within the first and second slots of the disposable noninvasive sensor assembly, and wherein the battery of the disposable noninvasive sensor assembly is configured to provide power for the reusable transmitter assembly when the reusable transmitter assembly is secured to the disposable noninvasive sensor assembly.

13. The disposable noninvasive sensor assembly of claim 12, wherein the housing further comprises a recess along a portion of an outer surface of the housing, and wherein said at least one opening is arranged within the recess.

14. The disposable noninvasive sensor assembly of claim 13, wherein the recess extends to one or more edges of the housing such that when a top surface of the housing is covered, the recess extending to the one or more edges of the housing ensures that the at least one opening is exposed to the air.

15. The disposable noninvasive sensor assembly of claim 13, wherein the recess is a channel.

16. The disposable noninvasive sensor assembly of claim 12, wherein the disposable noninvasive sensor assembly includes a retainer and the reusable transmitter assembly includes a groove, and wherein the reusable transmitter assembly is further configured to be secured to the disposable noninvasive sensor assembly via engagement between the retainer and the groove.

17. A system for collecting and wirelessly transmitting physiological data of a patient, the system comprising:
 a disposable noninvasive sensor assembly comprising:
  a housing comprising a first end, a second end opposite the first end, a first lip at the first end, and a second lip at the first end, wherein the first and second lips are spaced from one another;
  a dock coupled to the housing such that the housing covers a first portion of the dock, wherein the first lip of the housing and the dock define a first slot along the first end of the housing and the second lip of the housing and the dock define a second slot along the first end of the housing, the first and second slots spaced from one another;
  a cable;
  a sensor element attached to the housing via the cable, the sensor element configured to attach to a finger of the patient; and
  a strap coupled to the dock; and
 a reusable transmitter assembly comprising:
  a top surface, a first end, a second end opposite the first end of the reusable transmitter assembly;
  a first leg arranged on the first end of the reusable transmitter assembly, wherein a portion of the first leg is recessed from the top surface of the reusable transmitter assembly; and
  a second leg arranged on the first end of the reusable transmitter assembly, wherein a portion of the second leg is recessed from the top surface of the reusable transmitter assembly;
  wherein the first leg and the second leg are spaced from one another;
 wherein the reusable transmitter assembly is configured to be secured to the disposable noninvasive sensor assembly at least partially via engagement of said recessed portions of the first and second legs with the first and second lips, said engagement between said recessed portions of the first and second legs with the first and second lips configured to operably position said recessed portions of the first and second legs within the first and second slots of the disposable noninvasive sensor assembly, and
 wherein the reusable transmitter assembly is configured to receive the physiological data of the patient from the disposable noninvasive sensor assembly when secured thereto.

18. A disposable noninvasive sensor assembly for collecting and transmitting physiological data of a patient to a remote monitoring device, the disposable noninvasive sensor assembly comprising:
 a sensor element configured to attach to a finger of the patient and collect physiological data of the patient;
 a housing comprising a first end, a second end opposite the first end, a first lip at the first end, and a second lip at the first end, wherein the first and second lips are spaced from one another;
 a cable connected to the sensor element and the housing;
 a dock coupled to the housing such that the housing covers a first portion of the dock, wherein the first lip of the housing and the dock define a first slot along the first end of the housing and the second lip of the housing and the dock define a second slot along the first end of the housing, the first and second slots spaced from one another; and
 a strap coupled to the dock and configured to attach the disposable noninvasive sensor assembly to the patient;
 wherein the disposable noninvasive sensor assembly is configured to be secured to a reusable transmitter assembly at least partially via engagement of portions of the reusable transmitter assembly with the first and second lips, said engagement between said portions with the first and second lips configured to operably position said portions of the reusable transmitter assembly within the first and second slots of the disposable noninvasive sensor assembly, and
 wherein a battery of the disposable noninvasive sensor assembly is configured to provide power for the reusable transmitter assembly when the reusable transmitter assembly is secured to the disposable noninvasive sensor assembly.

* * * * *